(12) United States Patent
Walsh et al.

(10) Patent No.: US 9,890,422 B2
(45) Date of Patent: Feb. 13, 2018

(54) PLANT EUKARYOTIC TRANSLATION INITIATION FACTOR 4E

(75) Inventors: John Anthony Walsh, Coventry (GB); Charlotte Florence Nellist, Coventry (GB); Guy Cameron Barker, Leamington (GB); Carol Elizabeth Jenner, Broadway (GB)

(73) Assignee: Syngenta Participations AG, Basel (CH)

( * ) Notice: Subject to any disclaimer, the term of this patent is extended or adjusted under 35 U.S.C. 154(b) by 748 days.

(21) Appl. No.: 13/805,859

(22) PCT Filed: Jun. 24, 2011

(86) PCT No.: PCT/GB2011/051192
§ 371 (c)(1),
(2), (4) Date: Jan. 10, 2013

(87) PCT Pub. No.: WO2011/161466
PCT Pub. Date: Dec. 29, 2011

(65) Prior Publication Data
US 2013/0117879 A1    May 9, 2013

(30) Foreign Application Priority Data
Jun. 25, 2010   (GB) .................. 1010740.7

(51) Int. Cl.
| | | |
|---|---|---|
| C12N 15/82 | (2006.01) |
| A01H 1/04 | (2006.01) |
| A01H 3/00 | (2006.01) |
| C12Q 1/68 | (2006.01) |
| C12N 15/01 | (2006.01) |
| C07K 14/415 | (2006.01) |
| A01H 1/02 | (2006.01) |
| A01H 1/06 | (2006.01) |

(52) U.S. Cl.
CPC ............. *C12Q 1/6827* (2013.01); *A01H 1/02* (2013.01); *A01H 1/04* (2013.01); *A01H 1/06* (2013.01); *A01H 3/00* (2013.01); *C07K 14/415* (2013.01); *C12N 15/01* (2013.01); *C12N 15/8283* (2013.01); *C12Q 1/6806* (2013.01); *C12Q 1/686* (2013.01); *C12Q 1/6816* (2013.01)

(58) Field of Classification Search
None
See application file for complete search history.

(56) References Cited

U.S. PATENT DOCUMENTS

2005/0255455 A1   11/2005   Caranta et al.

OTHER PUBLICATIONS

Rusholme et al (2007) J. of Gen. Virol. 88: 3177-3186.*
Lellis et al. Loss-of-susceptibility mutants of *Arabidopsis thaliana* reveal an essential role for eIF(iso)4E during potyvirus infection. Current Biology. 2002. 12: 1046-1051.*

(Continued)

*Primary Examiner* — Ashley K Buran
(74) *Attorney, Agent, or Firm* — Karen A. Magri

(57) ABSTRACT

The invention relates to plants, and in particular to virus-resistant plants, and to methods of generating such plants. The invention extends to eukaryotic translation initiation factor variants and isoforms thereof, and to nucleic acids involved in the splicing of such variant factors, and uses thereof in methods for producing plants that are resistant to viral infections.

4 Claims, 4 Drawing Sheets

(56) References Cited

OTHER PUBLICATIONS

Duprat et al. The *Arabidopsis eukaryotic* initiation factor (iso) 4E is dispensible for plant growth but required for susceptibility to potyviruses. The Plant Journal. 2002. 32: 927-934.*

Ruffel et al. Simultaneous mutations in translation initiation factors eIF4E and eIF(iso)4E are required to prevent pepper veinal mottle virus infection of pepper. Journal of General Virology. 2006. 87: 2089-2098.*

Gopalan. A multidirectional non-cell autonomous control and a genetic interaction restricting tobacco etch virus susceptibility in *Arabidopsis*. PLoS ONE. 2007. 10(e985): 1-9.*

Smykal et al. Marker assisted pea breeding: eIF4E allele specific markers to pea seed-borne mosaic virus (PSbMV) resistance. Molecular Breeding. 2010. 26: 425-438.*

International Search Report in International Application No. PCT/GB2011/051192 dated Oct. 7, 2011 (5 pages).

Ruffel et al., "A natural recessive resistance gene against potato virus Y in pepper corresponds to the eukaryotic initiation factor 4E (eIF4E)" The Plant Journal (2002) 32, 1067-1075.

Maule et al., "Sources of natural resistance to plant viruses: status and prospects" Molecular Plant Pathology (2007) 8(2), 223-231.

Piron et al., "An Induced Mutation in Tomato eIF4E Leads to Immunity to Two Potyviruses," PLoS ONE, Jun. 2010, vol. 5, Issue 6, 10 pages.

International Preliminary Report on Patentability in International Application No. PCT/GB2011/051192 dated Dec. 28, 2012 (6 pages).

Sato et al., "Selective involvement of members of the eukaryotic initiation factor 4E family in the infection of *Arabidopsis thaliana* by potyviruses," FEBS Letters 579 (2005) 1167-1171.

Robaglia et al., "Translation initiation factors: a weak link in plant RNA virus infection," Trends in Plant Science, vol. 11, No. 1, Jan. 2006, pp. 40-45.

* cited by examiner

PLANT EUKARYOTIC TRANSLATION INITIATION FACTOR 4E

RELATED APPLICATION INFORMATION

This application claims priority under 35 U.S.C. § 371 from PCT Application No. PCT/GB2011/051192, filed Jun. 24, 2011, which claims the benefit of Great Britain Application No. 1010740.7, filed Jun. 25, 2010, the disclosures of which are incorporated by reference herein in their entirety.

The invention relates to plants, and in particular to virus-resistant plants, and to methods of generating such plants. The invention extends to eukaryotic translation initiation factor variants and isoforms thereof, and to nucleic acids involved in the splicing of such variant factors, and uses thereof in methods for producing plants that are resistant to viral infections.

Viruses present a significant problem in agriculture. For example, plant viruses in the family Potyviridae (potyviruses) represent approximately 30% of plant viruses and are capable of infecting more than 30 different families of plants, leading to extensive crop damage and even death. In particular, the Solanaceae, Cucurbitaceae and Fabaceae plant families are especially sensitive to infection by potyviruses. Currently, in contrast to many bacterial or fungal infections, there are few ways to combat viral infections in plants. Due to the increasing size of the international market for plants and seeds, it is becoming more essential for plant breeders to develop plants that are resistant to infection from viruses, for example those from the Potyviridae family.

Upon infection of a plant host, plant viruses use some of the host's endogenous proteins to complete their own life cycle. For example, potyviruses, such as Turnip mosaic virus (TuMV), use plant eukaryotic translation initiation factors to bind plant ribosomes to the viral genomic RNA as a pre-requisite to translating their genomes into various viral proteins, including the viral RNA-dependent RNA polymerase that is essential to produce more copies of the virus. Therefore, defects in the plant eukaryotic translation initiation factors may confer viral resistance in plants. However, since the eukaryotic translation initiation factors are vital to the survival of plants, defects in the eukaryotic translation initiation factors are detrimental to plants, often resulting in plants that are non-viable.

It has been shown in a number of plant-potyvirus interactions that the potyvirus VPg (protein encoded by potyvirus RNA genome) is able to bind to the eIF4E protein and that mutations in members of the eIF4E gene family can confer resistance to potyviruses. Recessive resistance to infections by potyviruses is believed to arise from base changes in the coding region (i.e. the exons) of the genes encoding eIF4E and/or eIF(iso)4E, thereby resulting in eIF4E and/or eIF(iso)4E protein variants.

For example, Turnip mosaic virus (TuMV), which can normally infect *Arabidopsis thaliana*, can no longer infect *A. thaliana* plants that lack a functional eukaryotic translation initiation factor isoform (eIF(iso)4E) protein. Insertional mutagenesis of At.eIF(iso)4E using a defective maize transposon (dSpm) produced a plant line that was able to grow normally, and was resistant to TuMV infection. Additionally, chemically-induced point mutation of the *A. thaliana* eIF(iso)4E gene using ethylmethane sulphonate (EMS) named lsp1 also conferred resistance to TuMV infection.

Although various mechanisms of viral resistance have been found in certain plants, these are mostly specific to virus strains. Dominant plant R genes predominantly provide strain-specific resistance to plant viruses, for example TuRB01 provides resistance to pathotype 1 isolates of TuMV, but is overcome by TuMV isolates belonging to other pathotypes including, 3, 4 and 12. Most examples of recessive resistance associated with mutations in eIF4E and eIF(iso)4E are also strain-specific and mutations in viral VPg and occasionally other viral proteins result in strains able to overcome such resistance.

Therefore, there is a need to induce virus resistance in plants that is not specific to any strains, and thereby confer broad spectrum virus resistance. There are some examples of broad spectrum resistance for some viruses but for most viruses in most crop types, there are no sources of broad spectrum resistance. Additionally, viruses are constantly mutating and genotypes able to overcome strain-specific and broad spectrum resistance are generated in susceptible plants and selected for by the cultivation of resistant plants. Most plant viruses have RNA genomes and RNA is known to have a particularly high mutation rate due to infidelity in the proof-reading mechanism. Consequently, new sources of broad spectrum resistance are required, particularly based on new mechanisms, in order to improve the durability of such resistances.

All previously reported recessive resistance to infection by viruses (such as potyviruses) based on eIF4E or eIF(iso)4E has arisen through base changes in the exons. Such bases changes cause alterations in the sequence of the eIF4E or eIF(iso)4E protein, for example altered amino acid residues in the translated protein, or premature chain termination resulting in a truncated protein. Hence, previous efforts in developing virus-resistant plant species, have focused on generating plant varieties, which harbour mutations in only the exons of either eIF4E or eIF(iso)4E. Surprisingly, however, the inventor has now identified for the first time that plant resistance to viruses, such as potyviruses, may be conferred by plant eIF4E or eIF(iso)4E protein variants that are produced from mis-splicing processes compared to that of the wild-type or native protein.

Accordingly, in a first aspect of the invention, there is provided an isolated plant eukaryotic translation initiation factor 4E (eIF4E) variant, or an isoform thereof (eIF(iso)4E), which is non-functional for a virus, wherein nucleic acid encoding the eIF4E or eIF(iso)4E is mis-spliced.

Previous examples of eIF4E and eIF(iso)4E have all involved mutations in the coding region of the genes. The inventors have now provided the first example of variation in the DNA sequence of an intron inducing virus resistance. Most changes in intron DNA sequence would not be predicted to provide resistance as the introns are spliced from the genes prior to translation and hence do not affect the protein. Additionally, mis-splicing of genes usually results in non-functional proteins, and the lack of the functional protein can be lethal, can lead to reduced fitness, or can have other adverse affects.

The term "eIF4E" is also known as eukaryotic translation initiation factor 4E, which is a key component in the initiation of protein synthesis. As will be known to the skilled technician, in plants, eIF4E forms a complex eIF4F (consisting of eIF4E and eIF4G). The precise biochemical role of a plant eIF4E protein in virus infection has yet to be identified. However, not wishing to be bound to any theory, the plant eIF4E may be capable of binding to the 5' cap structure (or a mimic) of the viral RNA, or the plant eIF4E may interact with the viral RNA directly. Alternatively, eIF4E may be involved in the cell-to-cell movement of the infecting virus in the host plant.

The term "eIF(iso)4E" refers to an isoform of eIF4E, and eIF(iso)4E has a similar function as eIF4E. eIF4E and eIF(iso)4E proteins from *Arabidopsis thaliana* are 44%-49% identical at the amino acid level. This is similar to values found for *Brassica rapa* line R-o-18 (47-50% identity) and *Brassica rapa* line Chiifu (43-50% identity).

The virus life cycle is totally dependent on using the host plant's translation machinery to turn viral nucleic acid into proteins. Without the viral proteins produced by the host translation machinery, no viral replicase protein is produced and so no more copies of the virus are made either. A number of viruses have been shown to be dependent on the host plant's translation complex and virus interactions with the plant eIF4E and/or eIF(iso)4E proteins have been demonstrated (the version used depends on the particular combination of virus species and plant species).

The skilled person will appreciate that mis-splicing can produce the eIF4E or eIF(iso)4E variant of the first aspect, which can therefore be described as being an alternatively spliced variant, compared to the wild-type or native eIF4E or eIF(iso)4E proteins. The genomic sequence of a gene, such as that encoding eIF4E or eIF(iso)4E, comprises coding regions (i.e. exons) and non-coding regions (i.e. introns). The introns and exons are transcribed into RNA termed "primary transcript, precursor to mRNA" (or "pre-mRNA"). The introns must be removed from the pre-mRNA so that the native protein encoded by the exons can be produced. The term "native protein" can mean the naturally occurring, wild-type or functional protein.

The removal of the introns from the pre-mRNA and subsequent ligation of the exons to each other is carried out in the splicing process. The splicing process usually consists of a series of reactions, mediated by splicing factors, which is carried out on the RNA after transcription, but before translation. Thus, a "pre-mRNA" is an RNA molecule which contains both exons and intron(s), and an "mRNA" is an RNA in which the intron(s) have been removed and the exons have been joined together sequentially so that the protein can then be translated therefrom by the ribosomes.

Introns are defined by a set of "splice elements" which are relatively short, conserved RNA segments which bind the various splicing factors that carry out the splicing reactions. Thus, each intron is defined by a 5' splice site, a 3' splice site, and a branch point situated there between.

The inventor has found that the protein variant of the first aspect may be caused by modifications in the splice element of the native DNA and/or pre-mRNA of eIF4E or eIF(iso)4E, which create a new, aberrant, splice element (compared to the wild-type). Therefore, in an embodiment of the invention, the mis-spliced gene encoding eIF4E or eIF(iso)4E may arise from a modification in a splice element, thereby producing an aberrant splice element. The aberrant splice element may cause altered splice patterns of the eIF4E or eIF(iso)4E pre-mRNA, giving rise to altered mRNA. Preferably, the resulting eIF4E protein variant or eIF(iso)4E protein variant of the first aspect is not functional for the virus in a plant, such that the plant is substantially resistant to viral infection.

The inventor has demonstrated that alterations in an intron of the gene encoding eIF4E or eIF(iso)4E (rather than in an exon) result in mis-splicing occurring, which results in a eIF4E variant or eIF(iso)4E variant protein being produced, which is non-functional for a virus, and thus confers virus resistance when present in a plant.

In one embodiment, the aberrant splice element may alter the native splice site at the 5'- or 3'-end of the intron (i.e. at the 5' native splice site or at the 3' native splice site of the intron), which creates a new, aberrant, splice site. It would be appreciated that the difference between the genomic DNA sequence and the sequence of mature message RNA defines the introns. The 5' and 3' ends of the introns define the native splice sites of a gene.

The aberrant splice site may be upstream or downstream of the native splice site. It would be appreciated by the skilled technician that the term "upstream" means towards the 5' end of the DNA or pre-mRNA molecule and may be denoted by the symbol "−". It would also be appreciated by the skilled technician that the term "downstream" means towards the 3' end of the DNA or pre-mRNA molecule, and may be denoted by the symbol "+". Hence, in an embodiment where the aberrant splice site may be 10 nucleotides upstream from the 5' native splice site of intron 1, the aberrant splice site may also be referred to as "−10 bp relative to the 5' splice site of intron 1".

In embodiments where the aberrant splice site is upstream of the 5' native splice site of an intron, some of the exon that is upstream of the intron may be excised during the splicing process. Therefore, the resulting mRNA may lack nucleotides of the excised exon. In embodiments where the aberrant splice site is downstream of the 5' native splice site of an intron, some of the intron may be retained during the splice event. Therefore, the resulting mRNA may comprise nucleotides of the retained intron.

In embodiments where the aberrant splice site is downstream of the 3' native splice site of an intron, some of the exon downstream of the intron may be excised during the splicing process. Therefore, the resulting mRNA may lack nucleotides of the excised exon. In embodiments where the aberrant splice site is upstream of the 3' native splice site of an intron, some, or all of the intron may be retained during the splice event. Therefore, the resulting mRNA may contain the retained intron nucleotides.

In an alternative embodiment, the altered splice pattern may comprise retaining at least one intron. The resultant mRNA molecule (i.e. mRNA variant) may therefore contain RNA sequence that corresponds to the retained intron or introns, and may be larger than the native mRNA molecule.

The amino acid sequence translated from the retained at least one intron, or part thereof may comprise a stop codon. The resulting protein (i.e. protein variant) may not be translated beyond the first stop codon and, hence, the protein variant may be smaller in size compared to the native protein. The stop codon that is introduced by the retained intron may be referred to as a premature stop codon because it causes translation of the mRNA to cease prematurely (the first wild-type stop codon of the gene being located further downstream). Therefore, the protein variant may have lack of function or an altered function compared to the wild-type or the native protein. The protein variant may be non-functional for a virus.

The codon reading frame of the retained at least one intron, or part thereof, may be in-frame or out-of-frame with the coding reading frame of the neighbouring exon(s). The resulting mRNA may encode an altered amino acid sequence, and hence, produce a protein variant. The protein variant may have lack of function or an altered function compared to the wild type or the native protein. The protein variant may be non-functional for a virus.

In an embodiment where the codon reading frame of the retained at least one intron, or part thereof, is out-of-frame with that of the neighbouring exon(s), the resulting protein (i.e. protein variant) may contain altered amino acid sequences may be truncated due to a premature stop codon. The resultant protein variant may have lack of function or an altered function compared to the wild type or the native protein. The protein variant may be non-functional for a virus.

In an embodiment where at least one exon, or a part thereof, is excised, the resulting mRNA may encode an altered amino acid sequence, and hence, produce a protein variant. The altered amino acid sequence may contain a premature stop codon. The protein variant may have lack of function, or an altered function compared to the wild type or the native protein. The protein variant may be non-functional for a virus.

The altered function of the eIF4E variant or eIF(iso)4E variant may comprise a decrease in its activity for translation initiation. When the mis-splicing occurs in intron 1, this may result in extremely truncated versions of the protein, or versions where most of the protein is completely different to functional versions. Not bound by theory, this may have a number of consequences, as it is highly unlikely to bind to other components of the eukaryotic initiation complex, particularly eIF4G or eIF(iso)4G and also unlikely to bind to the viral protein VPg, or messenger RNA cap. This will result in lack of translation of messenger RNA and/or viral RNA.

The inventor has carried out his experiments using *Brassica rapa* as a plant model, and has surprisingly found that *B. rapa* contains three eIF(iso)4E loci, and thus, has three protein isoforms of eIF(iso)4E, the protein isoforms being denoted eIF(iso)4E.a, eIF(iso)4E.b and eIF(iso)4E.c. He therefore investigated eIF(iso)4E.a in two plant lines. The first plant line, referred to herein as "R-o-18", is sensitive to infection with a virus (i.e. Turnip Mosaic virus, TuMV), and the second plant line, referred to herein as "RLR22", is resistant to viral infection. The inventor has determined the genomic, mRNA and polypeptide sequences for the eIF(iso)4E.a isoform of *B. rapa*, as discussed below.

The genomic DNA sequence encoding the native or wild type *Brassica rapa* eIF(iso)4E.a isoform, BraA.eIF(iso)4E.a, in line R-o-18 (sensitive to viral infection), is provided herein as SEQ ID No. 1, as follows:

```
                                                                SEQ ID No: 1
ATGGCGACAGAGGATGTGAACGAAGCCCTTGCGGCGGCGGAAGTACCGGCAACAGAGACGACGGAGAAGC

AGCCTGCTCACAAGCTCGAAAGAAAGTGGAGTTTCTGGTTCGATAACCAATCCAAACCAAAGCAAGGCGC

CGCCTGGGGAGCCTCCCTTCGCAAAGCCTATACCTTCGACACCGTCCAAGACTTCTGGGGGTTTGTTTGT

CTTCTCCTTTTATTTATTGTTAGCGATCTGTAAAGCTAGATCTTCTTTTGCAGTTTGCACGAGACTATAT

TCATCCCTAGCAAACTGACGCCGAATGCTGAAATTCACATGTTCAAAGCTGGTGTTGAGCCTAAGTGGGA

AGATCCTGAGTGTGCTAATGGGGAAAGTGGACTTATGTTGTCACCTCCAACCGCAAGCCTGCTTTAGAC

AAGGCTTGGCTTGAAACTGTACTCCTCTTCTACCTCTCCTCCTTTTTTCTTTTTTTTTGCATCTGGTAAT

GACATGTTTTCTCTGCCAGTTGATGGCTCTTGTCGGAGAGCAATTTGATGAGGCTGATGAGATTTGTGGC

GTGGTTGCTAGTGTGCGCCCAAAGCAGGACAAGCTCTCCTTGTGGACAAGGACCAAATCTAATGAAGCTG

TTCTGGTATGATGCTTGTCTTCTCTCACTATGTACCTTTGGTGTTGTTTGATAACTGTTTTCTTCTACTT

GTTATCCGTTGCGATGTCCCATTATTGTTTGATTATCCTGTTCCAATTTTTTTGTATTGCGTACTGGTGG

TTTACGAAGAAGTGTTCTTGTACAATATGTTAGCGTTGTTGAATGTGTTAATTGCTTACTATAGTAAAAC

AGTTTAAGCTGTTGACTATGTTAATATTCTCTTCGATACACACACTTAGAATGGATAACTACCTTGTTTC

TTTATCCTTTGGAGTTTCACCAGCTTATTATCGATCGAGATACTCCTTCTGATTTGAATTACCATTCAAG

ATTAATATTTATATATATTGAAAGTATATGTTTGTTTAACGATATATCTATTAGGCTTGCTTTTTTTAGT

TCATTCGCAGTATAAACGTAGCTCTATTTATTAGAGGCTTCTCTTTAGAACTTGGCAGTAATGTAATATG

TCGAAGTGTGGTTTATGAATCTGGTTGATGATATTACTAATTTTTTTGTTTGTTATTGTAAATCCAGATG

GGTATTGGGAAGAAGTGGAAGGAGATACTTGATGTCACCGACAAGATAACTTTCACTAACCATGTAACTT

AACTTTCTCCACATAGAGGCTAATTATCTTTTGTTCTTCTTACGTGGCTTACTAAAATGTGGTCTACTTA

TATATATAGGATGATTCTAGAAGAACTAGGTTCACTGTCTGA
```

SEQ ID No: 1 shows exons 1 to 5, with the introns being represented in bold.

The mRNA sequence of the native or wild type BraA.eIF(iso)4E.a in line R-o-18 (sensitive to viral infection), is provided herein as SEQ ID No. 2, as follows:

```
                                                                SEQ ID No: 2
AUGGCGACAGAGGAUGUGAACGAAGCCCUUGCGGCGGCGGAAGUACCGGCAACAGAGACGACGGAGAAGC

AGCCUGCUCACAAGCUCGAAAGAAAGUGGAGUUUCUGGUUCGAUAACCAAUCCAAACCAAAGCAAGGCGC

CGCCUGGGGAGCCUCCCUUCGCAAAGCCUAUACCUUCGACACCGUCCAAGACUUCUGGGGUUUGCACGAG
```

```
ACUAUAUUCAUCCCUAGCAAACUGACGCCGAAUGCUGAAAUUCACAUGUUCAAAGCUGGUGUUGAGCCUA

AGUGGGAAGAUCCUGAGUGUGCUAAUGGGGGAAAGUGGACUUAUGUUGUCACCUCCAACCGCAAGCCUGC

UUUAGACAAGGCUUGGCUUGAAACUUUGAUGGCUCUUGUCGGAGAGCAAUUUGAUGAGGCUGAUGAGAUU

UGUGGCGUGGUUGCUAGUGUGCGCCCAAAGCAGGACAAGCUCUCCUUGUGGACAAGGACCAAAUCUAAUG

AAGCUGUUCUGAUGGGUAUUGGGAAGAAGUGGAAGGAGAUACUUGAUGUCACCGACAAGAUAACUUUCAC

UAACCAUGAUGAUUCUAGAAGAACUAGGUUCACUGUCUGA
```

FIG. 3 illustrates schematically that the exons of BraA.eIF(iso)4E.a are ligated together to form the mRNA of SEQ ID No: 2.

The polypeptide sequence of the native or wild type BraA.eIF(iso)4E.a in line R-o-18 (sensitive to viral infection), is provided herein as SEQ ID No. 3, as follows:

```
                                                                SEQ ID No: 3
MATEDVNEALAAAEVPATETTEKQPAHKLERKWSFWFDNQSKPKQGAAWGASLRKAYTFDTVQDFWGLHE

TIFIPSKLTPNAEIHMFKAGVEPKWEDPECANGGKWTYVVTSNRKPALDKAWLETLMALVGEQFDEADEI

CGVVASVRPKQDKLSLWTRTKSNEAVLMGIGKKWKEILDVTDKITFTNHDDSRRTRFTV.
```

The genomic DNA sequence encoding the *Brassica raga* eIF(iso)4E.a isoform, BraA.eIF(iso)4E.a variant, in line RLR22 (resistant to viral infection), is provided herein as SEQ ID No. 4, as follows:

tion or "indel". The inventor has surprisingly observed that the DNA sequence represented as SEQ ID No. 4, in some embodiments, can give rise to several different forms of mRNA sequence, each of which may produce the variant of the eIF4E or eIF(iso)4E protein of the first aspect. The inventor has named the allele (BraA.eIF(iso)4E.a) from the virus-resistant line (RLR22) "retr01", which is believed to be recessive.

```
                                                                SEQ ID No: 4
ATGGCGACAGAGGATGTGAACGAAGCCCTTGCGGCGGCGGAAGTACCGGCAACAGAGACGACGGAGAAGC

AGCCTGCTGACAAGCTCGAAAGAAAGTGGAGTTTCTGGTTCGATAACCAATCCAAACCAAAGCAAGGCGC

CGCCTGGGGAGCCTCCCTTCGCAAAGCCTATACCTTCGACACCGTCCAAGACTTCTGGGGGGTTTGTTTG

TCTTCTCCTTTTACTTATTGTTAGCGATCTGTAAAGCTAGATCTTCTTTTGCAGTTTGCACGAGACTATA

TTCATCCCTAGCAAACTGACGCCGAATGCTGAAATTCACATGTTCAAAGCTGGTGTTGAGCCTAAGTGGG

AAGATCCTGAGTGTGCTAATGGCGGAAAGTGGACTTTTGTTGTTACCTCCAACCGCAAGCCTGCTTTAGA

CAAGGCTTGGCTTGAAACTGTACTCATCTTCTACCTCTCCTCTTTTTTTTTTAATAGTTTAGACAATTT

TGCATCTGGTAATGACATGTTTTATCTGCCAGTTGATGGCTCTTGTCGGAGAGCAATTTGATGAGGCTGA

TGAGATCTGTGGGGTGGTTGCTAGTGTGCGCCCAAAGCAGGACAAGCTCTCCTTGTGGACAAGGACCAAA

TCTAATGAAGCTGTTCTGGTATGATGCTTCTCTTCTCTCACTATGTACCTTTGGTGTTGTTTTCTTCTAC

TTGTTATCCGTTGCGATGTCCCATTATTGTTTGATTATCCTGTTCCAATTTTTCTGTTTTGCGTACTGGT

GGTTTACGAAGAAGTATGCTTGTACAATATGTTAGCGTTGTTGAATGTGTTAATTGCTTACTATAGTAAA

ACAGTTTAAGCTGTTGACTATGTTAATATTCTCTTCGATACACACACTTAGAATGGATAACTACCTTGTT

TCTTTATCCTTTGGAGTTTCACCAGCTTAATATATATTGAAAGTATATGTTTGTTCAACGATATATCTAT

TAGGCTTGCTTTTTTTAGTTCATTCGCAGTATAAACATAGCTCTATTTATTAGAGGCCATCTCTTTAGAA

CTTGGCAGTACTGTAATATGTCGAAGTGTGGTTTATGAATCTGGCTGATGATATTACTACTTTGTTGTTT

GTTATTGTAAATCCAGATGGGTATTGGGAAGAAGTGGAAGGAGATACTTGATGTCACCGACAAGATAACT

TTCACTAACCATGTAACTTAACTTTCTCCACATAGAGGCTAATTATCTTTTGTTCTTCTTACGTGGCTTA

CTAAAATGTGGTCTACTTATATATATAGGATGATTCTAGAAGAACTCGGTTCACTGTCTGA
```

SEQ ID No: 4 shows the introns being represented in bold, and a guanine insertion at position +1 of the 5' splice site of intron 1 (underlined in the sequence above). This mutation is referred to herein as "insertion/deletion" muta- A first embodiment of an mRNA sequence of BraA.eIF(iso)4E.a variant in line RLR22 (resistant to viral infection), is provided herein as SEQ ID No. 5, as follows:

```
                                                                SEQ ID No: 5
AUGGCGACAGAGGAUGUGAACGAAGCCCUUGCGGCGGCGGAAGUACCGGCAACAGAGACGACGGAGAAGC

AGCCUGCUGACAAGCUCGAAAGAAAGUGGAGUUUCUGGUUCGAUAACCAAUCCAAACCAAAGCAAGGCGC

CGCCUGGGGAGCCUCCCUUCGCAAAGCCUAUACCUUCGACACCGUCCAAGACUUCUGGGGGGUUUGUUUG

UCUUCUCCUUUUACUUAUUGUUAGCGAUCUGUAAAGCUAGAUCUUCUUUUGCAGUUUGCACGAGACUAUA

UUCAUCCCUAGCAAACUGACGCCGAAUGCUGAAAUUCACAUGUUCAAAGCUGGUGUUGAGCCUAAGUGGG

AAGAUCCUGAGUGUGCUAAUGGCGGAAAGUGGACUUUUGUUGUUACCUCCAACCGCAAGCCUGCUUUAGA

CAAGGCUUGGCUUGAAACUUUGAUGGCUCUUGUCGGAGAGCAAUUUGAUGAGGCUGAUGAGAUCUGUGGG

GUGGUUGCUAGUGUGCGCCCAAAGCAGGACAAGCUCUCCUUGUGGACAAGGACCAAAUCUAAUGAAGCUG

UUCUGAUGGGUAUUGGGAAGAAGUGGAAGGAGAUACUUGAUGUCACCGACAAGAUAACUUUCACUAACCA

UGAUGAUUCUAGAAGAACUCGGUUCACUGUCUGA
```

As can be seen, the effect of the nucleic acid modification in SEQ ID No. 4 (i.e. containing the guanine insertion at position +1 of the 5' splice site of intron 1) is that the resultant mRNA shown in SEQ ID No: 5 contains RNA sequence that corresponds to intron 1 which is fully retained, and which is represented in bold. FIG. 4 illustrates schematically that an altered splice pattern of eIF4E DNA or pre-mRNA resulting in the mRNA of SEQ ID No: 5.

The polypeptide sequence corresponding to the first embodiment of mRNA (i.e. SEQ ID No: 5) of BraA.eIF(iso)4E.a variant in line RLR22, is provided herein as SEQ ID No. 6, as follows:

```
                                                                SEQ ID No: 6
MATEDVNEALAAAEVPATETTEKQPADKLERKWSFWFDNQSKPKQGAAWGASLRKAYTFDTVQDFWGVCL

SSPFTYC.RSVKLDLLLQFARDYIHP.QTDAEC.NSHVQSWC.A.VGRS.VC.WRKVDFCCYLQPQACFR

QGLA.NFDGSCRRAI..G..DLWGGC.CAPKAGQALLVDKDQI..SCSDGYWEEVEGDT.CHRQDNFH.P

..F.KNSVHCL
```

In SEQ ID No. 6, chain termination is indicated by a ".". As can be seen, translation of the mRNA shown in SEQ ID No: 5, having the whole of intron 1 retained, results in a first premature stop codon at position 88, such that a truncated eIF(iso)4E protein is produced.

A second embodiment of an mRNA sequence of BraA.eIF (iso)4E.a variant in line RLR22 (resistant to viral infection), is provided herein as SEQ ID No. 7, as follows:

The mRNA variant shown in SEQ ID No: 7 results from an altered 3' splice site of intron 1. The altered splice site is at position +48 relative to the 5' end of intron 1 (i.e. 15 bp upstream of the native 3' splice site of intron 1). The retained intron sequence (15 nucleotides) is represented in bold. FIG. 5 illustrates this splice event schematically.

The polypeptide sequence corresponding to the second embodiment of mRNA variant (i.e. SEQ ID No: 7) of BraA.eIF(iso)4E.a variant in line RLR22, is provided herein as SEQ ID No. 8, as follows:

```
                                                                SEQ ID No: 7
AUGGCGACAGAGGAUGUGAACGAAGCCCUUGCGGCGGCGGAAGUACCGGCAACAGAGACGACGGAGAAGC

AGCCUGCUGACAAGCUCGAAAGAAAGUGGAGUUUCUGGUUCGAUAACCAAUCCAAACCAAAGCAAGGCGC

CGCCUGGGGAGCCUCCCUUCGCAAAGCCUAUACCUUCGACACCGUCCAAGACUUCUGGGGGAUCUUCUUU

UGCAGUUUGCACGAGACUAUAUUCAUCCCUAGCAAACUGACGCCGAAUGCUGAAAUUCACAUGUUCAAAG

CUGGUGUUGAGCCUAAGUGGGAAGAUCCUGAGUGUGCUAAUGGCGGAAAGUGGACUUUUGUUGUUACCUC

CAACCGCAAGCCUGCUUUAGACAAGGCUUGGCUUGAAACUUUGAUGGCUCUUGUCGGAGAGCAAUUUGAU

GAGGCUGAUGAGAUCUGUGGGGUGGUUGCUAGUGUGCGCCCAAAGCAGGACAAGCUCUCCUUGUGGACAA

GGACCAAAUCUAAUGAAGCUGUUCUGAUGGGUAUUGGGAAGAAGUGGAAGGAGAUACUUGAUGUCACCGA

CAAGAUAACUUUCACUAACCAUGAUGAUUCUAGAAGAACUCGGUUCACUGUCUGA
```

SEQ ID No: 8
MATEDVNEALAAAEVPATETTEKQPADKLERKWSFWFDNQSKPKQGAAWGASLRKAYTFDTVQDFWGIFF
CSLHETIFIPSKLTPNAEIHMFKAGVEPKWEDPECANGGKWTFVVTSNRKPALDKAWLETLMALVGEQFD
EADEICGVVASVRPKQDKLSLWTRTKSNEAVLMGIGKKWKEILDVTDKITFTNHDDSRRTRFTV.

In SEQ ID No. 8, five new amino acid residues (i.e. IFFCS) are translated as a result of the nucleic modification and are shown in bold. As can be seen, translation of the mRNA shown in SEQ ID No: 7 having part of the intron retained does not result in a frameshift, but the elongated protein may be non-functional for the virus.

A third embodiment of an mRNA sequence of BraA.eIF(iso)4E.a variant in line RLR22 (resistant to viral infection), is provided herein as SEQ ID No. 9, as follows:

eIF4E or eIF(iso)4E protein, may comprise a sequence substantially as set out in SEQ ID No: 4, 5, 7 or 9, or a variant or fragment thereof.

In view of the above, it will be appreciated that the mis-splicing of the nucleic acid encoding the eIF4E or eIF(iso)4E protein variant of the first aspect may be caused by a modification in said nucleic acid sequence. It is preferred that the modification occurs in a non-coding region of the gene. The modification may be located in a splice SEQ ID No: 9
AUGGCGACAGAGGAUGUGAACGAAGCCCUUGCGGCGGCGGAAGUACCGGCAACAGAGACGACGGAGAAGC
AGCCUGCUGACAAGCUCGAAAGAAAGUGGAGUUUCUGGUUCGAUAACCAAUCCAAACCAAAGCAAGGCGC
CGCCUGGGGAGCCUCCCUUCGCAAAGCCUAUACCUUCGACACCGUCCAAGACUUCUGΔUUUGCACGAGAC
UAUAUUCAUCCCUAGCAAACUGACGCCGAAUGCUGAAAUUCACAUGUUCAAAGCUGGUGUUGAGCCUAAG
UGGGAAGAUCCUGAGUGUGCUAAUGGCGGAAAGUGGACUUUUGUUGUUACCUCCAACCGCAAGCCUGCUU
UAGACAAGGCUUGGCUUGAAACUUUGAUGGCUCUUGUCGGAGAGCAAUUUGAUGAGGCUGAUGAGAUCUG
UGGGGUGGUUGCUAGUGUGCGCCCAAAGCAGGACAAGCUCUCCUUGUGGACAAGGACCAAAUCUAAUGAA
GCUGUUCUGAUGGGUAUUGGGAAGAAGUGGAAGGAGAUACUUGAUGUCACCGACAAGAUAACUUUCACUA
ACCAUGAUGAUUCUAGAAGAACUCGGUUCACUGUCUGA The mRNA variant shown in SEQ ID No: 9 results from an altered 5' splice site of intron 1. The altered splice site is at position-3 (i.e. 3 bp upstream) relative to the 5' native splice site of intron 1. The excised exon sequence (3 nucleotides) is represented by the symbol "Δ". FIG. 6 illustrates this splice event schematically.

The polypeptide sequence corresponding to the third embodiment of mRNA (i.e. SEQ ID No. 9) of BraA.eIF(iso)4E.a variant in line RLR22, is provided herein as SEQ ID No. 10, as follows:

element in the nucleic acid sequence encoding eIF4E or eIF(iso)4E protein to produce an aberrant splice element. The modification may be present upstream or downstream of the exon-intron junction or native splice site. Preferably, the modification is present between the position −10 and +10 of the native splice site. More preferably, the modification is present between the position −5 and +5 of the native splice site. Most preferably, the modification is present at position −1 to +1 of the native splice site. The native splice site may be at or towards the 5'- or 3'-end of an intron.

SEQ ID No: 10
MATEDVNEALAAAEVPATETTEKQPADKLERKWSFWFDNQSKPKQGAAWGASLRKAYTFDTVQDFCLHET
IFIPSKLTPNAEIHMFKAGVEPKWEDPECANGGKWTFVVTSNRKPALDKAWLETLMALVGEQFDEADEIC
GVVASVRPKQDKLSLWTRTKSNEAVLMGIGKKWKEILDVTDKITFTNHDDSRRTRFTV.

In SEQ ID No. 10, a new amino acid residue (i.e. C) is translated as a result of the nucleic modification and is shown in bold. As can be seen, translation of the mRNA shown in SEQ ID No: 9 having part of the intron retained did not result in a frameshift. Comparing SEQ ID No. 9 with SEQ ID No. 3, amino acids: phenylalanine(F)-tryptophan (W)-glycine(G) at positions 75-77 have been replaced by cysteine(C). Having lost one amino acid and had another substituted may result in a protein that is non-functional for the virus.

Accordingly, the eIF4E or eIF(iso)4E protein variant of the first aspect may comprise an amino acid sequence substantially as set out in SEQ ID No: 6, 8 or 10, or a variant or fragment thereof. The nucleic acid, which encodes the The splice element may comprise a 3' splice site, a 5' splice site and a branch site, all of which are required for accurate removal of the intron during production of mature message RNA. Modifications in one, or more of these components may result in failure to remove some, or all of the intron, or removal of exon sequence. This in turn results in truncated or elongated proteins which are highly unlikely to be functional or would be less functional than the native protein.

The modification may be located in an intron in the nucleic acid sequence encoding eIF4E or eIF(iso)4E protein. The modification may be in intron 1, 2, 3 or 4 of the nucleic acid sequence encoding eIF4E or eIF(iso)4E proteins. Intron 1 corresponds to bases 201 to 263 of SEQ ID No. 1, intron 2 corresponds to bases 439 to 509 of SEQ ID No. 1, intron 3 corresponds to bases 636 to 1187 of SEQ ID No. 1 and intron 4 corresponds to bases 1254 to 1339 of SEQ ID No. 1

Preferably, the modification is in intron 1 of the nucleic acid sequence encoding eIF4E or eIF(iso)4E protein.

The modification may comprise an insertion, deletion, substitution or any combination of these, of at least one nucleic acid base anywhere in the nucleic acid sequence encoding eIF4E or eIF(iso)4E protein, preferably in an intron, more preferably in intron 1. The insertion may be a purine (adenine or guanine) or a pyrimidine (cytosine or thymine). Preferably, the modification comprises a guanine insertion. The modification may result in a frameshift of the codon reading frame relative to that of the native protein. The modification may result in the formation of a premature stop codon. The modification may result in no frameshift, or no premature stop codon, but with the addition or deletion of amino acids.

Preferably, the modification comprises an insertion at position 201 of SEQ ID No. 1, which insertion is preferably a guanine.

The inventor believes that it may be possible to modify the plant genome to produce mutations that would result in mis-splicing of eIF4E and/or eIF(iso)4E, or other proteins essential for the completion of virus life-cycles by artificial means known in the art. The artificial means may include inducing/promoting recombination, site-directed mutagenesis through a number of means, Targeted Induced Local Lesions in Genomes (TILLING), or other means known in the art.

The inventor has found that the eIF4E or eIF(iso)4E variant protein of the first aspect is non-functional for Turnip mosaic virus (TuMV). However, the inventor believes that the eIF4E or eIF(iso)4E protein of the first aspect is non-functional for a wide variety of viruses, which can otherwise infect plants. Thus, the eIF4E or eIF(iso)4E may be non-functional for any plant viruses that are dependent on them for completion of their life cycle.

However, it is preferred that the variant eIF4E or eIF(iso)4E is non-functional for any plant virus, in the family Potyviridae. Examples of suitable potyviruses for which the eIF4E or eIF(iso)4E may be non-functional include Pepper veinal mottle virus (PVMP), Bean common mosaic virus (BCMV), Potato virus Y (PVY), or Azukinin mosaic virus (AzMV), or any other virus that is dependent on eIF4E and/or eIF(iso)4E.

As described herein, the eIF4E or eIF(iso)4E protein of the first aspect is non-functional for a range of viruses in *Brassica rapa*. However, the inventor believes that the eIF4E or eIF(iso)4E protein of the first aspect is non-functional for viruses in a wide range of different plant species. Thus, the eIF4E or eIF(iso)4E may be non-functional for a virus in a plant of the family Solanaceae, such as potato (all species), tomato, pepper or egg plant, Cucurbits, such as melons, squash and cucumbers, Cruciferous crops, particularly *Brassica napus* such as oilseed rape, *Brassica rapa* such as Chinese cabbage, and even more particularly *Brassica oleracea* such as broccoli, cauliflower, cabbage, savoy cabbage, Brussels sprouts, red cabbage, and the like etc., Fabaceae peas, beans, pulses etc. and also any monocotyledonous crops, including rice, maize, wheat, barley etc. In one preferred embodiment, the plant may be *Brassica* spp, preferably *B. rapa* and/or *Brassica oleracea*.

In a second aspect, there is provided an isolated nucleic acid sequence encoding an alternatively spliced variant of a plant eukaryotic translation initiation factor 4E (eIF4E), or an isoform thereof (eIF(iso)4E), wherein the nucleic acid sequence is mis-spliced such that the eIF4E or eIF(iso)4E is non-functional for a virus.

The isolated nucleic acid sequence of the second aspect may comprise DNA, cDNA, RNA or mRNA.

The nucleic acid sequence may comprise a nucleotide sequence substantially as set out in any one of SEQ ID No: 4, 5, 7 or 9, or a variant or fragment thereof. The eIF4E or eIF(iso)4E encoded by the nucleic acid sequence may comprise an amino acid sequence substantially as set out in any one of SEQ ID No: 6, 8 or 10, or a variant or fragment thereof.

In a third aspect, there is provided a recombinant vector comprising the nucleic acid sequence of the second aspect.

The recombinant vector may be a plasmid, cosmid or phage. Such recombinant vectors are highly useful for transforming host cells with the nucleic acid molecules of the second aspect. The skilled technician will appreciate that genetic constructs of the invention may be combined with many types of backbone vector for expression purposes. The backbone vector may be a binary vector, for example one which can replicate in both *E. coli* and *Agrobacterium tumefaciens*. For example, a suitable vector may be a pBIN plasmid, such as pBIN19.

Recombinant vectors may include a variety of other functional elements in addition to the nucleic acid sequence of the invention, including a promoter. For instance, the recombinant vector may be designed such that it autonomously replicates in the cytosol of a host cell, which may be a plant cell. In this case, elements which induce or regulate DNA replication may be required in the recombinant vector. Alternatively, the recombinant vector may be designed such that it integrates into the genome of a host cell. In this case, DNA sequences which favour targeted integration (e.g. by homologous recombination) are envisaged.

The recombinant vector may also comprise DNA coding for a gene that may be used as a selectable marker in the cloning process, i.e. to enable selection of cells that have been transfected or transformed, and to enable the selection of cells harbouring vectors incorporating heterologous DNA. Alternatively, the selectable marker gene may be in a different vector to be used simultaneously with vector containing the gene of interest. The vector may also comprise DNA involved with regulating expression of the coding sequence, or for targeting the expressed polypeptide to a certain part of the host cell, e.g. the chloroplast. Hence, the vector of the third aspect may comprise at least one additional element selected from a group consisting of: a selectable marker gene (e.g. an antibiotic resistance gene); a polypeptide termination signal; and a protein targeting sequence (e.g. a chloroplast transit peptide).

Examples of suitable marker genes include antibiotic resistance genes such as those conferring resistance to Kanamycin, Geneticin (G418) and Hygromycin (npt-II, hyg-B); herbicide resistance genes, such as those conferring resistance to phosphinothricin and sulphonamide based herbicides (bar and sul respectively; EP-A-242246, EP-A-0249637); and screenable markers such as beta-glucuronidase (GB2197653), luciferase and green fluorescent protein (GFP).

The marker gene may be controlled by a second promoter, which allows expression in cells, which may or may not be in the seed, thereby allowing the selection of cells or tissue containing the marker at any stage of development of the plant. Suitable second promoters are the promoter of nopaline synthase gene of *Agrobacterium* and the promoter derived from the gene which encodes the 35S cauliflower mosaic virus (CaMV) transcript. However, any other suitable second promoter may be used.

Various embodiments of the vector of the invention may be prepared using a suitable cloning procedure, and which may be summarised as follows.

In a fourth aspect, there is provided a host cell comprising the vector of the third aspect.

The host cell may be a plant cell. Alternatively, the host cell may be a bacterium or a virus. The vector may be transformed into the host cell using techniques known to the skilled technician.

It would be appreciated that molecular techniques required to introduce the vector of the third aspect into a plant are known in the art, and may be found in textbooks such as Sambrook et al.

The inventor has found that it is possible to detect plants, which are resistant to infection from viruses.

In a fifth aspect of the invention, there is provided a method for detecting, in a test plant, the presence of a plant eukaryotic translation initiation factor 4E (eIF4E) variant, or an isoform thereof (eIF(iso)4E), which is non-functional for a virus, wherein nucleic acid encoding the eIF4E or eIF(iso)4E is mis-spliced, the method comprising the steps of:
   (i) isolating RNA from a test plant;
   (ii) producing cDNA from the RNA isolated in step (i) using primers specific for eIF4E or eIF(iso)4E;
   (iii) determining the sequence of the cDNA produced in step (ii); and
   (iv) comparing the cDNA sequence determined in step (iii) with the cDNA sequence of wild-type eIF4E or eIF(iso)4E,
   wherein a variation in the sequence of step (iii) compared to the wild-type sequence indicates that the nucleic acid encoding the eIF4E or eIF(iso)4E in the test plant is mis-spliced and is a variant of eIF4E or eIF(iso)4E.

It will be appreciated that the detection steps of (i) to (iv) involve molecular techniques that are known in the art, such as in Sambrook et al. The method may comprise a step of obtaining a sample from the test plant, from the RNA may be isolated, preferably mRNA. The cDNA may be obtained by reverse transcription polymerase chain reaction (RT-PCR) of eIF4E and/or eIF(iso)4E RNA utilising primers complementary to these genes. It would be appreciated that the skilled technician would employ techniques known in the art to design the location of the RT-PCR primers. Preferably, the RT-PCR primers are designed such that the resulting amplified product encompasses the complete coding region of the eIF4E or eIF(iso)4E gene.

For example, the reverse transcription primer may be selected from a group consisting of:

```
                                          (SEQ ID No. 13)
AAAAAGCAGGCT CGAGGCGACAGAGGATG;

(SEQ ID No. 14)
AGAAAGCTGGGT TCAGACAGTGAACCTAGTTCTTC;
and (SEQ ID No. 15)
AGAAAGCTGGGT TCAGACAGTGAACCGAGTTCTTC.
```

The method of the fifth aspect may further comprise a step of identifying the modification in the plant genome that causes mis-splicing of eIF4E or eIF(iso)4E, wherein said identification step may comprise breeding the test plant such that it is homozygous for eIF4E or eIF(iso)4E gene. The method may comprise determining the genomic sequence of said gene. The method may comprise comparing the determined genomic sequence with the genomic sequence of wild type eIF4E or eIF(iso)4E to identify the modification that causes mis-splicing of eIF4E or eIF(iso)4E.

In an embodiment where the test plant is heterozygous for eIF4E or eIF(iso)4E, homozygosity may obtained by self-crossing the test plant.

The inventor has found that it is possible to generate and select plants, which are resistant to infection from viruses.

Thus, in a sixth aspect, there is provided a method for selecting a virus-resistant plant, the method comprising detecting, in a test plant, the presence of:—
   (i) a plant eukaryotic initiation factor 4E (eIF4E) variant or an isoform thereof (eIF(iso)4E) of the first aspect; and
   (ii) at least one copy of wild-type eIF4E or eIF(iso)4E, wherein the wild-type copy of eIF4E or eIF(iso)4E can be used by the plant, but cannot be used by a virus.

In a seventh aspect, there is provided use of a plant eukaryotic initiation factor 4E (eIF4E) variant or an isoform thereof (eIF(iso)4E) of the first aspect or the nucleic acid of the second aspect, for inducing viral-resistance in a plant.

In an eighth aspect, there is provided a method for producing a virus-resistant plant, the method comprising crossing a parent plant that expresses a plant eukaryotic initiation factor 4E (eIF4E) variant or an isoform thereof (eIF(iso)4E) of the first aspect with a recipient plant, the recipient comprising at least one trait, selected from a group consisting of an agronomic advantage, a commercial advantage, and/or suitability for a particular climate or soil.

The recipient plant is a commercially useful plant, such as a crop (e.g. rice, wheat etc) or a vegetable (e.g. a tomato etc). As described in the examples and as shown in FIG. 8, the recipient plant (which may be *B. rapa*) may be crossed with a parent plant which is resistant to viral infections, because it expresses the eIF4E or eIF4(iso)4E variant of the first aspect. The method may further comprise back-crossing the progeny of the first cross with the recipient parent (i.e. recurrent plant line). Between 1 and 10 rounds of back-crossing may be required. The method according to the fifth aspect may be used to ensure that the variant allele of eIF4E or eIF(iso)4E (which confers virus resistance) is present in the non-recurrent plants in each cross. Finally, the method may comprise a step of self-pollinating or selfing virus resistant plants derived from the back-crossing programme. Plants in the subsequent generation that are homozygous for the modified splice site (which confers virus resistance) may then be identified.

For breeding $F_1$ hybrid plants with viral resistance, two inbred parent plant lines derived from back-crossing programmes and homozygous for the eIF4E or eIF(iso)4E of the first aspect may be used to generate a $F_1$ hybrid. These two inbred parental lines may then be crossed together to generate virus-resistant $F_1$ hybrids homozygous for the eIF4E or eIF(iso)4E of the first aspect.

It is preferred that the parent plant used in the method may express at least one copy of wild-type eIF4E or eIF(iso)4E, wherein the wild-type copy of eIF4E or eIF(iso)4E may be used by the plant, but not by a virus.

In a ninth aspect, the invention provides a virus-resistant plant produced by or obtainable by the method of the eighth aspect.

In a tenth aspect, the invention provides a virus-resistant plant comprising the plant eukaryotic translation initiation factor 4E (eIF4E) variant or an isoform thereof (eIF(iso)4E) of the first aspect, or the nucleic acid encoding an alternatively spliced variant of eIF4E or eIF(iso)4E of the second aspect.

Preferably, the plant of the ninth and tenth aspects expresses at least one copy of wild-type eIF4E or eIF(iso) 4E, wherein the wild-type copy of eIF4E or eIF(iso)4E can be used by the plant but not by a virus. The plant may comprise a modification or mutation in a non-coding region of the gene encoding eIF4E or eIF(iso)4E. The modification may be within a splice-element of eIF4E or eIF(iso)4E nucleic acid.

The use, method or plant may comprise use of eIF(iso) 4E.a, eIF(iso)4E.b or eIF(iso)4E.c, preferably eIF(iso)4E.a.

The plant may be of the family Solanaceae, such as potato, all species, tomato, pepper or egg plant, Cucurbits, such as melons, squash and cucumbers, Cruciferous crops, particularly *Brassica napus* such as oilseed rape, *Brassica rapa* such as Chinese cabbage, and even more particularly *Brassica oleracea* such as broccoli, cauliflower, cabbage, savoy cabbage, Brussels sprouts, red cabbage, and the like etc., Fabaceae peas, beans, pulses etc. and also any monocotyledonous crops, including rice, maize, wheat, barley etc. In one preferred embodiment, the plant may be *Brassica* spp, preferably *B. rapa* and/or *Brassica oleracea*.

It will be appreciated that the method of any one of the fifth, sixth or eighth aspects, the use of the seventh aspect, or the plant of the ninth aspect may comprise the use of a transgenic plant. Indeed, any of the plants described herein may be transgenic, i.e. produced using recombinant DNA technology.

The scenario described above explains virus resistance in plants that possess a single copy of eIF4E and/or eIF(iso)4E, which a virus can use to complete its life-cycle and cause an infection. Thus, in the preferred embodiments, the plant is homozygous for eIF4E and/or eIF(iso)4E, which encodes the alternatively spliced variant of a plant eukaryotic translation initiation factor 4E (eIF4E), or an isoform thereof (eIF(iso)4E), which is non-functional for a virus.

However, it will be appreciated that some plants have multiple copies/loci of one, or both of these two genes. For example, *Brassica rapa* has three copies of both eIF4E and eIF(iso)4E (i.e. BraA.eIF4E.a, b and c; and BraA.eIF(iso) 4E.a, b and c), and a virus may be able to use any of these genes to complete its life cycle, and cause a viral infection in the host plant. Thus, in order to confer virus resistance in plants having multiple copies/loci of eIF4E and/or eIF(iso) 4E, it is preferred that the alleles of eIF4E and/or eIF(iso)4E at each of these other loci are also non-functional for the virus.

In order to investigate this further, the inventors crossed the *B. rapa* virus infection-susceptible line R-o-18 and the virus-resistant line RLR22 and an $F_1$ plant was backcrossed to a self from the resistant plant to produce a $B_1$ plant that was homozygous for the RLR22 allele of BraA.eIF(iso)4E.a and the RLR22 allele of BraA.eIF4E.c, but heterozygous at the BraA.eIF(iso)4E.c locus. $B_1S_1$ plants derived from this particular individual were then phenotyped and genotyped. Surprisingly, plants homozygous for the RLR22 allele of BraA.eIF(iso)4E.c were completely resistant to Turnip mosaic virus (TuMV), heterozygotes were only slightly susceptible to virus infection, whereas plants that were homozygous for the R-o-18 allele of BraA.eIF(iso)4E.c were completely susceptible to viral infections.

Accordingly, the inventors have identified a second locus involved in the broad-spectrum resistance to the virus in *B. rapa* as BraA.eIF(iso)4E.c on chromosome A8. This second locus is referred to herein as ConTR01. The inventors believe that, for broad-spectrum virus resistance, a plant requires the second gene (i.e. ConTR01, the RLR22 allele of BraA.eIF(iso)4E.c) in addition to the first gene (i.e. retr01, the RLR22 allele of BraA.eIF(iso)4E.a). This demonstrates the importance of more than one gene for conferring virus resistance in plants where viruses are able to utilise multiple copies/loci of eIF4E and/or eIF(iso)4E. The genomic DNA sequences determined for the eIF4E and eIF(iso)4E alleles from *Brassica rapa* lines R-o-18 and RLR22 and predicted mRNA and polypeptide sequences are provided below along with information on whether Turnip mosaic virus is able to use each allele.

R-o-18 BraA.eIF4E.a

The R-o-18 allele of BraA.eIF4E.a located on chromosome A1, which TuMV cannot use in *B. rapa*, has the following genomic DNA sequence (exons 1 to 5, with the introns shown in bold):

(SEQ ID No. 34)

```
ATGGCGGTAGAAGACACACTCAAGCCTAATGTCGCTACGGAAGAATCGAATCCCAATTCTGCAGATCACC

CGATCGATCGATACCATGAGGAAGGCGACGATGCCGAGGAAGGAGCGACCGTAGACGAATCGAGCAAATC

CGCCGTCCCTGAATCGCATCCGTTGGAGCATTCGTGGACTCTCTGGTTCGATAACCCTTCCGTCAAATCA

AAGCAGACGACTTGGGGAAGCTCCTTACGATCCGTCTTCACCTTCTCCACCGTCGAGGAGTTCTGGAGGT

TGGTAGCTTTACAACAATCTTTTTCCTTCTTACAGTAATTCCACAATCTGGGTTTTGTTTAGATTTTGAT

TTCTCACAGGAAAGTTATCTTCTTTGTTGTTGCTGTTAGAATCTTGTTTGATGTTTGAACAAACAGTTAC

TTGTTGGATGCTAGTGTATTGGCTTTGACATTTTACTTTTGATTTGTAGTTTGTACAATAACATTCGGCA

CCCGAGCAAGTTAGCTAACGGAGCTGACTTGTACTGTTTCAAACACAATATTGAACCTAAGTGGGAGGAT

CCTATCTGTGCCAACGGAGGCAAGTGGACTATGAACTTCTCTAGGGAGAAGTCTGATAAGCCCTTTCTTT

ACACCGTATGTAACTTGACATTCATATAGTTCTTGTTTCACACCATCCAGTCTCCAGTCTAATCGGGTTG

TTGTTGTTGTtgttgtCACTTGTAGTTGCTTGCTTTGATTGGAGAACAGTTTGACCATGGAGATGAAATC

TGTGGAGTTGTTGTTAACGTTAGAGCTAAGCAAGAGAGGATATCTATTTGGACTAAAAACTCTTCCAACG

AAGCGGCTCAGGTACAAGACAAAAAAAACCCACATCAAACTGTGTCTCTCTCGGTCTGAAGAAAAGAC

GTGGAAATTTTATTTTATTTAATGTTACAGGTGAGCATTGGGAGACAGTGGAAGGAGTTTCTTGATTACA
```

-continued

```
ACAGCAGCATTGGTTTCATCATCCATGTAAAGAGCGTTTCTGTTGTTGCTAATTTCTGTTTTTTTTTCT

TTCTATGGATCGCTCACTACTTGTTGTATGTGTGTATTGGTTTGGTTTCTCTTCAGGAGGATGCGaAGaA

GCTGGACAGAGGCGCAAAGAGCGCTTACACTGCCTGA
```

The R-o-18 allele of BraA.eIF4E.a, which TuMV cannot use in *B. rapa*, has the following mRNA sequence:

```
                                                      (SEQ ID No. 35)
AUGGCGGUAGAAGACACACUCAAGCCUAAUGUCGCUACGGAAGAAUCGAAUCCCAAUUCUGCAGAUCACC

CGAUCGAUCGAUACCAUGAGGAAGGCGACGAUGCCGAGGAAGGAGCGACCGUAGACGAAUCGAGCAAAUC

CGCCGUCCCUGAAUCGCAUCCGUUGGAGCAUUCGUGGACUCUCUGGUUCGAUAACCCUUCCGUCAAAUCA

AAGCAGACGACUUGGGGAAGCUCCUUACGAUCCGUCUUCACCUUCUCCACCGUCGAGGAGUUCUGGAGUU

UGUACAAUAACAUUCGGCACCCGAGCAAGUUAGCUAACGGAGCUGACUUGUACUGUUUCAAACACAAUAU

UGAACCUAAGUGGGAGGAUCCUAUCUGUGCCAACGGAGGCAAGUGGACUAUGAACUUCUCUAGGGAGAAG

UCUGAUAAGCCCUUUCUUUACACCUUGCUUGCUUUGAUUGGAGAACAGUUUGACCAUGGAGAUGAAAUCU

GUGGAGUUGUUGUUAACGUUAGAGCUAAGCAAGAGAGGAUAUCUAUUUGGACUAAAAACUCUUCCAACGA

AGCGGCUCAGGUGAGCAUUGGGAGACAGUGGAAGGAGUUUCUUGAUUACAACAGCAGCAUUGGUUUCAUC

AUCCAUGAGGAUGCGaAGaAGCUGGACAGAGGCGCAAAGAGCGCUUACACUGCCUGA
```

The R-o-18 allele of BraA.eIF4E.a, which TuMV cannot use in *B. rapa*, codes for the following polypeptide sequence:

```
                                                      (SEQ ID No. 36)
MAVEDTLKPNVATEESNPNSADHPIDRYHEEGDDAEEGATVDESSKSAVPESHPLEHSWTLWFDNPSVKS

KQTTWGSSLRSVFTFSTVEEFWSLYNNIRHPSKLANGADLYCFKHNIEPKWEDPICANGGKWTMNFSREK

SDKPFLYTLLALIGEQFDHGDEICGVVVNVRAKQERISIWTKNSSNEAAQVSIGRQWKEFLDYNSSIGFI

IHEDAKKLDRGAKSAYTA.
```

RLR22BraA.eIF4E.a

The RLR22 allele of BraA.eIF4E.a located on chromosome A1 which TuMV cannot use in *B. rapa* has the following genomic DNA sequence (exons 1 to 5, with the introns shown in bold):

```
                                                      (SEQ ID No. 37)
ATGGCGGTAGAAGACACTCTCAAGCCTAACGTCCCTACGAAGAATCGAATCCCAATTCTGTAGATCACC

CGATCGATCGATACCATGAGGAAGGCGACGATGCCGAGGAAGGAGCGATCGTAGACGAATCGAGCAAATC

CGCCGTCCCTGAATCGCATCCGTTGGAGCATTCGTGGACTCTCTGGTTCGATAACCCTTCCGTCAAATCA

AAGCAGACGACTTGGGGAAGCTCCTTACGATCCGTCTTCACCTTCTCCACCGTCGAGGAGTTCTGGAGGT

TGGTAGCTTTACAACAATCTTTTTCCTTCTTAATGTAATTCCACAATCTGGGTTTTGTTTAGATTTCGAT

TTCTCACAGGAAAGTTATCTTCTTTATGGGTGGGTTTAAATCTCATGAAGTCACTGTTCTTCTCTGTCTA

TGAAGAATTGCCTGTTTGGTGTTTGAACAAACAGTTACTTGTTGGATGCTATTTTATTGGCTTCTTATTA

TATGTGACATTGCAGTTTGTACAATAACATTCGGCATCCGAGCAAGTTAGCTAACGGAGCTGACTTGTAC

TATTTCAAACACAATATTGAACCTAAGTGGGAGGATCCTATCTGTGCCAACGGAGGCAAGTGGACTATGA

ACTTCTCTAGGGAGAAGTCTGATAAGCCCTTTCTTTACACCGTATGTAACTTGACATTCATATAGTTCTT

GTTTCACACCATCCAGTCTCCAGTCTAATCGGGTTGTTGTTGTTGTTGTCACTTATAGTTGCTTGCTTTG

ATTGGAGAACAGTTTGACCATGGAGATGAAATCTGTGGAGTTGTTGTTAACGTTAGAGCTAAGCAAGAAA
```

GGATATCTATTTGGACTAAAAACTCTTCCAACGAAGCTGCTCAGGTACAAGACAAAAAAAGAACCCCCAT

CGAACTGTATCTCTCTCGGTCTGAAGAAAAGACGTGGAAATTTTATATTGTTTAATGTTACAGGTGAG

CATTGGGAGACAGTGGAAGGAGTTTCTTGATTACAACAGCAGCATTGGTTTCATCATCCATGTAATAGTA

TTTCTGTTGTTGCTAATTTCTTTCTTTTTTTCTTCTATGGATCGCTCACTACTTGTTGTATGTGTGTATT

GGTTTGGTTTCTCTTCAGGAGGATGCGAAGAAGCTGGACAGAGGCGCAAAGAGCGCTTACACTGCCTGA

The RLR22 allele of BraA.eIF4E.a which TuMV cannot use in *B. rapa* has the following mRNA sequence:

(SEQ ID No. 38)
AUGGCGGUAGAAGACACUCUCAAGCCUAACGUCCCUACGGAAGAAUCGAAUCCCAAUUCUGUAGAUCACC

CGAUCGAUCGAUACCAUGAGGAAGGCGACGAUGCCGAGGAAGGAGCGAUCGUAGACGAAUCGAGCAAAUC

CGCCGUCCCUGAAUCGCAUCCGUUGGAGCAUUCGUGGACUCUCUGGUUCGAUAACCCUUCCGUCAAAUCA

AAGCAGACGACUUGGGGAAGCUCCUUACGAUCCGUCUUCACCUUCUCCACCGUCGAGGAGUUCGGGAGUU

UGUACAAUAACAUUCGGCAUCCGAGCAAGUUAGCUAACGGAGCUGACUUGUACUAUUUCAAACACAAUAU

UGAACCUAAGUGGGAGGAUCCUAUCUGUGCCAACGGAGGCAAGUGGACUAUGAACUUCUCUAGGGAGAAG

UCUGAUAAGCCCUUUCUUUACACGUUGCUUGCUUUGAUUGGAGAACAGUUUGACCAUGGAGAUGAAAUCU

GUGGAGUUGUUGUUAACGUUAGAGCUAAGCAAGAAAGGAUAUCUAUUUGGACUAAAAACUCUUCCAACGA

AGCUGCUCAGGUGAGCAUUGGGAGACAGUGGAAGGAGUUUCUUGAUUACAACAGCAGCAUUGGUUUCAUC

AUCCAUGAGGAUGCGAAGAAGCUGGACAGAGGCGCAAAGAGCGCUUACACUGCCUGA

The RLR22 allele of BraA.eIF4E.a which TuMV cannot use in *B. rapa* codes for the following polypeptide sequence:

(SEQ ID No. 39)
MAVEDTLKPNVPTEESNPNSVDHPIDRYHEEGDDAEEGAIVDESSKSAVPESHPLEHSWTLWFDNPSVKS

KQTTWGSSLRSVFTFSTVEEFWSLYNNIRHPSKLANGADLYYFKHNIEPKWEDPICANGGKWTMNFSREK

SDKPFLYTLLALIGEQFDHGDEICGVVVNVRAKQERISIWTKNSSNEAAQVSIGRQWKEFLDYNSSIGFI

IHEDAKKLDRGAKSAYTA.

R-o-18 BraA.eIF4E.b

R-o-18 BraA.eIF4E.b located on chromosome A3 is non-functional. The R-o-18 allele of BraA.eIF4E.b which is non-functional has the following genomic DNA sequence (exons 1 to 3, with the introns shown in bold and premature stop codons being underlined):

(SEQ ID No. 40)
ATGGCGGTAGAAGACACTTTCAAGCCTGTTGTTGCTATCAaGGAAGCGAAACCTAATTATGTAGAGCATC

TGATTGGACCAGGCGACGATGCGGAGGAAGGAGAGATCGTAGACGGAGATGTTGACAAATCTGGAAATCC

ACAGTTCCTGAATCGCATTCGTTGGAGCATTTGTGGACTTTCCACAGTTCCTCTTTTTATTCGT<u>TGA</u>CTT

TCTAACGAAAAGACGACTTGGGGAAGCTCCTTAGATCCGCGTTCACGTTCTCCACGGTCGAGGAGTTCTG

GAGGTTGGTGCTTTAAAACAATCTTTTCGTTCTTCCAATAATTCTACAATCTGGGTTTTGGTTTGGATTT

AGATTTCTCGAGGAAAGTTATGTTCTTTGTTGATGGGTTAGATCACATGAAGTCATCGTTCTTATCTGTT

TCTGAAGAATTGTTTGTTTGATGTTTGAATTTGTAGCTACAAGCTTATATGTTAAGTTTTTAAAAAGATA

GCGAAGATATTATATTCGATGTAAATCAATGTTTTACACCTTAGTATTTTTGTTGGTAACAGAAGATGAA

CAAAGAGTTATTTGGTTAGTGTTGGATGCTATTGTATTGCTGTGCACTCGTGTGTGTATATGCTTTCTTG

TATTCTCCTTTCTTGAGAACCTTTCTCTCAATGGGAATAATGAACTTGTAGTTTGTTCTATTGGGAGACA

AT<u>AG</u>AAGGAGTTCCTTGATTACAACAGCTGCATTGGTTTCATCATCCATGTGGGAAGAGTGCTTGTCTTG

```
ATGCTAATTCAAAAGGCTTTTCTTTTGCATTTCTCAGTGTTTATTTTTTTGTCTGTATTGGCTTGTTTTC

CCTTCAGGAGGATGCGACGAAGATGAACAAGTACAACCATACTGTTATCGATCTACAATTTGAGTTTTAA
```

The R-o-18 allele of BraA.eIF4E.b which is non-functional has the following mRNA sequence:

(SEQ ID No. 41)
```
AUGGCGGUAGAAGACACUUUCAAGCCUGUUGUUGCUAUCAaGGAAGCGAAACCUAAUUAUGUAGAGCAUC

UGAUUGGACCAGGCGACGAUGCGGAGGAAGGAGAGAUCGUAGACGGAGAUGUUGACAAAUCUGGAAAUCC

ACAGUUCCUGAAUCGCAUUCGUUGGAGCAUUUGUGGACUUUCCACAGUUCCUCUUUUUAUUCGUUGACUU

UCUAACGAAAAGACGACUUGGGGAAGCUCCCUUAGAUCCGCGUUCACGUUCUCCACGGUCGAGGAGUUCUG

GAGUGGGAGACAAUAGAAGGAGUUCCUUGAUUACAACAGCUGCAUUGGUUUCAUCAUCCAUGAGGAUGCG

ACGAAGAUGAACAAGUACAACCAUACUGUUAUCGAUCUACAAUUUGAGUUUUAA
```

The R-o-18 allele of BraA.eIF4E.b which is non-functional codes for the following polypeptide sequence:

(SEQ ID No. 42)
```
MAVEDTFKPVVAIKEAKPNYVEHLIGPGDDAEEGEIVDGDVDKSGNPQFLNRIRWSICGLSTVPLFIR.L

SNEKTTWGSSLDPRSRSPRSRSSGVGDNRRSSLITTAALVSSSMRMRRR.TSTTILLSIYNLSF
```

RLR22BraA.eIF4E.b

No sequence obtained for the RLR22 allele of BraA.eIF4E.b located on chromosome A3.

R-o-18 BraA.eIF4E.c

The R-o-18 allele of BraA.eIF4E.c located on chromosome A8 which TuMV cannot use in *B. rapa* has the following genomic DNA sequence (exons 1 to 5, with the introns shown in bold):

(SEQ ID No. 43)
```
ATGGCGGTAGAAGACACTTCCAAGCCTGTTGTCGTTGCGGAaGaAGCGAACCCTAACCCCACAGACCATC

CGATTGATCGATACCATGAAGAAGGCGACGATGCTGAGGAAGGAGAGATCGCCGGCGGCGAAGGAGACGG

AGACGAATCGAGCAAATCCGCCGTTCCGCAGTCGCATCCGTTGGAGCATTCGTGGACTTTCTGGTTCGAT

AACCCTTCTGTTAAATTAAAGCAGGCGACTTGGGGAAGCTCCTTGCGATCCGTGTTCACTTTCTCCACCG

TCGAGGAGTTCTGGAGGTTAGGGCTTTTTACAAAATCAATAATTTATTCTTACAATTATTATTTCGACAT

GGGTTTTAGTTTGGTTTTGTCTAGATTATGTTTTCTCGAAGAAAGTTATGTTCTTTCTTCGTGGGTTAAG

TGAATCACTTGTTCTTGTTTGTTTCTGAAATATTGCTTTGCTTGTTTGTTTGGTGTTTGAATTATGGAAA

AGGAATCTTTTGTTCTTTCAATGACTATGCGGCATGGGTTTTGGTTTAGTTTTGTTTAGATTGTTATATC

TCAAGGAAAGTTATGTTCTTTGTTGGTGGGTTAGATTCCGTGAAGTCACTTGCTCTTGTATGTTTCTGAA

GAATCACTTAATTGGTGTTTGAGTTTGTAGCTACTGCTTATATGTTAAGGTCATATTTGTTCGCTTGTTA

TCTTCACAAGAGCTAAAACATTGAACCAGGGAATCATCGGTCTTATTCGGTTAATGTTGGATGCTATTGT

GTTGTTGCGTGTGTGTATATATACTTTCTTGTGTTCTTCTTTTTGATTTGTGAGTCTCTCTCAAGTCTCA

ATGGGATTTAAGGACTTGTCTTTGGCTCTATTGACTTCATCTTACTTTGGTTGCAGTCTGTTCAATAACA

TGAGGGGTCCGAGCAAGTTAGCTGGCGGAGCTGACTTCTACTGTTTCAAGCACAATATCGAACCTAAGTG

GGAGGATCCTATCTGTGCTAATGGAGGCAAATGGACTATGAACTTCCCGAAGGAGAAGTCTGATAAGCCC

TGGCTTTACACCGTATGGTTTTGATTCTTCTTACTTGAACACATGATTCTTGTTTCACCATCCATTCGAG

TCTGATTGGGTTTTTGTTTTCTCGATGTAGTTGCTTGCGTTGATTGGAGAACAGTTTGACCATGGAGATG

AGATATGCGGAGCTGTTGTCAACGTTAGAGGAAAGCAAGAGAGGATTTCCATTTGGACCAAAAATGCTTC

CAACGAAGCTGCTCAGGTAAAAGATCATTTATTGACAAATAAATGTTAAATTGTCTCTCTTCCGGCTAAA
```

AGACCTGAAATTTCTTGTTTCCTTTGATGTTGCAGGTGAGCATTGGGAAACAATGGAAGGAGTTTATTGA

TTACAACAACAGCATTGGTTTCATCATCCATGTAAGAAGAGAGCTTTTCTCTTGAATGCTTATTCATAAG

TTTTTTTTTAATATCTCACTGTCTGTATTGTTTTTTTTTTCTTCAGGAGGATGCCAAGAAGCTGGACAGG

GGCGCGAAGAGCGCTTACACCGCTTGA

The R-o-18 allele of BraA.eIF4E.c which TuMV cannot use in *B. rapa* has the following mRNA sequence:

(SEQ ID No. 44)
AUGGCGGUAGAAGACACUUCCAAGCCUGUUGUCGUUGCGGAaGaAGCGAACCCUAACCCCACAGACCAUC

CGAUUGAUCGAUACCAUGAAGAAGGCGACGAUGCUGAGGAAGGAGAGAUCGCCGGCGGCGAAGGAGACGG

AGACGAAUCGAGCAAAUCCGCCGUUCCGCAGUCGCAUCCGUUGGAGCAUUCGUGGACUUUCUGGUUCGAU

AACCCUUCUGUUAAAUUAAAGCAGGCGACUUGGGGAAGCUCCUUGCGAUCCGUGUUCACUUUCUCCACCG

UCGAGGAGUUCUGGAGUCUGUUCAAUAACAUGAGGGGUCCGAGCAAGUUAGCUGGCGGAGCUGACUUCUA

CUGUUUCAAGCACAAUAUCGAACCUAAGUGGGAGGAUCCUAUCUGUGCUAAUGGAGGCAAAUGGACUAUG

AACUUCCCGAAGGAGAAGUCUGAUAAGCCCUGGCUUUACACCUUGCUUGCGUUGAUUGGAGAACAGUUUG

ACCAUGGAGAUGAGAUAUGCGGAGCUGUUGUCAACGUUAGAGGAAAGCAAGAGAGGAUUUCCAUUUGGAC

CAAAAAUGCUUCCAACGAAGCUGCUCAGGUGAGCAUUGGGAAACAAUGGAAGGAGUUUAUUGAUUACAAC

AACAGCAUUGGUUUCAUCAUCCAUGAGGAUGCCAAGAAGCUGGACAGGGGCGCGAAGAGCGCUUACACCG

CUUGA

The R-o-18 allele of BraA.eIF4E.c which TuMV cannot use in *B. rapa* codes for the following polypeptide sequence:

(SEQ ID No. 45)
MAVEDTSKPVVVAEEANPNPTDHPIDRYHEEGDDAEEGEIAGGEGDGDESSKSAVPQSHPLEHSWTFWFD

NPSVKLKQATWGSSLRSVFTFSTVEEFWSLFNNMRGPSKLAGGADFYCFKHNIEPKWEDPICANGGKWTM

NFPKEKSDKPWLYTLLALIGEQFDHGDEICGAVVNVRGKQERISIWTKNASNEAAQVSIGKQWKEFIDYN

NSIGFIIHEDAKKLDRGAKSAYTA.

RLR22BraA.eIF4E.c

The RLR22 allele of BraA.eIF4E.c located on chromosome A8 which TuMV cannot use in *B. rapa* has the following genomic DNA sequence (exons 1 to 5, with the introns shown in bold):

(SEQ ID No. 46)
ATGGCGGTAGAAGACACTTCCAAGCCTGTTGTCGTTGCGGAAGAAGCGAACCCTAACCCCACAGACCATC

CGATTGATCGATACCATGAAGAAGGCGACGATGTTGAGGAAGGAGAGATCGCCGGCGGCGAAACAGACGG

AGACGAATCGAGCAAATCCGCCGTTCCGCAGTCGCATCCGTTGGAGCATTCGTGGACCTTCTGGTTCGAT

AACCCTTCTGTTAAATTAAAGCAGGCGACTTGGGGAAGCTCCTTGCGATCCGTGTTCACTTTCTCCACCG

TCGAGGAGTTCTGGAGGTTAGGGCTTTTTACAAAATCAATAATTTATTCTTGCAATGATTATTTCGACAT

GGGTTTTAGTTTGGTTTTGTCTAGATTATGTTTTCTCGAGGAAAGTTATGTTCTTTCTTCGTGGGTTAAG

TCAAGTCACTTGTTCTTGTCTGTTTCTGAAGTATGACTTGTTTGGTGTTTGAATTATGGAGGTCAGGCCT

TACAAAACAATCTTTTGTTCTTCTTCTGATTATTTCGACATGGGTTTTAGTTTGGTTTTGTCTAGATTAT

-continued

```
GTTTTCTCGAGGAAAGTTATGTTCTTTCTTGTTGGGTTAAGTGAAGTCACTTGCTCTTGTCTGTTTCTGA
AATATTACTTGTTTGGTGTTTGAAATTGTAGCTACTGCTTATATGTTAAGGTCATATTTGTTCACTTCTA
ATCTTCACAAGAGCTAAAACATTGAACTAGGGAATCATTGGTCTTATTTGGTTAATGTTGGATGCTATTG
TGTTGTTGCG (SEQ ID No. 49)
ATGGCGACGGAGGATGTGAACGAAGCCCTTGCGGCGGCGGAAGTACCGATAGAGTCGACAACGGAGAAGC

AGCCTCATAAGCTGGAAAGAAAATGGTGTTTCTGGTTCGATAACCAATCTAAGCCAAAGCAAGGCGCCGC

CTGGGGAGCTTCCCTTCGTAAAGCCTCTACCTTCGACACTGTCGAAGATTTCTGGGGGTGTGTCGTGTCT

TCTTCTCCTCCTCATTTTTAGATTTCTTCGATTAACTTCTTCTGGCATGCGTTTTTGCAGTTTGCACGAG

ACTATATTCATTCCCAGCAAATTGACACCCAATGCTGATATCCACTTGTTCAAAGCTGGCGTTGAGCCCA

AGTGGGAAGATCCTGAGTGTGCTCACGGCGGAAAGTGGACTTTTGTTGTCACCAACAACAGGAAGCAAGC

TTTAGACAAGGCTTGGCTTGAAACTGTAATACCGTCTTCCCTTTTACTGTTTTTGTCTTTAGACAATTGT

GGCTTATGTCCTAATGTCTGTTTCTTCTCTCTCTCTCGTAATTGGGCGGCAGTTGATGGCTTTGATTG

GAGAGCAATTCGATGAGGCAGATGAGATTTGTGGTGTTGTTGCTAGTGTGCGCCTAAAGCAAGACAAGCT

CTCCTTGTGGACACGGACTAAATCAAATGAAGCTGTCCTGGTTAGATTACGAATCATGTTTTCTTCTAGT

TGTCtTTTTTTTTTTTTTTTTCATTTTCTTGCTTTTTGGTGGTGTGCGATGAGATGCCCAAGTACTATT

CACTAGCTTCCTTTGTTGAACGTGTTGATTGCTTTCTACAGTAAAATAGCATAAGCTGTTTAATATATCA

ATAACGCTACTCTAAATTATCAACGAAAGATGTAGAGAGGTTTTTTATAATGAGTTAAATTAGTTTTTAT

ACTGAAGGTTTATAGGTTCGTTTAACTATTCATATTTCTGTGATACCTGCTTTTATAGTTTACGCTCTAT

AAACATAGCATTTGACAGCTCTTTAGAACATGGCAGTATCTAGATGCTAAAAGACTAGTTTCTGAATCTG

TCTGCTTAAATTACTGCTTTGTTGTTTGTTATGGTAAATTCAGATGGGTATTGGAAAGAAGTGGAAGGCG

CTACTTGACGTCACCGACAAGATAACTTTCACTAACCATGTAATTAACGTTCTCCTATAGAAGCTAATAT

TACTTTTGTTCATGTTTATCCTTTCACGTGCTTACTAAAATCTGGTCTACTTACTTGCAGGATGATTCTA

GAAGAAGTCGGTTCACTGTCTGA

The R-o-18 allele of BraA.eIF(iso)4E.b which TuMV
cannot use in *B. rapa* has the following mRNA sequence:

(SEQ ID No. 50)
AUGGCGACGGAGGAUGUGAACGAAGCCCUUGCGGCGGCGGAAGUACCGAUAGAGUCGACAACGGAGAAGC

AGCCUCAUAAGCUGGAAAGAAAAUGGUGUUUCUGGUUCGAUAACCAAUCUAAGCCAAAGCAAGGCGCCGC

CUGGGGAGCUUCCCUUCGUAAAGCCUCUACCUUCGACACUGUCGAAGAUUUCUGGGGUUUGCACGAGACU

AUAUUCAUUCCCAGCAAAUUGACACCCAAUGCUGAUAUCCACUUGUUCAAAGCUGGCGUUGAGCCCAAGU

GGGAAGAUCCUGAGUGUGCUCACGGCGGAAAGUGGACUUUUGUUGUCACCAACAACAGGAAGCAAGCUUU

AGACAAGGCUUGGCUUGAAACUUUGAUGGCUUUGAUUGGAGAGCAAUUCGAUGAGGCAGAUGAGAUUUGU

GGUGUUGUUGCUAGUGUGCGCCUAAAGCAAGACAAGCUCUCCUUGUGGACACGGACUAAAUCAAAUGAAG

CUGUCCUGAUGGGUAUUGGAAAGAAGUGGAAGGCGCUACUUGACGUCACCGACAAGAUAACUUUCACUAA

CCAUGAUGAUUCUAGAAGAAGUCGGUUCACUGUCUGA

The R-o-18 allele of BraA.eIF(iso)4E.b which TuMV
cannot use in *B. rapa* codes for the following polypeptide
sequence (same as RLR22BraA.eIF(iso)4E.b):

(SEQ ID No. 51)
MATEDVNEALAAAEVPIESTTEKQPHKLERKWCFWFDNQSKPKQGAAWGASLRKASTFDTVEDFWGLHET

IFIPSKLTPNADIHLFKAGVEPKWEDPECAHGGKWTFVVTNNRKQALDKAWLETLMALIGEQFDEADEIC

GVVASVRLKQDKLSLWTRTKSNEAVLMGIGKKWKALLDVTDKITFTNHDDSRRSRFTV.

RLR22BraA.eIF(iso)4E.b

The RLR22 allele of BraA.eIF(iso)4E.b located on chromosome A5 which TuMV cannot use in *B. rapa* has the following genomic DNA sequence (exons 1 to 5, with the introns shown in bold):

(SEQ ID No. 52)
ATGGCGACGGAGGATGTGAACGAAGCCCTTGCGGCGGCGGAAGTACCGATAGAGTCGACAACGGAGAAGC

AGCCTCATAAGCTGGAAAGAAAATGGTGTTTCTGGTTCGATAACCAATCTAAGCCAAAGCAAGGCGCCGC

CTGGGGAGCTTCCCTTCGTAAAGCCTCTACCTTCGACACTGTCGAAGATTTCTGGGGGTGTGTCGTGTCT

TCTTCTCCTCCTCATTTTTAGATTTCTTCGATTAACTTCTTCTGGCATGCGTTTTTGCAGTTTGCACGAG

ACTATATTCATTCCCAGCAAATTGACACCCAATGCTGATATCCACTTGTTCAAAGCTGGCGTTGAGCCCA

AGTGGGAAGATCCTGAGTGTGCTCACGGCGGAAAGTGGACTTTTGTTGTCACCAACAACAGGAAGCAAGC

TTTAGACAAGGCTTGGCTTGAAACTGTAATACCGTCTTCCCTTTTACTGTTTTTGTCTTTAGACAATTGT

GGCTTATGTCCTAATGTCTGTTTCTTCTCTCTCTCTCGTAATTGGGCGGCAGTTGATGGCTTTGATTG

GAGAGCAATTCGATGAGGCAGATGAGATTTGTGGTGTTGTTGCTAGTGTGCGCCTAAAGCAAGACAAGCT

CTCCTTGTGGACACGGACTAAATCAAATGAAGCTGTCCTGGTTAGATTACGAATCATGTTTTCTTCTAGT

TGTCTTTTTTTTTTTTTTTTCATTTTCTTGCTTTTTGGTGGTGTGCGATGAGATGCCCAAGTACTATT

CACTAGCTTCCTTTGTTGAACGTGTTGATTGCTTTCTACAGTAAAATAGCATAAGCTGTTTAATATATCA

ATAACGCTACTCTAAATTATCAACGAAAGATGTAGAGAGGTTTTTTATAATGAGTTAAATTAGTTTTTAT

ACTGAAGGTTTATAGGTTCGTTTAACTATTCATATTTCTGTGATACCTGCTTTTATAGTTTACGCTCTAT

AAACATAGCATTTGACAGCTCTTTAGAACATGGCAGTATCTAGATGCTAAAAGACTAGTTTCTGAATCTG

TCTGCTTAAATTACTGCTTTGTTGTTTGTTATGGTAAATTCAGATGGGTATTGGAAAGAAGTGGAAGGCG

CTACTTGACGTCACCGACAAGATAACTTTCACTAACCATGTAATTAACGTTCTCCTATAGAAGCTAATAT

TACTTTTGTTCATGTTTATCCTTTCACGTGCTTACTAAAATCTGGTCTACTTACTTGCAGGATGATTCTA

GAAGAAGTCGGTTCACTGTCTGA

The RLR22 allele of BraA.eIF(iso)4E.b which TuMV cannot use in *B. rapa* has the following mRNA sequence:

(SEQ ID No. 53)
AUGGCGACGGAGGAUGUGAACGAAGCCCUUGCGGCGGCGGAAGUACCGAUAGAGUCGACAACGGAGAAGC

AGCCUCAUAAGCUGGAAAGAAAAUGGUGUUUCUGGUUCGAUAACCAAUCUAAGCCAAAGCAAGGCGCCGC

CUGGGGAGCUUCCCUUCGUAAAGCCUCUACCUUCGACACUGUCGAAGAUUUCUGGGGUUUGCACGAGACU

AUAUUCAUUCCCAGCAAAUUGACACCCAAUGCUGAUAUCCACUUGUUCAAAGCUGGCGUUGAGCCCAAGU

GGGAAGAUCCUGAGUGUGCUCACGGCGGAAAGUGGACUUUUGUUGUCACCAACAACAGGAAGCAAGCUUU

AGACAAGGCUUGGCUUGAAACUUUGAUGGCUUUGAUUGGAGAGCAAUUCGAUGAGGCAGAUGAGAUUUGU

GGUGUUGUUGCUAGUGUGCGCCUAAAGCAAGACAAGCUCUCCUUGUGGACACGGACUAAAUCAAAUGAAG

CUGUCCUGAUGGGUAUUGGAAAGAAGUGGAAGGCGCUACUUGACGUCACCGACAAGAUAACUUUCACUAA

CCAUGAUGAUUCUAGAAGAAGUCGGUUCACUGUCUGA

The RLR22 allele of BraA.eIF(iso)4E.b which TuMV cannot use in *B. rapa* codes for the following polypeptide sequence (same as R-o-18 BraA.eIF(iso)4E.b):

(SEQ ID No. 54)
MATEDVNEALAAAEVPIESTTEKQPHKLERKWCFWFDNQSKPKQGAAWGASLRKASTFDTVEDFWGLHET

IFIPSKLTPNADIHLFKAGVEPKWEDPECAHGGKWTFVVTNNRKQALDKAWLETLMALIGEQFDEADEIC

GVVASVRLKQDKLSLWTRTKSNEAVLMGIGKKWKALLDVTDKITFTNHDDSRRSRFTV.

R-o-18 BraA.eIF(iso)4E.c

The R-o-18 allele of BraA.eIF(iso)4E.c located on chromosome A8 which TuMV can use in *B. rapa* and confers susceptibility on plants has the following genomic DNA sequence (exons 1 to 5, with the introns shown in bold):

(SEQ ID No. 55)
ATGGCGACAGAGGATGTGAACGAAGCCCTTGCGGCGGCGGAGGTAACGGCGATAGAATCGACGGAGAAGC

AGCAGCCTCCTCACAAGCTCGAAAGAAAGTGGAGTCTCTGGTTCGATAACCAATCGAAACCCAAGCAAGG

CGCCGCCTGGGGAGTTTCCCTCCGTAAAGCATGTACCTTCGATACCGTCGAAGACTTCTGGGGGTTTGTC

TTTTTCTTCTTCGATCTAAGATTTTCTGTGAAGTTATACTAATAAGGGTGTGTGTATTGTTGCAGTTTGC

ACGAGACTATCTTCGTTCCCAGCAGATTGACACCCAACGCTGACATTCACATGTTCAAAGCTGGTGTTGA

GCCCAAGTGGGAAGATCCTGAGTGTGCTAACGGCGGAAAGTGGACTTATGTTGTTACCAACAACAGGAAG

CAAGCTTTAGACAAGGCTTGGCTTGAAACTGTACTCTTCTTCTTCTTCTAACCCTTTTTACTCTTCTGTT

TTCTGACTTAATAATTTTATCTCTTGTGTTTGGCAGTTGATGGCTTTAGTTGGAGAGCAGTTTGATGAGG

CAGATGAGATCTGTGGTGTGGTTGCTAGTGTCCGCCAAAAGCAAGACAAGCTCTCCTTGTGGACTAGGAC

TAAATCTAATGAAGCTGTTCTGGTATCATGCTTCTCTTCTCCCTTATATATGTTTGTTTGACAGTTTTTT

AAACCACCTTTTGATACTTTGCTGACAGTATAATCATAAGCTATATTTGCCAAAGGATATATATATATCA

GTTTAGAACATGTTAGTATGTCAAAGATGGTTTATGAATCTATCTATCGGATGAAATTGCTGCTTGTTGT

TTGTTTATTGTTATTATGTTTTATATTGGTTTATGATCCTATCTGATGAGATTTCTACTCTGCTGTATAT

TTAGATTGATTTATGAATTTATCTGATGAAACTACTACACTTTGTTGTaAACCTAGATGGGTATTGGGAA

GAAGTGGAAGGAGATACTTGATGTCACTGACAAGATATCTTTCACTAACCATGTAATTACTACTTCCCCA

CGTAAAAAGCTAATAAATCATCCTTTTGTTAGTTCCTTTTTAAACTGTGGTCTAAATATATGCAGGATGA

TGCAAGAAGAAGTCGATTTAGTGTCTAA

The R-o-18 allele of BraA.eIF(iso)4E.c which TuMV can use in *B. rapa* and confers susceptibility on plants has the following mRNA sequence:

(SEQ ID No. 56)
AUGGCGACAGAGGAUGUGAACGAAGCCCUUGCGGCGGCGGAGGUAACGGCGAUAGAAUCGACGGAGAAGC

AGCAGCCUCCUCACAAGCUCGAAAGAAAGUGGAGUCUCUGGUUCGAUAACCAAUCGAAACCCAAGCAAGG

CGCCGCCUGGGGAGUUUCCCUCCGUAAAGCAUGUACCUUCGAUACCGUCGAAGACUUCUGGGGUUUGCAC

GAGACUAUCUUCGUUCCCAGCAGAUUGACACCCAACGCUGACAUUCACAUGUUCAAAGCUGGUGUUGAGC

CCAAGUGGGAAGAUCCUGAGUGUGCUAACGGCGGAAAGUGGACUUAUGUUGUUACCAACAACAGGAAGCA

AGCUUUAGACAAGGCUUGGCUUGAAACUUUGAUGGCUUUAGUUGGAGAGCAGUUUGAUGAGGCAGAUGAG

AUCUGUGGUGUGGUUGCUAGUGUCCGCCAAAAGCAAGACAAGCUCUCCUUGUGGACUAGGACUAAAUCUA

AUGAAGCUGUUCUGAUGGGUAUUGGGAAGAAGUGGAAGGAGAUACUUGAUGUCACUGACAAGAUAUCUUU

CACUAACCAUGAUGAUGCAAGAAGAAGUCGAUUUAGUGUCUAA

The R-o-18 allele of BraA.eIF(iso)4E.c which TuMV can use in *B. rapa* and confers susceptibility on plants codes for the following polypeptide sequence:

(SEQ ID No. 57)
MATEDVNEALAAAEVTAIESTEKQQPPHKLERKWSLWFDNQSKPKQGAAWGVSLRKACTFDTVEDFWGLH

ETIFVPSRLTPNADIHMFKAGVEPKWEDPECANGGKWTYVVTNNRKQALDKAWLETLMALVGEQFDEADE

ICGVVASVRQKQDKLSLWTRTKSNEAVLMGIGKKWKEILDVTDKISFTNHDDARRSRFSV.

RLR22BraA.eIF(iso)4E.c

The RLR22 allele of BraA.eIF(iso)4E.c located on chromosome A8 which TuMV cannot use in *B. rapa* and is necessary for resistance has the following genomic DNA sequence (exons 1 to 5, with the introns shown in bold):

(SEQ ID No. 58)
ATGGCGACAGAGGATGTGAACGAAGCCCTTGCGGCGGCGGAGGTAACGGCGATAGAATCGACGGAGAAGC

AGCAGCCTCCTCACAAGCTCGAAAGAAAGTGGAGTTTCTGGTTCGATAACCAATCGAAACCCAAGCAAGG

CGCCGCCTGGGGAGCTTCCCTCCGTAAAGCATGTACCTTCGATACCGTCGAAGACTTCTGGGGGTTTGTC

TTTTTCTTCTTCGATCTAAGATTTTCTGTGAAGTTATACTAATAGGGGTGTGTGTATTGTTGCAGTTTGC

ACGAGACTATCTTCGTTCCCAGCAGATTGATACCCAACGCTGACATTCACATGTTCAAAGCTGGTGTTGA

GCCCAAGTGGGAAGATCCTGAGTGTGCTAACGGCGGAAAGTGGACTTATGTTGTTACCAACAACAGGAAG

CAAGCTTTAGACAAGGCTTGGCTTGAAACTGTACTCTTCTTCTTCTTCTAACCCTTTTTACTCTTCTGTT

TTCTGACTTAATAATTTTATCTCTTGTGTTTGGCAGTTGATGGCTTTAGTTGGAGAGCAGTTTGATGAGG

CAGATGAGATCTGTGGTGTGGTTGCTAGTGTCCGCCCAAAGCAAGACAAGCTCTCCTTGTGGACTAGGAC

TAAATCTAATGAAGCTGTTCTGGTATCATGCTTCTCTTCTCCCTTATATATGTTTGTTTGACAGTTTTTT

AAACCACCTTTTGATACTTTGCTGACAGTATAATCATAAGCTATATTTGCCAAAGGATATGTTAGTATGT

CAAAGATGGTTTATGAATCTATATATCTGATGAAATTGTTGTTTGTTGTTTGTTTATTGTTATTATGTTT

TATATTGGTTTATGATCCTATCTGATGAGATTTCTACTCTGCTATATATTTAGATTGGTTTATGAATTTA

TCTGACGAAACTAATACACTTTGTTTGTAAACCTAGATGGGTATTGGGAAGAAGTGGAAGGAGATACTTG

ATGTCACCGACAAGATATCTTTCACTAACCATGTAATTACTACTTCCCCACGTAAAAAGCTAATCAATCA

TCCTTTTGTTAGTGCCTTTTTAAACTGTGGTCTATGTATATGCAGGATGATGCAAGAAGAAGTCGATTTA

GTGTCTGA

The RLR22 allele of BraA.eIF(iso)4E.c which TuMV cannot use in *B. rapa* and is necessary for resistance has the following mRNA sequence:

(SEQ ID No. 59)
AUGGCGACAGAGGAUGUGAACGAAGCCCUUGCGGCGGCGGAGGUAACGGCGAUAGAAUCGACGGAGAAGC

AGCAGCCUCCUCACAAGCUCGAAAGAAAGUGGAGUUUCUGGUUCGAUAACCAAUCGAAACCCAAGCAAGG

CGCCGCCUGGGGAGCUUCCCUCCGUAAAGCAUGUACCUUCGAUACCGUCGAAGACUUCUGGGGUUUGCAC

GAGACUAUCUUCGUUCCCAGCAGAUUGAUACCCAACGCUGACAUUCACAUGUUCAAAGCUGGUGUUGAGC

CCAAGUGGGAAGAUCCUGAGUGUGCUAACGGCGGAAAGUGGACUUAUGUUGUUACCAACAACAGGAAGCA

AGCUUUAGACAAGGCUUGGCUUGAAACUUUGAUGGCUUUAGUUGGAGAGCAGUUUGAUGAGGCAGAUGAG

AUCUGUGGUGUGGUUGCUAGUGUCCGCCCAAAGCAAGACAAGCUCUCCUUGUGGACUAGGACUAAAUCUA

AUGAAGCUGUUCUGAUGGGUAUUGGGAAGAAGUGGAAGGAGAUACUUGAUGUCACCGACAAGAUAUCUUU

CACUAACCAUGAUGAUGCAAGAAGAAGUCGAUUUAGUGUCUGA

The RLR22 allele of BraA.eIF(iso)4E.c which TuMV cannot use in *B. rapa* and necessary for resistance codes for the following polypeptide sequence:

(SEQ ID No. 60)
MATEDVNEALAAAEVTAIESTEKQQPPHKLERKWSFWFDNQSKPKQGAAWGASLRKACTFDTVEDFWGLH

ETIFVPSRLIPNADIHMFKAGVEPKWEDPECANGGKWTYVVTNNRKQALDKAWLETLMALVGEQFDEADE

ICGVVASVRPKQDKLSLWTRTKSNEAVLMGIGKKWKEILDVTDKISFTNHDDARRSRFSV.

Accordingly, in a tenth aspect, there is provided an isolated nucleic acid sequence encoding a plant eukaryotic translation initiation factor 4E (eIF4E), or an isoform thereof (eIF(iso)4E), wherein the eIF4E or eIF(iso)4E is non-functional for a virus, and wherein the nucleic acid sequence comprises a nucleotide sequence substantially as set out in SEQ ID No: 4, 5, 7, 9, 34, 35, 37, 38, 40, 41, 43, 44, 46, 47, 49, 50, 52, 53, 58 or 59, or a variant or fragment thereof.

In an eleventh aspect, there is provided an isolated plant eukaryotic translation initiation factor 4E (eIF4E) variant, or an isoform thereof (eIF(iso)4E), which is non-functional for a virus, wherein the eIF4E or eIF(iso)4E protein variant comprises an amino acid sequence substantially as set out in SEQ ID No: 6, 8, 10, 36, 39, 42, 45, 48, 51, 54 or 60, or a variant or fragment thereof.

It will be appreciated that the vector of the third aspect, the host cell of the fourth aspect, the method of any one of the fifth, sixth or eighth aspects, the use of the seventh aspect or the plant of the ninth aspect may comprise any of the sequences described herein which are non-functional for a virus, i.e. as defined in the tenth aspect. For example, in one embodiment, the vectors, cells, methods, uses or plants of the invention may comprise a nucleotide sequence substantially as set out in SEQ ID No: 4, 5, 7, 9, 34, 35, 37, 38, 40, 41, 43, 44, 46, 47, 49, 50, 52, 53, 58 or 59, or a variant or fragment thereof.

In another embodiment, the vectors, cells, methods, uses or plants of the invention may comprise an eIF4E or eIF(iso)4E protein variant, as defined in the eleventh aspect. Preferably, therefore, the vectors, cells, methods, uses or plants comprise an eIF4E or eIF(iso)4E protein variant which comprises an amino acid sequence substantially as set out in SEQ ID No: 6, 8, 10, 36, 39, 42, 45, 48, 51, 54 or 60, or a variant or fragment thereof.

It is preferred that the vectors, cells, methods, uses or plants of the invention comprise the use of a nucleotide sequence substantially as set out in SEQ ID No: 58 or 59, or a variant or fragment thereof, or the use of an eIF4E or eIF(iso)4E protein variant which comprises an amino acid sequence substantially as set out in SEQ ID No: 60, or a variant or fragment thereof.

It will be appreciated that the invention extends to any nucleic acid or peptide or variant, derivative or analogue thereof, which comprises substantially the amino acid or nucleic acid sequences of any of the sequences referred to herein, including (functional) variants or (functional) fragments thereof. The terms "substantially the amino acid/polynucleotide/polypeptide sequence", "(functional) variant" and "(functional) fragment", can be a sequence that has at least 40% sequence identity with the amino acid/polynucleotide/polypeptide sequences of any one of the sequences referred to herein.

Amino acid/polynucleotide/polypeptide sequences with a sequence identity which is greater than 65%, more preferably greater than 70%, even more preferably greater than 75%, and still more preferably greater than 80% sequence identity to any of the sequences referred to are also envisaged. Preferably, the amino acid/polynucleotide/polypeptide sequence has at least 85% identity with any of the sequences referred to, more preferably at least 90% identity, even more preferably at least 92% identity, even more preferably at least 95% identity, even more preferably at least 97% identity, even more preferably at least 98% identity and, most preferably at least 99% identity with any of the sequences referred to herein.

The skilled technician will appreciate how to calculate the percentage identity between two amino acid/polynucleotide/polypeptide sequences. In order to calculate the percentage identity between two amino acid/polynucleotide/polypeptide sequences, an alignment of the two sequences must first be prepared, followed by calculation of the sequence identity value. The percentage identity for two sequences may take different values depending on:—(i) the method used to align the sequences, for example, ClustalW, BLAST, FASTA, Smith-Waterman (implemented in different programs), or structural alignment from 3D comparison; and (ii) the parameters used by the alignment method, for example, local vs global alignment, the pair-score matrix used (e.g. BLOSUM62, PAM250, Gonnet etc.), and gap-penalty, e.g. functional form and constants.

Having made the alignment, there are many different ways of calculating percentage identity between the two sequences. For example, one may divide the number of identities by: (i) the length of shortest sequence; (ii) the length of alignment; (iii) the mean length of sequence; (iv) the number of non-gap positions; or (iv) the number of equivalenced positions excluding overhangs. Furthermore, it will be appreciated that percentage identity is also strongly length dependent. Therefore, the shorter a pair of sequences is, the higher the sequence identity one may expect to occur by chance.

Hence, it will be appreciated that the accurate alignment of protein or DNA sequences is a complex process. The popular multiple alignment program ClustalW (Thompson et al., 1994, Nucleic Acids Research, 22, 4673-4680; Thompson et al., 1997, Nucleic Acids Research, 24, 4876-4882) is a preferred way for generating multiple alignments of proteins or DNA in accordance with the invention. Suitable parameters for ClustalW may be as follows: For DNA alignments: Gap Open Penalty=15.0, Gap Extension Penalty=6.66, and Matrix=Identity. For protein alignments: Gap Open Penalty=10.0, Gap Extension Penalty=0.2, and Matrix=Gonnet. For DNA and Protein alignments: ENDGAP=−1, and GAPDIST=4. Those skilled in the art will be aware that it may be necessary to vary these and other parameters for optimal sequence alignment.

Preferably, calculation of percentage identities between two amino acid/polynucleotide/polypeptide sequences may then be calculated from such an alignment as (N/T)*100, where N is the number of positions at which the sequences share an identical residue, and T is the total number of positions compared including gaps but excluding overhangs. Hence, a most preferred method for calculating percentage identity between two sequences comprises (i) preparing a sequence alignment using the ClustalW program using a suitable set of parameters, for example, as set out above; and (ii) inserting the values of N and T into the following formula:—Sequence Identity=(N/T)*100.

Alternative methods for identifying similar sequences will be known to those skilled in the art. For example, a substantially similar nucleotide sequence will be encoded by a sequence which hybridizes to the sequences shown in SEQ ID No's: 1, 2, 4, 5, 7 or 9, or their complements under stringent conditions. By stringent conditions, we mean the nucleotide hybridises to filter-bound DNA or RNA in 3× sodium chloride/sodium citrate (SSC) at approximately 45° C. followed by at least one wash in 0.2×SSC/0.1% SDS at approximately 20-65° C. Alternatively, a substantially similar polypeptide may differ by at least 1, but less than 5, 10, 20, 50 or 100 amino acids from the sequences shown in SEQ ID No: 3, 6, 8 or 10. A skilled technician will be familiar with highly sensitive techniques for identifying single nucleotide variations or mutations in a nucleic acid sequence.

Due to the degeneracy of the genetic code, it is clear that any nucleic acid sequence described herein could be varied or changed without substantially affecting the sequence of the protein encoded thereby, to provide a (functional) variant thereof. Suitable nucleotide variants are those having a sequence altered by the substitution of different codons that encode the same amino acid within the sequence, thus producing a silent change. Other suitable variants are those having homologous nucleotide sequences but comprising all, or portions of sequence, which are altered by the substitution of different codons that encode an amino acid with a side chain of similar biophysical properties to the amino acid it substitutes, to produce a conservative change. For example small non-polar, hydrophobic amino acids include glycine, alanine, leucine, isoleucine, valine, proline, and methionine. Large non-polar, hydrophobic amino acids include phenylalanine, tryptophan and tyrosine. The polar neutral amino acids include serine, threonine, cysteine, asparagine and glutamine. The positively charged (basic) amino acids include lysine, arginine and histidine. The negatively charged (acidic) amino acids include aspartic acid and glutamic acid. It will therefore be appreciated which amino acids may be replaced with an amino acid having similar biophysical properties, and the skilled technician will known the nucleotide sequences encoding these amino acids.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying diagrammatic drawings, in which:—

FIG. 1 shows an electrophoretic gel on which RT-PCT products of the *Brassica rapa* eIF(iso)4E mRNA and *Arabidopsis thaliana* eIF(iso)4E and eIF(iso)4E mRNA have been separated. R-o-18 corresponds to a *B. rapa* line which is susceptible to infection by TuMV, whereas *B. rapa* line RLR22 is resistant to infection by TuMV. The mRNA from virus-resistant line RLR22 (SEQ ID No. 5) is larger than that of the susceptible line R-o-18 (SEQ ID No. 2). Col-0 eIF4E and Col-0 eIF(iso)4E are controls and correspond to wild-type *Arabidopsis thaliana* eIF4E and eIF(iso)4E, respectively;

Figure 4:
Figure 5:
Figure 6:
Figure 7:
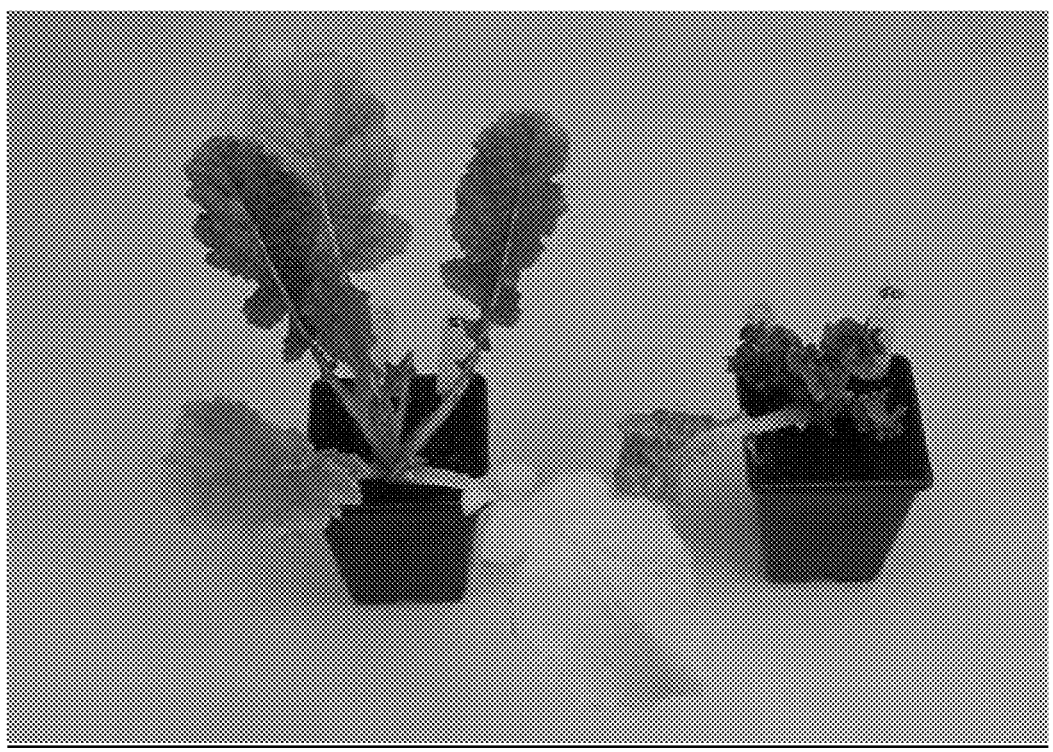
Figure 8:
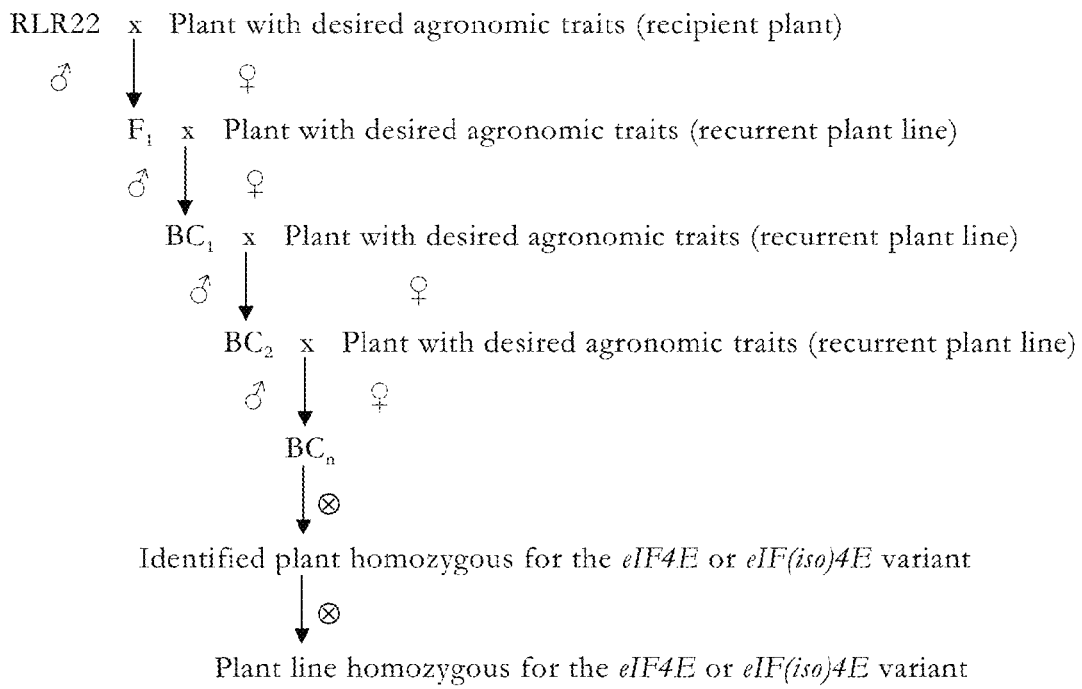
Figure 9:
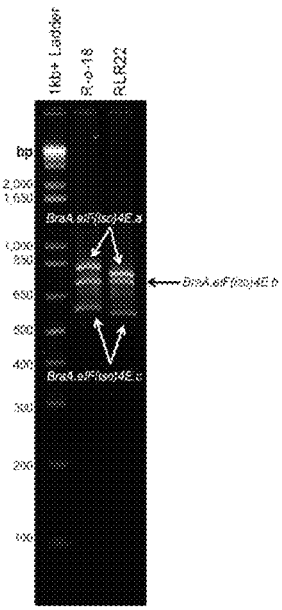

FIG. 4 is a schematic representation of one embodiment (the most common variant) of the mRNA of *Brassica rapa* eIF(iso)4E.a in line RLR22 (SEQ ID NO. 5), which is resistant to viral infection. The start and stop codons are represented by arrows. The mis-splicing results in the retention of the whole of intron 1 in the mature message RNA and the introduction of a premature stop codon indicated by the first vertical arrow on the left (in the intron between exons 1 and 2);

FIG. 5 is a schematic representation of another embodiment of the mRNA of *Brassica rapa* eIF(iso)4E.a in line RLR22 (SED ID No. 7), which is resistant to viral infection. The start and stop codons are represented by arrows. The mis-splicing results in partial removal of the intron, with only the first 48 nucleotides removed;

FIG. 6 is a schematic representation of another embodiment of the mRNA of *Brassica rapa* eIF(iso)4E.a in line RLR22 (SEQ ID No. 9), which is resistant to viral infection. The start and stop codons are represented by arrows. The mis-splicing results in the excision of the last three nucleotides of exon 1 along with the whole of intron 1;

FIG. 7 shows a photo of a plant having a modification in intron 1 of *Brassica rapa* eIF(iso)4E.a in line RLR22, which is resistant to TuMV infection (left) and a *Brassica rapa* plant lacking this modification which is extremely susceptible to TuMV (right);

FIG. 8 is a schematic representation of a breeding program to generate a plant line that is homozygous for the eIF4E or eIF(iso)4E variant of the invention; and FIG. 9 shows an electrophoretic gel showing the PCR products obtained from DNA of plants R-o-18 and RLR22 using primers BR2 and BR14.

EXAMPLES

Example 1—Analysis of eIF(Iso)4E Sequence Conferring Virus-Resistance and Isolation of a First Locus Conferring Virus-Resistance, Retr01

The inventor investigated in *B. rapa* with the aim of identifying genes and mechanisms involved in conferring plant resistance against TuMV.

Materials and Methods

The *B. rapa* line R-o-18 is an inbred line susceptible to infection by TuMV. Line RLR22, however, has broad-spectrum resistance to all TuMV isolates tested so far. Total genomic DNA was extracted from young leaves of lines R-o-18 and RLR22 using a DNeasy plant mini kit (Qiagen) followed by amplification using the GenomiPhi system (GE Healthcare). The majority of the genomic coding region of the BraA.eIF(iso)4E.a gene was amplified with standard PCR using Taq DNA polymerase (Invitrogen) and the following primers:—

```
                                        (SEQ ID No. 11)
    PCR1     (ATGGCGACAGAGGATGTGAACG)
    and (SEQ ID No. 12)
    PCR2     (TCTCCTTCCACTTCTTCCCAATAC).
```

The largest amplification product, corresponding to the eIF(iso)4E locus a, was purified using agarose gels and the Qiaquick gel extraction kit (Qiagen). The PCR products were then labelled with $^{32}$P dCTP using the RediPrime™II DNA labelling system (GE Healthcare) to form probes. These radio-labelled probes were then hybridised to filters printed with 36864 colonies of the JBr BAC library (line R-o-18) or a fosmid library of line RLR22 (Warwick Plant Genome Libraries, UK) to identify colonies containing plasmids with BraA.eIF(iso)4E.a (JBr043O19 and RLR021G13, respectively). Sections of these plasmids were sequenced, using the BigDye Terminator system and an ABI Prism 3130xl Genetics Analyzer (Applied Biosystems), in a step-wise manner to determine the complete genomic sequence of the two alleles.

Total RNA was extracted from young leaves of both plant lines using an RNeasy kit (Qiagen). Some samples of total RNA were treated with DNaseI (Roche) to remove any remnants of genomic DNA. The RT-FOR and RT-REV primers encompass the complete coding region of the BraA.eIF(iso)4E.a gene (start and stop codons are shown in bold; an adapter for cloning is in italics).

```
RT-FOR:
                                              (SEQ ID No. 13)
AAAAAGCAGGCT CGATGGCGACAGAGGATG

RT-REV (R-o-18):
                                              (SEQ ID No. 14)
AGAAAGCTGGGT TCAGACAGTGAACCTAGTTCTTC

RT-REV (RLR22):
                                              (SEQ ID No. 15)
AGAAAGCTGGGT TCAGACAGTGAACCGAGTTCTTC
```

Total RNA (about 10 µg RNA, with and without DNaseI treatment) was converted to cDNA with standard reverse transcription reactions using Superscript II (Invitrogen) and the appropriate RT-REV primer. cDNA was amplified with standard PCR using Taq DNA polymerase (Invitrogen) or KOD polymerase (Novagen) and the appropriate RT-FOR and RT-REV primer combination. RT-PCR products were separated using agarose gel electrophoresis, and extracted from the gel using a Qiaquick gel extraction kit (Qiagen). Products were cloned into plasmid pDONR221 using BP clonase (Invitrogen). Plasmids were amplified using the TempliPhi reaction (GE Healthcare) and then sequenced.

Results

The inventor identified a *B. rapa* line, RLR22, which has resistance against a range of TuMV isolates from different parts of the world and representing different genetic groups. FIG. 8 illustrates that a plant homozygous for the RLR22 allele of eIF(iso)4E.a is resistant to TuMV infection (left) whereas plants homozygous, or heterozygous for the *B. rapa* R-o-18 allele of eIF(iso)4E.a, are susceptible to TuMV infection (right).

Firstly, the inventor found that the viral resistance phenotype is linked to the eIF(iso)E locus. Using a cross between a susceptible line (R-o-18) and the resistant line (RLR22), the inventor confirmed that *B. rapa* contains three eIF(iso)4E loci.

Figure 1:
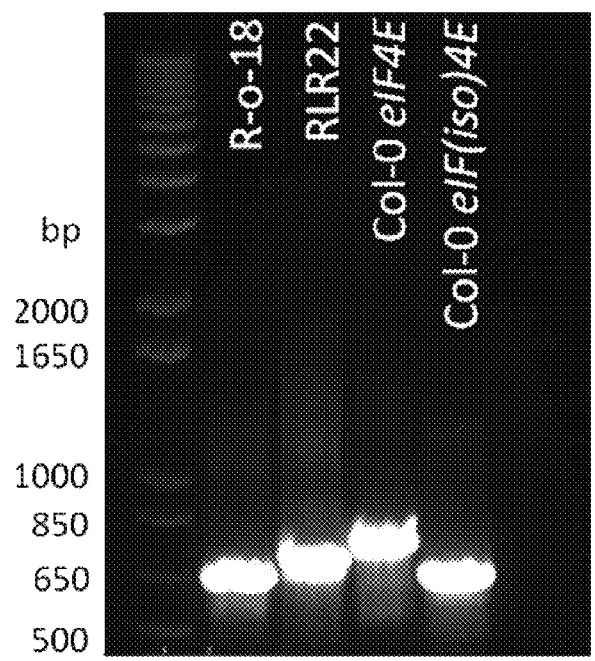
Figure 2:
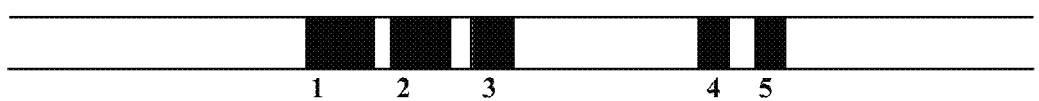
FIG. 2 is a schematic representation of the gene encoding *Brassica rapa* eIF(iso)4E.a. The exons are shown as black boxes, and are numbered, and the introns are shown as white boxes and are not numbered.

Secondly, the sequences of genomic and mRNA versions of BraA.eIF(iso)4E.a in line R-o-18 and RLR22 were compared. FIG. 1 shows an electrophoretic gel of RT-PCR products of the *Brassica rapa* eIF(iso)4E.a mRNA, and as controls, *Arabidopsis thaliana* eIF4E and eIF(iso)4E mRNA. As can be seen in the gel, the mRNA of BraA.eIF (iso)4E.a from virus-resistant line, RLR22, is larger than the mRNA of BraA.eIF(iso)4E.a obtained from the infected line, R-o-18.

Figure 3:
FIG. 3 is a schematic representation of the mRNA of *Brassica rapa* eIF(iso)4E.a in line R-o-18, which can be infected by TuMV. The arrow above exon 1 corresponds to the start codon, and the arrow above exon 5 corresponds to the stop codon.

The genomic sequence of BraA.eIF(iso)4E.a in line R-o-18 is provided as SEQ ID No. 1, and the genomic sequence of RLR22 is provided as SEQ ID No. 4. Following sequencing of the BraA.eIF(iso)4E.a, the inventor has found that the two alleles (in R-o-18 and RLR22) differ by a base insertion/deletion (i.e. an "indel") at the exon/intron junction. In the virus-susceptible line R-o-18, a single mRNA sequence of the eIF(iso)4E.a allele was found and the mRNA sequence is provided as SEQ ID No. 2. The mRNA was capable of producing a full-length protein, as represented by the schematic shown in FIG. 3, and the protein sequence is provided as SEQ ID No. 3.

However, in the virus-resistant line RLR22, several splice variants of mRNA of eIF(iso)4E.a were found. The mRNA of eIF(iso)4E.a mainly consisted of a product (denoted as SEQ ID No. 5) with the first intron still present in the expressed DNA, forming a longer eIF(iso)4E.a protein, and this explains why the fragment is larger in the RLR22 shown in FIG. 1. Other rarer splice variants of eIF(iso)4E.a were also identified: SEQ ID No. 7 had most of the first intron removed except for the 3' terminal 15 bases which were retained, as represented in FIG. 5. SEQ ID No. 9 had all of the first intron removed, and also the 3' terminal 3 bases of exon 1 removed, as represented in FIG. 6. None of these splicing variants would be capable of producing a full-length 'correct' eIF(iso)4E.a protein, i.e. producing the full length protein as if splicing had occurred correctly, as in line R-o-18, which is susceptible to viral infection. The amino acid sequences translated from SEQ ID Nos. 5, 7 and 9 are shown as SEQ ID Nos. 6, 8 and 10, respectively. The inventor believes that none of the modified proteins would be functional for TuMV.

Until now, reported recessive resistance to potyviruses based on eIF(iso)4E have arisen through base changes only in the coding region of the gene (exons), causing changed protein sequences (altered amino acid residues or premature chain termination). In the case of virus-resistant line RLR22, however, the resistance is surprisingly related to alterations in a non-coding region of the gene (introns). The inventor has shown that the "indel" in the eIF(iso)4E.a allele would disrupt correct splicing in line RLR22 and result in no (or greatly reduced) functional eIF(iso)4Ea protein for viral genome translation, and ultimately viral infection. The inventors have named the allele, BraA.eIF(iso)4E.a, from the virus-resistant line, RLR22, retr01.

Example 2—Breeding Plants Resistant to TuMV Infection

*B. rapa* plants that are resistant to TuMV may be obtained from the following breeding programme and the breeding programme is illustrated in FIG. 8.

Referring to FIG. 8, the recipient *B. rapa* plants with desired agronomic traits are crossed with a virus-resistant RLR22 plant and the progeny (F$_1$) are backcrossed with the recipient parent (recurrent) plant line. Molecular techniques (e.g. PCR and sequencing or other specific PCR-based methods to distinguish BraA.eIF(iso)4E.a alleles) are used to ensure that the allele of BraA.eIF(iso)4E.a derived from RLR22 (which confers virus resistance) is present in the non-recurrent plants in each cross. Finally, plants derived from the backcrossing programme that possessed the RLR22 allele of BraA.eIF(iso)4E.a are selfed (i.e. self-pollinated). Plants in the subsequent generation that are homozygous for the RLR22 allele of BraA.eIF(iso)4E.a are identified by molecular techniques as described above.

For breeding $F_1$ hybrid plants with the viral resistance, two plant lines derived from separate backcrossing programmes must be homozygous for the eIF4E or eIF(iso)4E of the first aspect. These lines are then crossed to generate the $F_1$ hybrid which would in turn be homozygous for the eIF4E or eIF(iso)4E of the first aspect.

Example 3—Breeding Plants Resistant to Potyvirus Infection

Plants that are resistant to a particular potyvirus may be obtained from the following breeding programme.

The recipient plant is crossed with plants defective for splicing of eIF4E and/or eIF(iso)4E and the progeny is backcrossed with the recipient parent (recurrent) plant line. Molecular techniques (PCR and sequencing or other specific PCR-based tests) are used to ensure that the allele(s) of eIF4E and/or eIF(so)4E that is/are defective in splicing and conferring resistance is/are present in the non-recurrent plants for each cross. Plants derived from the backcrossing programme possessing the eIF4E and/or eIF(so)4E allele that is/are defective in splicing and conferring resistance are selfed. Plants in the subsequent generation that are homozygous for the allele of eIF4E and/or eIF(so)4E that is/are defective in splicing are identified using the molecular techniques described above. Finally these plants are selfed to give lines/families that are homozygous for the desired eIF4E/eIF(so)4E alleles.

For breeding $F_1$ hybrid plants with the viral resistance, two plant lines derived from separate backcrossing programmes must be homozygous for the eIF4E or eIF(iso)4E of the first aspect. These lines are then crossed to generate the $F_1$ hybrid, which would in turn be homozygous for the eIF4E or eIF(iso)4E of the first aspect.

Example 4—Isolation of a Second Locus Conferring Virus-Resistance, ConTR01

The scenario described in Examples 1-3 is sufficient to explain virus resistance in plants that possess just one copy of eIF4E and/or eIF(so)4E, which a particular virus is able to utilise to complete its life-cycle. However, some plants have multiple copies/loci of one, or both of these two genes. For example, Brassica rapa has three copies of both eIF4E and eIF(iso)4E, and a virus may be able to use any of these genes to complete its life cycle. Thus, in order to confer virus resistance in plants having multiple copies/loci of eIF4E and/or eIF(so)4E, it is necessary that the alleles of eIF4E and/or eIF(so)4E at each of these other loci are non-functional for the virus.

Using the cross discussed above between the B. rapa TuMV-susceptible line R-o-18 and the TuMV-resistant line RLR22, a $B_1$ plant that was homozygous for the RLR22 allele of BraA.eIF(iso)4E.a and the RLR22 allele of BraA.eIF4E.c, but heterozygous at the BraA.eIF(iso)4E.c locus, was identified. $B_1S_1$ plants derived from this particular individual were then phenotyped and genotyped. Plants homozygous for the RLR22 allele of BraA.eIF(iso)4E.c were completely resistant to systemic spread of TuMV, heterozygotes were only slightly susceptible to virus infection, whereas plants that were homozygous for the R-o-18 allele of BraA.eIF(iso)4E.c were completely susceptible.

The second locus involved in the broad-spectrum resistance to TuMV in B. rapa has now been identified as BraA.eIF(iso)4E.c on chromosome A8, and is referred to herein as ConTR01. This confirms the necessity for the second gene (ConTR01, the RLR22 allele of BraA.eIF(iso)4E.c) in addition to retr01 (the RLR22 allele of BraA.eIF(iso)4E.a) for broad-spectrum resistance to TuMV in B. rapa, and demonstrates the importance of more than one gene to confer resistance in plants where viruses are able to utilise multiple copies/loci of eIF4E and/or eIF(iso)4E.

Materials and Methods

Total genomic DNA was extracted from young leaves of lines R-o-18 and RLR22 using a DNeasy plant mini kit (Qiagen) followed by amplification using the GenomiPhi system (GE Healthcare). The genomic coding region of the BraA.eIF4E.a, BraA.eIF4E.b (R-o-18 only), BraA.eIF4E.c, BraA.eIF(iso)4E.b and BraA.eIF(iso)4E.c genes were amplified with standard PCR using Taq DNA polymerase (Invitrogen) and the primers listed below. Sections of these products were sequenced, using the BigDye Terminator system and an ABI Prism 3130xl Genetics Analyzer (Applied Biosystems), in a step-wise manner to determine the complete genomic sequence of the alleles. BraA.eIF4E.b was not sequenced from RLR22, as it is non-functional. A summary of sequences obtained are listed in Table 1.

TABLE 1

Sequencing of eIF4E and eIF(iso)4E alleles in Brassica rapa lines RLR22 and R-o-18

| Allele | Sequence obtained for plant line | |
|---|---|---|
| | RLR22 | R-o-18 |
| BraA.eIF4E.a | Yes | Yes |
| BraA.eIF4E.b | No | Yes |
| BraA.eIF4E.c | Yes | Yes |
| BraA.eIF(iso)4E.b | Yes | Yes |
| BraA.eIF(iso)4E.c | Yes | Yes |

Primers Used to Amplify or Sequence eIF4E and eIF(iso)4E Alleles from Brassica rapa Lines R-o-18 and RLR22:

```
R-o-18 BraA.eIF4E.a:
                                   (SEQ ID No. 16)
AAAAAGCAGGCTTTTGGTCTGCAGTTATGTTATTAG

REVERSE (BR58):
                                   (SEQ ID No. 17)
AGAAAGCTGGGTAAAAAGGCTTGCGAGTCA

R-o-18 BraA.eIF4E.b:
FORWARD (BR71):
                                   (SEQ ID No. 18)
CAATGGCGGTAGAAGACACT

REVERSE (BR50):
                                   (SEQ ID No. 19)
AGTTGAGTTTTTCTTCTTAC

R-o-18 BraA.eIF4E.c:
FORWARD (BR59):
                                   (SEQ ID No. 20)
AAAAAGCAGGCTTAGGACAAATGATATGGGGAGAGT

REVERSE (BR60):
                                   (SEQ ID No. 21)
AGAAAGCTGGGTAGCTTGGCGACCTTTTGA

R-o-18 BraA.eIF(iso)4E.b:
FORWARD (BR73):
                                   (SEQ ID No. 22)
TGAAAGGGGCGAAAAACACAT
```

-continued

```
REVERSE (BR74):
                                       (SEQ ID No. 23)
GCAAACCGACAAAATAAGGAAGAA

R-o-18 BraA.eIF(iso)4E.c:
FORWARD (BR63):
                                       (SEQ ID No. 24)
AAAAAGCAGGCTTTTTTAAGAATGGAGGGAGTAT REVERSE (BR64):
                                       (SEQ ID No. 25)
AGAAAGCTGGGTGAAGCGCGGGTCAAAAT RLR22 BraA.eIF4E.a:
FORWARD (BR68):
                                       (SEQ ID No. 26)
AAAAAGCAGGCTTTTGGTCTGCAATTATCTTATTAG REVERSE (BR58):
                                       (SEQ ID No. 27)
AGAAAGCTGGGTAAAAAGGCTTGCGAGTCA RLR22 BraA.eIF4E.c:
FORWARD (59):
                                       (SEQ ID No. 28)
AAAAAGCAGGCTTAGGACAAATGATATGGGAGAGT REVERSE (60):
                                       (SEQ ID No. 29)
AGAAAGCTGGGTAGCTTGGCGACCTTTTGA RLR22 BraA.eIF(iso)4E.b:
FORWARD (BR73):
                                       (SEQ ID No. 30)
TGAAAGGGGCGAAAAACACAT REVERSE (BR74):
                                       (SEQ ID No. 31)
GCAAACCGACAAAATAAGGAAGAA RLR22 BraA.eIF(iso)4E.c:
FORWARD (BR80):
                                       (SEQ ID No. 32)
AAAAAGCAGGCTCGAAGAAGTCCGCATAAAGC REVERSE (BR81):
                                       (SEQ ID No. 33)
AGAAAGCTGGGTACCCGTCCGTGGATTAAATA
```

Example 5—Identification of the Second Gene (ConTR01) Involved in the Broad-Spectrum Resistance

*B. rapa* line R-o-18 is an inbred line susceptible to TuMV. Line RLR22, resistant to TuMV, has broad-spectrum resistance to all TuMV isolates tested so far (Walsh et al. 2002, European Journal of Plant Pathology 108, 15-20). From the cross between the *B. rapa* TuMV-susceptible line R-o-18 and the TuMV-resistant line RLR22 (Rusholme et al. 2007, *Journal of General Virology* 88, 3177-3186). $B_1$ plant 16 was identified as homozygous for the RLR22 alleles of BraA.eIF(iso)4E.a and BraA.eIF4E.c, but heterozygous at the BraA.eIF(iso)4E.c locus. RLR22 and R-o-18 have the same allele at the BraA.eIF(iso)4E.b locus and the R-o-18 allele at BraA.eIF4E.b is a pseudogene giving a much truncated polypeptide, and so these alleles were not determined for this plant.

$B_1S_1$ seed derived from $B_1$ plant 16 was sown. Total genomic DNA was extracted from young leaves of the plants that germinated using a DNeasy plant mini kit (Qiagen), followed by amplification using the GenomiPhi system (GE Healthcare). Plants were then genotyped at the BraA.eIF(iso)4E.c locus using the primers BR2 (TCTCCTTCCACT-TCTTCCCAATAC—SEQ ID No: 61) and BR14 (TAGA-CAAGGCTTGGCTTGAAACTG—SEQ ID No: 62). These primers produce products of three sizes (see FIG. 9) for RLR22 and three sizes for R-o-18. The largest product corresponds to BraA.eIF(iso)4E.a for both plants, the middle-sized product corresponds to BraA.eIF(iso)4E.b and the smallest product BraA.eIF(iso)4E.c for both plants. The product for the R-o-18 allele of BraA.eIF(iso)4E.c (566 bp) is larger than the product for the RLR22 allele (546 bp) and easily distinguished (see FIG. 9). As can be seen in the gel, the PCR product for BrA.eIF(iso)4Ec from the susceptible plant R-o-18, is bigger than that of the resistant plant RLR22.

The plants were mechanically inoculated with TuMV isolate CDN 1 at the 3-5 leaf stage and infection/resistance phenotypes determined by visual assessment and ELISA as described by Rusholme et al. (2007). The genotypes, phenotypes and ELISA values for the plants are given in Table 2.

TABLE 2

The phenotypes of *Brassica rapa* plants segregating for BraA.eIF(iso)4E.c from $B_1S_1$ family 16, derived from a cross between the Turnip mosaic virus (TuMV)-resistant plant RLR22 and the TuMV-susceptible plant R-o-18

| Genotype of plants at BraA.eIF(iso)4E.c locus (all homozygous for RLR22 allele of BraA.eIF(iso)4E.a and RLR22 allele of BraA.eIF4E.c) | Phenotypes of plants following challenge with TuMV as determined by visual assessment | Mean $A_{405}$ from ELISA on uninoculated leaves |
|---|---|---|
| Heterozygous | Limited/some systemic spread[1] of TuMV | 0.05 |
| Heterozygous | Resistant, no systemic spread of TuMV | 0.02 |
| Homozygous for R-o-18 allele | Susceptible, systemic spread of TuMV | 0.30 |
| Homozygous for RLR22 allele | Resistant, no systemic spread of TuMV | 0.02 |
| Control uninfected plants | No virus inoculated | 0.04 |

[1]Systemic spread = spread of TuMV infection from inoculated to uninoculated leaves.

Plants homozygous for the RLR22 allele of BraA.eIF(iso)4E.c were completely resistant to TuMV, heterozygotes showed either no detectable infection, or were only slightly susceptible with the virus spreading from the inoculated leaves to a limited number of uninoculated leaves but then no further. Plants that were homozygous for the R-o-18 allele of BraA.eIF(iso)4E.c were completely susceptible. The results show that TuMV is able to use the R-o-18 allele of BraA.eIF(iso)4E.c and that plants need to be homozygous for this allele in order to establish a full systemic infection. Results from inoculation of plants that were heterozygous at this locus show that one copy of the R-o-18 allele is not sufficient for TuMV to establish a full-blown systemic infection. Differences between the phenotypes of heterozygotes (not susceptible or limited susceptibility) probably relate to the necessity for the virus to establish a high enough titre in inoculated leaves in order for systemic spread to take place.

Table 3 provides a summary of the ability of TuMV to use the six alleles described herein. BraA.eIF(iso)4E.a is retr01, and BraA.eIF(iso)4E.c is ConTR01.

TABLE 3

The ability of Turnip mosaic virus (TuMV) to use the different eIF4E and eIF(iso)4E alleles in *Brassica rapa* lines RLR22 and R-o-18 to complete its life cycle

| | Ability of TuMV to use allele from *B. rapa* line | |
|---|---|---|
| Allele | RLR22 | R-o-18 |
| BraA.eIF4E.a | No | No |
| BraA.eIF4E.b | No | No |
| BraA.eIF4E.c | No | No |
| BraA.eIF(iso)4E.a | No | Yes |
| BraA.eIF(iso)4E.b | No | No |
| BraA.eIF(iso)4E.c | No | Yes |

SEQUENCE LISTING

```
<160> NUMBER OF SEQ ID NOS: 62

<210> SEQ ID NO 1
<211> LENGTH: 1372
<212> TYPE: DNA
<213> ORGANISM: Brassica rapa

<400> SEQUENCE: 1
atggcgacag aggatgtgaa cgaagccctt gcggcggcgg aagtaccggc aacagagacg      60
acggagaagc agcctgctca caagctcgaa agaaagtgga gtttctggtt cgataaccaa     120
tccaaaccaa agcaaggcgc cgcctgggga gcctcccttc gcaaagccta taccttcgac     180
accgtccaag acttctgggg gtttgtttgt cttctccttt tatttattgt tagcgatctg     240
taaagctaga tcttcttttg cagtttgcac gagactatat tcatccctag caaactgacg     300
ccgaatgctg aaattcacat gttcaaagct ggtgttgagc ctaagtggga agatcctgag     360
tgtgctaatg ggggaaagtg gacttatgtt gtcacctcca accgcaagcc tgctttagac     420
aaggcttggc ttgaaactgt actcctcttc tacctctcct ccttttttct ttttttttgc     480
atctggtaat gacatgtttt ctctgccagt tgatggctct tgtcggagag caatttgatg     540
aggctgatga gatttgtggc gtggttgcta gtgtgcgccc aaagcaggac aagctctcct     600
tgtggacaag gaccaaatct aatgaagctg ttctggtatg atgcttgtct tctctcacta     660
tgtacctttg gtgttgtttg ataactgttt tcttctactt gttatccgtt gcgatgtccc     720
attattgttt gattatcctg ttccaatttt tttgtattgc gtactggtgg tttacgaaga     780
agtgttcttg tacaatatgt tagcgttgtt gaatgtgtta attgcttact atagtaaaac     840
agtttaagct gttgactatg ttaatattct cttcgataca cacacttaga atggataact     900
accttgtttc tttatccttt ggagtttcac cagcttatta tcgatcgaga tactccttct     960
gatttgaatt accattcaag attaatattt atatatattg aaagtatatg tttgtttaac    1020
gatatatcta ttaggcttgc ttttttttagt tcattcgcag tataaacgta gctctattta   1080
ttagaggctt ctctttagaa cttggcagta atgtaatatg tcgaagtgtg gtttatgaat    1140
ctggttgatg atattactaa tttttttgtt tgttattgta aatccagatg ggtattggga    1200
agaagtggaa ggagatactt gatgtcaccg acaagataac tttcactaac catgtaactt    1260
aactttctcc acatagaggc taattatctt ttgttcttct tacgtggctt actaaaatgt    1320
ggtctactta tatatatagg atgattctag aagaactagg ttcactgtct ga            1372

<210> SEQ ID NO 2
<211> LENGTH: 600
<212> TYPE: RNA
<213> ORGANISM: Brassica rapa
```

<400> SEQUENCE: 2

```
auggcgacag aggaugugaa cgaagcccuu gcggcggcgg aaguaccggc aacagagacg      60
acggagaagc agccugcuca caagcucgaa agaaagugga guuucugguu cgauaaccaa     120
uccaaaccaa agcaaggcgc cgccugggga gccucccuuc gcaaagccua uccuucgac      180
accguccaag acuucggggu uugcacgag acuauauuca ucccuagcaa acugacgccg      240
aaugcugaaa ucacauguu caaagcuggu guugagccua aguggaaga uccugagugu      300
gcuaauggggg gaaaguggac uuauguuguc accuccaacc gcaagccugc uuuagacaag     360
gcuuggcuug aaacuuugau ggcucuugc ggagagcaau uugaugaggc ugaugagauu     420
uguggcgugg uugcuagugu gcgcccaaag caggacaagc ucuccuugug acaaggacc     480
aaaucuaaug aagcuguucu gauggguauu gggaagaagu ggaaggagau acuugauguc     540
accgacaaga uaacuuucac uaaccaugau gauucuagaa gaacuagguu cacugucuga    600
```

<210> SEQ ID NO 3
<211> LENGTH: 199
<212> TYPE: PRT
<213> ORGANISM: Brassica rapa

<400> SEQUENCE: 3

```
Met Ala Thr Glu Asp Val Asn Glu Ala Leu Ala Ala Ala Glu Val Pro
1               5                   10                  15
Ala Thr Glu Thr Thr Glu Lys Gln Pro Ala His Lys Leu Glu Arg Lys
                20                  25                  30
Trp Ser Phe Trp Phe Asp Asn Gln Ser Lys Pro Lys Gln Gly Ala Ala
            35                  40                  45
Trp Gly Ala Ser Leu Arg Lys Ala Tyr Thr Phe Asp Thr Val Gln Asp
        50                  55                  60
Phe Trp Gly Leu His Glu Thr Ile Phe Ile Pro Ser Lys Leu Thr Pro
65                  70                  75                  80
Asn Ala Glu Ile His Met Phe Lys Ala Gly Val Glu Pro Lys Trp Glu
                85                  90                  95
Asp Pro Glu Cys Ala Asn Gly Gly Lys Trp Thr Tyr Val Val Thr Ser
            100                 105                 110
Asn Arg Lys Pro Ala Leu Asp Lys Ala Trp Leu Glu Thr Leu Met Ala
        115                 120                 125
Leu Val Gly Glu Gln Phe Asp Glu Ala Asp Glu Ile Cys Gly Val Val
    130                 135                 140
Ala Ser Val Arg Pro Lys Gln Asp Lys Leu Ser Leu Trp Thr Arg Thr
145                 150                 155                 160
Lys Ser Asn Glu Ala Val Leu Met Gly Ile Gly Lys Lys Trp Lys Glu
                165                 170                 175
Ile Leu Asp Val Thr Asp Lys Ile Thr Phe Thr Asn His Asp Asp Ser
            180                 185                 190
Arg Arg Thr Arg Phe Thr Val
        195
```

<210> SEQ ID NO 4
<211> LENGTH: 1321
<212> TYPE: DNA
<213> ORGANISM: Brassica rapa

<400> SEQUENCE: 4

```
atggcgacag aggatgtgaa cgaagccctt gcggcggcgg aagtaccggc aacagagacg      60
```

```
acggagaagc agcctgctga caagctcgaa agaaagtgga gtttctggtt cgataaccaa    120
tccaaaccaa agcaaggcgc cgcctgggga gcctcccttc gcaaagccta taccttcgac    180
accgtccaag acttctgggg ggtttgtttg tcttctcctt ttacttattg ttagcgatct    240
gtaaagctag atcttctttt gcagtttgca cgagactata ttcatcccta gcaaactgac    300
gccgaatgct gaaattcaca tgttcaaagc tggtgttgag cctaagtggg aagatcctga    360
gtgtgctaat ggcggaaagt ggacttttgt tgttacctcc aaccgcaagc ctgctttaga    420
caaggcttgg cttgaaactg tactcatctt ctacctctcc tctttttttt tttaatagtt    480
tagacaattt tgcatctggt aatgacatgt tttatctgcc agttgatggc tcttgtcgga    540
gagcaatttg atgaggctga tgagatctgt ggggtggttg ctagtgtgcg cccaaagcag    600
gacaagctct ccttgtggac aaggaccaaa tctaatgaag ctgttctggt atgatgcttc    660
tcttctctca ctatgtacct tggtgttgt tttcttctac ttgttatccg ttgcgatgtc    720
ccattattgt ttgattatcc tgttccaatt tttctgtttt gcgtactggt ggtttacgaa    780
gaagtatgct tgtacaatat gttagcgttg ttgaatgtgt taattgctta ctatagtaaa    840
acagtttaag ctgttgacta tgttaatatt ctcttcgata cacacactta gaatggataa    900
ctaccttgtt tctttatcct tggagtttc accagcttaa tatatattga agtatatgt     960 ttgttcaacg atatatctat taggcttgct ttttttagtt cattcgcagt ataaacatag   1020
ctctatttat tagaggccat ctcttttagaa cttggcagta ctgtaatatg tcgaagtgtg   1080
gtttatgaat ctggctgatg atattactac tttgttgttt gttattgtaa atccagatgg   1140
gtattgggaa gaagtggaag gagatacttg atgtcaccga caagataact ttcactaacc   1200
atgtaactta actttctcca catagaggct aattatcttt tgttcttctt acgtggctta   1260
ctaaaatgtg gtctacttat atatatagga tgattctaga gaactcggt tcactgtctg    1320 a                                                                    1321

<210> SEQ ID NO 5
<211> LENGTH: 664
<212> TYPE: RNA
<213> ORGANISM: Brassica rapa

<400> SEQUENCE: 5
auggcgacag gaugugugaa cgaagcccuu gcggcggcgg aaguaccggc aacagagacg     60
acggagaagc agccugcuga caagcucgaa agaaagugga guuucugguu cgauaaccaa    120
uccaaaccaa agcaaggcgc cgccugggga gccucccuuc gcaaagccua uaccuucgac    180
accguccaag acuucugggg gguuuguuug ucuucuccuu uuacuuauug uuagcgaucu    240
guaaagcuag aucuucuuuu gcaguuugca cgagacuaua uucaucccua gcaaacugac    300
gccgaaugcu gaaauucaca uguucaaagc uggguguuga gccuagugggg aagauccuga    360 gugugcuaau ggcggaaagu ggacuuuugu uguuaccucc aaccgcaagc cugcuuuaga    420
caaggcuugg cuugaaacuu ugauggcucu ugucggagag caauuugaug aggcugauga    480 gaucugugggg guggguugcua gugugcgccc aaagcaggac aagcucuccu uguggacaag    540
gaccaaaucu aaugaagcug uucgauggg uaugggaag aaguggaagg agauacuuga    600
ugucaccgac aagauaacuu ucacuaacca ugaugauucu agaagaacuc gguucacugu    660
cuga                                                                  664

<210> SEQ ID NO 6
<211> LENGTH: 201
```

-continued

```
<212> TYPE: PRT
<213> ORGANISM: Brassica rapa

<400> SEQUENCE: 6

Met Ala Thr Glu Asp Val Asn Glu Ala Leu Ala Ala Ala Glu Val Pro
1               5                   10                  15

Ala Thr Glu Thr Thr Glu Lys Gln Pro Ala Asp Lys Leu Glu Arg Lys
            20                  25                  30

Trp Ser Phe Trp Phe Asp Asn Gln Ser Lys Pro Lys Gln Gly Ala Ala
        35                  40                  45

Trp Gly Ala Ser Leu Arg Lys Ala Tyr Thr Phe Asp Thr Val Gln Asp
    50                  55                  60

Phe Trp Gly Val Cys Leu Ser Ser Pro Phe Thr Tyr Cys Arg Ser Val
65                  70                  75                  80

Lys Leu Asp Leu Leu Leu Gln Phe Ala Arg Asp Tyr Ile His Pro Gln
                85                  90                  95

Thr Asp Ala Glu Cys Asn Ser His Val Gln Ser Trp Cys Ala Val Gly
            100                 105                 110

Arg Ser Val Cys Trp Arg Lys Val Asp Phe Cys Cys Tyr Leu Gln Pro
        115                 120                 125

Gln Ala Cys Phe Arg Gln Gly Leu Ala Asn Phe Asp Gly Ser Cys Arg
    130                 135                 140

Arg Ala Ile Gly Asp Leu Trp Gly Gly Cys Cys Ala Pro Lys Ala Gly
145                 150                 155                 160

Gln Ala Leu Leu Val Asp Lys Asp Gln Ile Ser Cys Ser Asp Gly Tyr
                165                 170                 175

Trp Glu Glu Val Glu Gly Asp Thr Cys His Arg Gln Asp Asn Phe His
            180                 185                 190

Pro Phe Lys Asn Ser Val His Cys Leu
        195                 200

<210> SEQ ID NO 7
<211> LENGTH: 615
<212> TYPE: RNA
<213> ORGANISM: Brassica rapa

<400> SEQUENCE: 7
auggcgacag gaugugaa cgaagcccuu gcggcggcgg aaguaccggc aacagagacg      60
acggagaagc agccugcuga caagcucgaa agaaagugga guucugguu cgauaaccaa    120 uccaaaccaa agcaaggcgc cgccugggga gccuccuuc gcaaagccua uacccucgac    180
accguccaag acuucugggg gaucuucuuu ugcaguuugc acgagacuau auucaucccu    240
agcaaacuga cgccgaaugc ugaaauucac auguucaaag cugguguuga gccuaagugg    300
gaagauccug agugugcuaa uggcggaaag uggacuuuug uuguuaccuc caaccgcaag    360
ccugcuuuag acaaggcuug gcuugaaacu uugauggcuc uugucggaga gcaauuugau    420
gaggcugaug agaucugugg gguguugcu agugugcgcc caaagcagga caagcucucc    480
uuguggacaa ggaccaaauc uaaugaagcu guucugaugg uauugggaa gaaguggaag    540 gagauacuug augucaccga caagauaacu uucacuaacc augaugauuc uagaagaacu    600
agguucacug ucuga                                                    615

<210> SEQ ID NO 8
<211> LENGTH: 204
<212> TYPE: PRT
<213> ORGANISM: Brassica rapa
```

<400> SEQUENCE: 8

| | | | | | | | | | | | | | | |
|---|---|---|---|---|---|---|---|---|---|---|---|---|---|---|
| Met | Ala | Thr | Glu | Asp | Val | Asn | Glu | Ala | Leu | Ala | Ala | Ala | Glu | Val | Pro |
| 1 | | | | 5 | | | | | 10 | | | | | 15 | |
| Ala | Thr | Glu | Thr | Thr | Glu | Lys | Gln | Pro | Ala | Asp | Lys | Leu | Arg | Lys |
| | | 20 | | | | | 25 | | | | | 30 | | |
| Trp | Ser | Phe | Trp | Phe | Asp | Asn | Gln | Ser | Lys | Pro | Lys | Gln | Gly | Ala | Ala |
| | | 35 | | | | | 40 | | | | | 45 | | | |
| Trp | Gly | Ala | Ser | Leu | Arg | Lys | Ala | Tyr | Thr | Phe | Asp | Thr | Val | Gln | Asp |
| | 50 | | | | | 55 | | | | | 60 | | | | |
| Phe | Trp | Gly | Ile | Phe | Phe | Cys | Ser | Leu | His | Glu | Thr | Ile | Phe | Ile | Pro |
| 65 | | | | | 70 | | | | | 75 | | | | | 80 |
| Ser | Lys | Leu | Thr | Pro | Asn | Ala | Glu | Ile | His | Met | Phe | Lys | Ala | Gly | Val |
| | | | | 85 | | | | | 90 | | | | | 95 | |
| Glu | Pro | Lys | Trp | Glu | Asp | Pro | Glu | Cys | Ala | Asn | Gly | Gly | Lys | Trp | Thr |
| | | | 100 | | | | | 105 | | | | | 110 | | |
| Phe | Val | Val | Thr | Ser | Asn | Arg | Lys | Pro | Ala | Leu | Asp | Lys | Ala | Trp | Leu |
| | | | 115 | | | | | 120 | | | | | 125 | | |
| Glu | Thr | Leu | Met | Ala | Leu | Val | Gly | Glu | Gln | Phe | Asp | Glu | Ala | Asp | Glu |
| | 130 | | | | | 135 | | | | | 140 | | | | |
| Ile | Cys | Gly | Val | Val | Ala | Ser | Val | Arg | Pro | Lys | Gln | Asp | Lys | Leu | Ser |
| 145 | | | | | 150 | | | | | 155 | | | | | 160 |
| Leu | Trp | Thr | Arg | Thr | Lys | Ser | Asn | Glu | Ala | Val | Leu | Met | Gly | Ile | Gly |
| | | | | 165 | | | | | 170 | | | | | 175 | |
| Lys | Lys | Trp | Lys | Glu | Ile | Leu | Asp | Val | Thr | Asp | Lys | Ile | Thr | Phe | Thr |
| | | | 180 | | | | | 185 | | | | | 190 | | |
| Asn | His | Asp | Asp | Ser | Arg | Arg | Thr | Arg | Phe | Thr | Val |
| | | 195 | | | | | 200 | | | | |

<210> SEQ ID NO 9
<211> LENGTH: 597
<212> TYPE: RNA
<213> ORGANISM: Brassica rapa

<400> SEQUENCE: 9

```
auggcgacag aggaugugaa cgaagcccuu gcggcggcgg aaguaccggc aacagagacg    60
acggagaagc agccugcuga caagcucgaa agaaagugga guuucugguu cgauaaccaa   120
uccaaaccaa agcaaggcgc cgccugggga gccucccuuc gcaaagccua uccuucgac    180
accguccaag acuucuguuu gcacgagacu auauucaucc cuagcaaacu gacgccgaau   240
gcugaaauuc acauguucaa agcuggguguu gagccuaagu gggaagaucc ugagugugcu   300
aauggcggaa aguggacuuu uguuguuacc ccaaccgca agccugcuuu agacaaggcu   360
uggcuugaaa cuuugauggc ucuugucgga gagcaauuug augaggcuga ugagaucugu   420
ggggugguug cuagugugcg cccaaagcag acaagcucu ccuuguggac aaggaccaaa   480
ucuaaugaag cuguucugau ggguauuggg aagaagugga aggagauacu ugaugucacc   540
gacaagauaa cuuucacuaa ccaugaugau ucuagaagaa cucgguucac ugucuga      597
```

<210> SEQ ID NO 10
<211> LENGTH: 198
<212> TYPE: PRT
<213> ORGANISM: Brassica rapa

<400> SEQUENCE: 10

Met Ala Thr Glu Asp Val Asn Glu Ala Leu Ala Ala Ala Glu Val Pro

```
  1               5                  10                 15
Ala Thr Glu Thr Thr Glu Lys Gln Pro Ala Asp Lys Leu Glu Arg Lys
         20                  25                  30
Trp Ser Phe Trp Phe Asp Asn Gln Ser Lys Pro Lys Gln Gly Ala Ala
         35                  40                  45
Trp Gly Ala Ser Leu Arg Lys Ala Tyr Thr Phe Asp Thr Val Gln Asp
 50                  55                  60
Phe Cys Leu His Glu Thr Ile Phe Ile Pro Ser Lys Leu Thr Pro Asn
 65                  70                  75                  80
Ala Glu Ile His Met Phe Lys Ala Gly Val Glu Pro Lys Trp Glu Asp
                 85                  90                  95
Pro Glu Cys Ala Asn Gly Gly Lys Trp Thr Phe Val Val Thr Ser Asn
            100                 105                 110
Arg Lys Pro Ala Leu Asp Lys Ala Trp Leu Glu Thr Leu Met Ala Leu
            115                 120                 125
Val Gly Glu Gln Phe Asp Glu Ala Asp Glu Ile Cys Gly Val Val Ala
        130                 135                 140
Ser Val Arg Pro Lys Gln Asp Lys Leu Ser Leu Trp Thr Arg Thr Lys
145                 150                 155                 160
Ser Asn Glu Ala Val Leu Met Gly Ile Gly Lys Lys Trp Lys Glu Ile
                165                 170                 175
Leu Asp Val Thr Asp Lys Ile Thr Phe Thr Asn His Asp Asp Ser Arg
            180                 185                 190
Arg Thr Arg Phe Thr Val
        195

<210> SEQ ID NO 11
<211> LENGTH: 22
<212> TYPE: DNA
<213> ORGANISM: Artificial Sequence
<220> FEATURE:
<223> OTHER INFORMATION: PCR primer

<400> SEQUENCE: 11
atggcgacag aggatgtgaa cg                                          22

<210> SEQ ID NO 12
<211> LENGTH: 24
<212> TYPE: DNA
<213> ORGANISM: Artificial Sequence
<220> FEATURE:
<223> OTHER INFORMATION: PCR Primer

<400> SEQUENCE: 12
tctccttcca cttcttccca atac                                        24

<210> SEQ ID NO 13
<211> LENGTH: 30
<212> TYPE: DNA
<213> ORGANISM: Artificial Sequence
<220> FEATURE:
<223> OTHER INFORMATION: RT-PCT Primer

<400> SEQUENCE: 13
aaaaagcagg ctcgatggcg acagaggatg                                  30

<210> SEQ ID NO 14
<211> LENGTH: 35
<212> TYPE: DNA
<213> ORGANISM: Artificial Sequence
```

```
<220> FEATURE:
<223> OTHER INFORMATION: RT-PCT Primer

<400> SEQUENCE: 14
agaaagctgg gttcagacag tgaacctagt tcttc                              35

<210> SEQ ID NO 15
<211> LENGTH: 35
<212> TYPE: DNA
<213> ORGANISM: Artificial Sequence
<220> FEATURE:
<223> OTHER INFORMATION: RT-PCR Primer

<400> SEQUENCE: 15
agaaagctgg gttcagacag tgaaccgagt tcttc                              35

<210> SEQ ID NO 16
<211> LENGTH: 36
<212> TYPE: DNA
<213> ORGANISM: Artificial Sequence
<220> FEATURE:
<223> OTHER INFORMATION: PCR Primer

<400> SEQUENCE: 16
aaaaagcagg cttttggtct gcagttatgt tattag                             36

<210> SEQ ID NO 17
<211> LENGTH: 30
<212> TYPE: DNA
<213> ORGANISM: Artificial Sequence
<220> FEATURE:
<223> OTHER INFORMATION: PCR Primer

<400> SEQUENCE: 17
agaaagctgg gtaaaaaggc ttgcgagtca                                    30

<210> SEQ ID NO 18
<211> LENGTH: 20
<212> TYPE: DNA
<213> ORGANISM: Artificial Sequence
<220> FEATURE:
<223> OTHER INFORMATION: PCR Primer

<400> SEQUENCE: 18
caatggcggt agaagacact                                               20

<210> SEQ ID NO 19
<211> LENGTH: 20
<212> TYPE: DNA
<213> ORGANISM: Artificial Sequence
<220> FEATURE:
<223> OTHER INFORMATION: PCR Primer

<400> SEQUENCE: 19
agttgagttt ttgttcttac                                               20

<210> SEQ ID NO 20
<211> LENGTH: 36
<212> TYPE: DNA
<213> ORGANISM: Artificial Sequence
<220> FEATURE:
<223> OTHER INFORMATION: PCR Primer

<400> SEQUENCE: 20
aaaaagcagg cttaggacaa atgatatggg gagagt                             36
```

<210> SEQ ID NO 21
<211> LENGTH: 30
<212> TYPE: DNA
<213> ORGANISM: Artificial Sequence
<220> FEATURE:
<223> OTHER INFORMATION: PCR Primer

<400> SEQUENCE: 21
agaaagctgg gtagcttggc gaccttttga                              30

<210> SEQ ID NO 22
<211> LENGTH: 21
<212> TYPE: DNA
<213> ORGANISM: Artificial Sequence
<220> FEATURE:
<223> OTHER INFORMATION: PCR Primer

<400> SEQUENCE: 22
tgaaaggggc gaaaaacaca t                                       21

<210> SEQ ID NO 23
<211> LENGTH: 24
<212> TYPE: DNA
<213> ORGANISM: Artificial Sequence
<220> FEATURE:
<223> OTHER INFORMATION: PCR Primer

<400> SEQUENCE: 23
gcaaaccgac aaaataagga agaa                                    24

<210> SEQ ID NO 24
<211> LENGTH: 34
<212> TYPE: DNA
<213> ORGANISM: Artificial Sequence
<220> FEATURE:
<223> OTHER INFORMATION: PCR Primer

<400> SEQUENCE: 24
aaaaagcagg cttttttaag aatggaggga gtat                         34

<210> SEQ ID NO 25
<211> LENGTH: 29
<212> TYPE: DNA
<213> ORGANISM: Artificial Sequence
<220> FEATURE:
<223> OTHER INFORMATION: PCR Primer

<400> SEQUENCE: 25
agaaagctgg gtgaagcgcg ggtcaaaat                               29

<210> SEQ ID NO 26
<211> LENGTH: 36
<212> TYPE: DNA
<213> ORGANISM: Artificial Sequence
<220> FEATURE:
<223> OTHER INFORMATION: PCR Primer

<400> SEQUENCE: 26
aaaaagcagg cttttggtct gcaattatct tattag                       36

<210> SEQ ID NO 27
<211> LENGTH: 30
<212> TYPE: DNA
<213> ORGANISM: Artificial Sequence
<220> FEATURE:
<223> OTHER INFORMATION: PCR Primer

```
<400> SEQUENCE: 27
agaaagctgg gtaaaaaggc ttgcgagtca                                       30

<210> SEQ ID NO 28
<211> LENGTH: 36
<212> TYPE: DNA
<213> ORGANISM: Artificial Sequence
<220> FEATURE:
<223> OTHER INFORMATION: PCR Primer

<400> SEQUENCE: 28
aaaaagcagg cttaggacaa atgatatggg gagagt                                36

<210> SEQ ID NO 29
<211> LENGTH: 30
<212> TYPE: DNA
<213> ORGANISM: Artificial Sequence
<220> FEATURE:
<223> OTHER INFORMATION: PCR Primer

<400> SEQUENCE: 29
agaaagctgg gtagcttggc gaccttttga                                       30

<210> SEQ ID NO 30
<211> LENGTH: 21
<212> TYPE: DNA
<213> ORGANISM: Artificial Sequence
<220> FEATURE:
<223> OTHER INFORMATION: PCR Primer

<400> SEQUENCE: 30
tgaaaggggc gaaaaacaca t                                                21

<210> SEQ ID NO 31
<211> LENGTH: 24
<212> TYPE: DNA
<213> ORGANISM: Artificial Sequence
<220> FEATURE:
<223> OTHER INFORMATION: PCR Primer

<400> SEQUENCE: 31
gcaaaccgac aaaataagga agaa                                             24

<210> SEQ ID NO 32
<211> LENGTH: 32
<212> TYPE: DNA
<213> ORGANISM: Artificial Sequence
<220> FEATURE:
<223> OTHER INFORMATION: PCR Primer

<400> SEQUENCE: 32
aaaaagcagg ctcgaagaag tccgcataaa gc                                    32

<210> SEQ ID NO 33
<211> LENGTH: 32
<212> TYPE: DNA
<213> ORGANISM: Artificial Sequence
<220> FEATURE:
<223> OTHER INFORMATION: PCR Primer

<400> SEQUENCE: 33
agaaagctgg gtacccgtcc gtggattaaa ta                                    32

<210> SEQ ID NO 34
```

```
<211> LENGTH: 1157
<212> TYPE: DNA
<213> ORGANISM: Brassica rapa

<400> SEQUENCE: 34
atggcggtag aagacacact caagcctaat gtcgctacgg aagaatcgaa tcccaattct      60
gcagatcacc cgatcgatcg ataccatgag gaaggcgacg atgccgagga aggagcgacc    120
gtagacgaat cgagcaaatc cgccgtccct gaatcgcatc cgttggagca ttcgtggact    180
ctctggttcg ataacccttc cgtcaaatca agcagacga cttggggaag ctccttacga    240
tccgtcttca ccttctccac cgtcgaggag ttctggaggt tggtagcttt acaacaatct    300
tttccttct tacagtaatt ccacaatctg gttttgttt agattttgat ttctcacagg      360
aaagttatct tctttgttgt tgctgttaga atcttgtttg atgtttgaac aaacagttac    420
ttgttggatg ctagtgtatt ggctttgaca ttttactttt gatttgtagt ttgtacaata    480
acattcggca cccgagcaag ttagctaacg gagctgactt gtactgtttc aaacacaata    540
ttgaacctaa gtgggaggat cctatctgtg ccaacggagg caagtggact atgaacttct    600
ctagggagaa gtctgataag ccctttcttt acaccgtatg taacttgaca ttcatatagt    660
tcttgtttca caccatccag tctccagtct aatcggtt ttgttgttgt tgttgtcact      720
tgtagttgct tgctttgatt ggagaacagt ttgaccatgg agatgaaatc tgtggagttg    780
ttgttaacgt tagagctaag caagagagga tatctatttg gactaaaaac tcttccaacg    840
aagcggctca ggtacaagac aaaaaaaacc cacatcaaac tgtgtctctc tctcggtctg    900
aagaaaagac gtggaaattt tattttattt aatgttacag gtgagcattg ggagacagtg    960
gaaggagttt cttgattaca acagcagcat tggtttcatc atccatgtaa agagcgtttc   1020
tgttgttgct aatttctgtt tttttttct ttctatggat cgctcactac ttgttgtatg    1080
tgtgtattgg tttggtttct cttcaggagg atgcgaagaa gctggacaga ggcgcaaaga   1140
gcgcttacac tgcctga                                                   1157

<210> SEQ ID NO 35
<211> LENGTH: 687
<212> TYPE: RNA
<213> ORGANISM: Brassica rapa

<400> SEQUENCE: 35
auggcgguag aagacacacu caagccuaau gucgcuacgg aagaaucgaa ucccaauucu     60
gcagaucacc cgaucgaucg auaccaugag gaaggcgacg augccgagga aggagcgacc   120
guagacgaau cgagcaaauc cgccgucccu gaaucgcauc cguuggagca uucguggacu   180
cucugguucg auaacccuuc cgucaaauca agcagacga cuuggggaag cuccuuacga    240
uccgucuuca ccuucuccac cgucgaggag uucuggaguu uguacaauaa cauucggcac    300
ccgagcaagu uagcuaacgg agcugacuug uacuguuuca aacacaauau ugaaccuaag    360
ugggaggauc cuaucugugc caacggaggc aaguggacua ugaacuucuc uagggagaag    420
ucugauaagc ccuuucuuua caccuugcuu gcuugauug gagaacaguu ugaccaugga    480
gaugaaaucu guggaguugu uguuaacguu agagcuaagc aagagaggau aucuauuugg    540
acuaaaaacu cuuccaacga agcggcucag gugagcauug ggagacagug aaggaguuu    600
cuugauuaca acagcagcau gguuucauc auccaugagg augcgaagaa gcuggacaga    660
ggcgcaaaga gcgcuuacac ugccuga                                        687
```

<210> SEQ ID NO 36
<211> LENGTH: 228
<212> TYPE: PRT
<213> ORGANISM: Brassica rapa

<400> SEQUENCE: 36

```
Met Ala Val Glu Asp Thr Leu Lys Pro Asn Val Ala Thr Glu Glu Ser
1               5                   10                  15

Asn Pro Asn Ser Ala Asp His Pro Ile Asp Arg Tyr His Glu Glu Gly
            20                  25                  30

Asp Asp Ala Glu Glu Gly Ala Thr Val Asp Glu Ser Ser Lys Ser Ala
        35                  40                  45

Val Pro Glu Ser His Pro Leu Glu His Ser Trp Thr Leu Trp Phe Asp
    50                  55                  60

Asn Pro Ser Val Lys Ser Lys Gln Thr Thr Trp Gly Ser Ser Leu Arg
65                  70                  75                  80

Ser Val Phe Thr Phe Ser Thr Val Glu Glu Phe Trp Ser Leu Tyr Asn
                85                  90                  95

Asn Ile Arg His Pro Ser Lys Leu Ala Asn Gly Ala Asp Leu Tyr Cys
            100                 105                 110

Phe Lys His Asn Ile Glu Pro Lys Trp Glu Asp Pro Ile Cys Ala Asn
        115                 120                 125

Gly Gly Lys Trp Thr Met Asn Phe Ser Arg Glu Lys Ser Asp Lys Pro
    130                 135                 140

Phe Leu Tyr Thr Leu Leu Ala Leu Ile Gly Glu Gln Phe Asp His Gly
145                 150                 155                 160

Asp Glu Ile Cys Gly Val Val Asn Val Arg Ala Lys Gln Glu Arg
                165                 170                 175

Ile Ser Ile Trp Thr Lys Asn Ser Ser Asn Glu Ala Ala Gln Val Ser
            180                 185                 190

Ile Gly Arg Gln Trp Lys Glu Phe Leu Asp Tyr Asn Ser Ser Ile Gly
        195                 200                 205

Phe Ile Ile His Glu Asp Ala Lys Lys Leu Asp Arg Gly Ala Lys Ser
210                 215                 220

Ala Tyr Thr Ala
225
```

<210> SEQ ID NO 37
<211> LENGTH: 1189
<212> TYPE: DNA
<213> ORGANISM: Brassica rapa

<400> SEQUENCE: 37

```
atggcggtag aagacactct caagcctaac gtccctacgg aagaatcgaa tcccaattct      60
gtagatcacc cgatcgatcg ataccatgag gaaggcgacg atgccgagga aggagcgatc     120
gtagacgaat cgagcaaatc cgccgtccct gaatcgcatc cgttggagca ttcgtggact     180
ctctggttcg ataacccttc cgtcaaatca agcagacga cttggggaag ctccttacga     240
tccgtcttca ccttctccac cgtcgaggag ttctggaggt tggtagcttt acaacaatct     300
ttttccttct taatgtaatt ccacaatctg gttttgttt agatttcgat ttctcacagg     360
aaagttatct tctttatggg tgggtttaaa tctcatgaag tcactgttct tctctgtcta     420
tgaagaattg cctgttggt gtttgaacaa acagttactt gttggatgct atttattgg      480
cttcttatta tatgtgacat tgcagttgt acaataacat tcggcatccg agcaagttag     540
ctaacggagc tgacttgtac tatttcaaac acaatattga acctaagtgg gaggatccta     600
```

```
tctgtgccaa cggaggcaag tggactatga acttctctag ggagaagtct gataagccct    660
ttctttacac cgtatgtaac ttgacattca tatagttctt gtttcacacc atccagtctc    720
cagtctaatc gggttgttgt tgttgttgtc acttatagtt gcttgctttg attggagaac    780
agtttgacca tggagatgaa atctgtggag ttgttgttaa cgttagagct aagcaagaaa    840
ggatatctat ttggactaaa aactcttcca acgaagctgc tcaggtacaa gacaaaaaaa    900 gaaccccat cgaactgtat ctctctctcg gtctgaagaa aagacgtgga aattttatat     960
tgtttaatgt tacaggtgag cattgggaga cagtggaagg agtttcttga ttacaacagc   1020
agcattggtt tcatcatcca tgtaatagta tttctgttgt tgctaatttc tttcttttt    1080 tcttctatgg atcgctcact acttgttgta tgtgtgtatt ggtttggttt ctcttcagga   1140
ggatgcgaag aagctggaca gaggcgcaaa gagcgcttac actgcctga               1189

<210> SEQ ID NO 38
<211> LENGTH: 687
<212> TYPE: RNA
<213> ORGANISM: Brassica rapa

<400> SEQUENCE: 38
auggcgguag aagacacucu caagccuaac gucccuacgg aagaaucgaa ucccaauucu     60
guagaucacc cgaucgaucg auaccaugag gaaggcgacg augccgagga aggagcgauc    120
guagacgaau cgagcaaauc cgccgucccu gaaucgcauc cguuggagca uucguggacu    180
cucugguucg auaacccuuc cgucaaauca aagcagacga cuuggggaag cuccuuacga    240
uccgucuuca ccuucuccac cgucgaggag uucuggaguu uguacaauaa cauucggcau    300
ccgagcaagu uagcuaacgg agcugacuug uacuauuuca aacacaauau ugaaccuaag    360
ugggaggauc cuaucugugc caacggaggc aaguggacua ugaacuucuc uagggagaag    420
ucugauaagc ccuuucuuua cacguugcuu gcuuugauug gagaacaguu ugaccaugga    480
gaugaaaucu guggaguugu uguuaacguu agagcuaagc aagaaaggau aucuauuugg    540
acuaaaaacu cuuccaacga agcugcucag guagcauug ggagacagug gaaggaguuu    600
cuugauuaca acagcagcau ugguuucauc auccaugagg augcgaagaa gcuggacaga    660
ggcgcaaaga gcgcuuacac ugccuga                                       687

<210> SEQ ID NO 39
<211> LENGTH: 228
<212> TYPE: PRT
<213> ORGANISM: Brassica rapa

<400> SEQUENCE: 39

Met Ala Val Glu Asp Thr Leu Lys Pro Asn Val Pro Thr Glu Glu Ser
1               5                   10                  15

Asn Pro Asn Ser Val Asp His Pro Ile Asp Arg Tyr His Glu Glu Gly
            20                  25                  30

Asp Asp Ala Glu Glu Gly Ala Ile Val Asp Glu Ser Ser Lys Ser Ala
        35                  40                  45

Val Pro Glu Ser His Pro Leu Glu His Ser Trp Thr Leu Trp Phe Asp
    50                  55                  60

Asn Pro Ser Val Lys Ser Lys Gln Thr Thr Trp Gly Ser Ser Leu Arg
65                  70                  75                  80

Ser Val Phe Thr Phe Ser Thr Val Glu Glu Phe Trp Ser Leu Tyr Asn
                85                  90                  95
```

```
Asn Ile Arg His Pro Ser Lys Leu Ala Asn Gly Ala Asp Leu Tyr Tyr
            100                 105                 110

Phe Lys His Asn Ile Glu Pro Lys Trp Glu Asp Pro Ile Cys Ala Asn
        115                 120                 125

Gly Gly Lys Trp Thr Met Asn Phe Ser Arg Glu Lys Ser Asp Lys Pro
    130                 135                 140

Phe Leu Tyr Thr Leu Leu Ala Leu Ile Gly Glu Gln Phe Asp His Gly
145                 150                 155                 160

Asp Glu Ile Cys Gly Val Val Asn Val Arg Ala Lys Gln Glu Arg
                165                 170                 175

Ile Ser Ile Trp Thr Lys Asn Ser Ser Asn Glu Ala Ala Gln Val Ser
        180                 185                 190

Ile Gly Arg Gln Trp Lys Glu Phe Leu Asp Tyr Asn Ser Ser Ile Gly
    195                 200                 205

Phe Ile Ile His Glu Asp Ala Lys Lys Leu Asp Arg Gly Ala Lys Ser
210                 215                 220

Ala Tyr Thr Ala
225

<210> SEQ ID NO 40
<211> LENGTH: 910
<212> TYPE: DNA
<213> ORGANISM: Brassica rapa

<400> SEQUENCE: 40
atggcggtag aagacacttt caagcctgtt gttgctatca aggaagcgaa acctaattat      60
gtagagcatc tgattggacc aggcgacgat gcggaggaag gagagatcgt agacggagat     120
gttgacaaat ctggaaatcc acagttcctg aatcgcattc gttggagcat tgtggacatt     180
tccacagttc ctcttttat tcgttgactt tctaacgaaa agacgacttg gggaagctcc      240
ttagatccgc gttcacgttc tccacggtcg aggagtcctg gaggttggtg ctttaaaaca     300
atcttttcgt tcttccaata attctacaat ctgggttttg gtttggattt agatttctcg     360
aggaaagtta tgttctttgt tgatgggtta gatcacatga agtcatcgtt cttatctgtt     420
tctgaagaat tgtttgtttg atgtttgaat ttgtagctac aagcttatat gttaagtttt     480
taaaaagata gcgaagatat tatattcgat gtaaatcaat gttttacacc ttagtatttt     540
tgttggtaac agaagatgaa caaagagtta tttggttagt gttggatgct attgtattgc     600
tgtgcactcg tgtgtgtata tgctttcttg tattctcctt tcttgagaac cttctctca      660 atgggaataa tgaacttgta gtttgttcta ttgggagaca atagaaggag ttccttgatt     720
acaacagctg cattggtttc atcatccatg tgggaagagt gcttgtcttg atgctaattc     780
aaaaggcttt tcttttgcat ttctcagtgt ttattttttt gtctgtattg gcttgttttc     840
ccttcaggag gatgcgacga agatgaacaa gtacaaccat actgttatcg atctacaatt     900
tgagttttaa                                                             910

<210> SEQ ID NO 41
<211> LENGTH: 404
<212> TYPE: RNA
<213> ORGANISM: Brassica rapa

<400> SEQUENCE: 41
auggcgguag aagacacuuu caagccuguu guugcuauca aggaagcgaa accuaauuau      60
guagagcauc ugauuggacc aggcgacgau gcggaggaag gagagaucgu agacggagau     120
```

| guugacaaau cuggaaaucc acaguuccug aaucgcauuc guuggagcau uugguggacuu | 180 |
| uccacaguuc cucuuuuuau ucguugacuu ucuaacgaaa agacgacuug gggaagcucc | 240 |
| uuagauccgc guucacguuc uccacggucg aggaguucug gagugggaga caauagaagg | 300 |
| aguuccuuga uuacaacagc ugcauugguu ucaucaucca ugaggaugcg acgaagauga | 360 |
| acaaguacaa ccauacuguu aucgaucuac aauuugaguu uuaa | 404 |

```
<210> SEQ ID NO 42
<211> LENGTH: 132
<212> TYPE: PRT
<213> ORGANISM: Brassica rapa

<400> SEQUENCE: 42
```

Met Ala Val Glu Asp Thr Phe Lys Pro Val Val Ala Ile Lys Glu Ala
1               5                   10                  15

Lys Pro Asn Tyr Val Glu His Leu Ile Gly Pro Gly Asp Asp Ala Glu
            20                  25                  30

Glu Gly Glu Ile Val Asp Gly Val Asp Lys Ser Gly Asn Pro Gln
        35                  40                  45

Phe Leu Asn Arg Ile Arg Trp Ser Ile Cys Gly Leu Ser Thr Val Pro
    50                  55                  60

Leu Phe Ile Arg Leu Ser Asn Glu Lys Thr Thr Trp Gly Ser Ser Leu
65                  70                  75                  80

Asp Pro Arg Ser Arg Ser Pro Arg Ser Arg Ser Gly Val Gly Asp
                85                  90                  95

Asn Arg Arg Ser Ser Leu Ile Thr Thr Ala Ala Leu Val Ser Ser Ser
            100                 105                 110

Met Arg Met Arg Arg Arg Thr Ser Thr Thr Ile Leu Leu Ser Ile Tyr
        115                 120                 125

Asn Leu Ser Phe
    130

```
<210> SEQ ID NO 43
<211> LENGTH: 1567
<212> TYPE: DNA
<213> ORGANISM: Brassica rapa

<400> SEQUENCE: 43
```

| atggcggtag aagacacttc caagcctgtt gtcgttgcgg aagaagcgaa ccctaacccc | 60 |
| acagaccatc cgattgatcg ataccatgaa gaaggcgacg atgctgagga aggagagatc | 120 |
| gccggcggcg aaggagacgg agacgaatcg agcaaatccg ccgttccgca gtcgcatccg | 180 |
| ttggagcatt cgtggacttt ctggttcgat aacccttctg ttaaattaaa gcaggcgact | 240 |
| tggggaagct ccttgcgatc cgtgttcact ttctccaccg tcgaggagtt ctggaggtta | 300 |
| gggcttttta caaaatcaat aatttattct tacaattatt atttcgacat gggttttagt | 360 |
| ttggttttgt ctagattatg ttttctcgaa gaaagttatg ttcttcttc gtgggttaag | 420 |
| tgaatcactt gttcttgttt gtttctgaaa tattgctttg cttgtttgtt tggtgtttga | 480 |
| attatggaaa aggaatcttt tgttcttca atgactatgc ggcatgggtt ttggtttagt | 540 |
| tttgtttaga ttgttatatc tcaaggaaag ttatgttctt tgttggtggg ttagattccg | 600 |
| tgaagtcact tgctcttgta tgtttctgaa gaatcactta attggtgttt gagtttgtag | 660 |
| ctactgctta tatgttaagg tcatatttgt tcgcttgtta tcttcacaag agctaaaaca | 720 |
| ttgaaccagg gaatcatcgg tcttattcgg ttaatgttgg atgctattgt gttgttgcgt | 780 |

```
gtgtgtatat atactttctt gtgttcttct ttttgatttg tgagtctctc tcaagtctca    840
atgggattta aggacttgtc tttggctcta ttgacttcat cttactttgg ttgcagtctg    900
ttcaataaca tgaggggtcc gagcaagtta gctggcggag ctgacttcta ctgtttcaag    960
cacaatatcg aacctaagtg gaggatcct atctgtgcta atggaggcaa atggactatg   1020
aacttcccga aggagaagtc tgataagccc tggctttaca ccgtatggtt ttgattcttc   1080
ttacttgaac acatgattct tgtttcacca tccattcgag tctgattggg ttttgtttt   1140 ctcgatgtag ttgcttgcgt tgattggaga acagtttgac catggagatg agatatgcgg   1200
agctgttgtc aacgttagag gaaagcaaga gaggatttcc atttggacca aaaatgcttc   1260
caacgaagct gctcaggtaa agatcattt attgacaaat aaatgttaaa ttgtctctct   1320
tccggctaaa agacctgaaa tttcttgttt cctttgatgt tgcaggtgag cattgggaaa   1380
caatggaagg agtttattga ttacaacaac agcattggtt tcatcatcca tgtaagaaga   1440
gagcttttct cttgaatgct tattcataag tttttttta atatctcact gtctgtattg   1500 ttttttttt cttcaggagg atgccaagaa gctggacagg ggcgcgaaga gcgcttacac   1560
cgcttga                                                            1567
```

<210> SEQ ID NO 44
<211> LENGTH: 705
<212> TYPE: RNA
<213> ORGANISM: Brassica rapa

<400> SEQUENCE: 44

```
auggcgguag aagacacuuc caagccuguu gucguugcgg aagaagcgaa cccuaacccc    60
acagaccauc cgauugaucg auaccaugaa gaaggcgacg augcugagga aggagagauc   120
gccggcggcg aaggagacgg agacgaaucg agcaaauccg ccguuccgca gucgcauccg   180
uuggagcauu cguggacuuu cugguucgau aacccuucug uuaaauuaaa gcaggcgacu   240
uggggaagcu ccuugcgauc cguguucacu uucuccaccg ucgaggaguu cggagcucug   300
uucaauaaca ugaggggucc gagcaaguua gcuggcggag cugacuucua cuguuucaag   360
cacaauaucg aaccuaagug gaggauccu aucugugcua auggaggcaa auggacuaug   420
aacuucccga aggagaaguc ugauaagccc uggcuuuaca ccuugcuugc guugauugga   480
gaacaguuug accauggaga ugagauaugc ggagcuguug caacguuag aggaaagcaa   540 gagaggauuu ccauuuggac caaaaaugcu uccaacgaag cugcucaggu gagcauuggg   600
aaacaaugga aggaguuuau ugauuacaac aacagcauug guucaucau ccaugaggau   660 gccaagaagc uggacagggg cgcgaagagc gcuuacaccg cuuga                  705
```

<210> SEQ ID NO 45
<211> LENGTH: 234
<212> TYPE: PRT
<213> ORGANISM: Brassica rapa

<400> SEQUENCE: 45

```
Met Ala Val Glu Asp Thr Ser Lys Pro Val Val Ala Glu Glu Ala
 1               5                  10                  15

Asn Pro Asn Pro Thr Asp His Pro Ile Asp Arg Tyr His Glu Glu Gly
            20                  25                  30

Asp Asp Ala Glu Glu Gly Glu Ile Ala Gly Gly Glu Gly Asp Gly Asp
        35                  40                  45

Glu Ser Ser Lys Ser Ala Val Pro Gln Ser His Pro Leu Glu His Ser
    50                  55                  60
```

Trp Thr Phe Trp Phe Asp Asn Pro Ser Val Lys Leu Lys Gln Ala Thr
 65                  70                  75                  80

Trp Gly Ser Ser Leu Arg Ser Val Phe Thr Phe Ser Thr Val Glu Glu
                 85                  90                  95

Phe Trp Ser Leu Phe Asn Asn Met Arg Gly Pro Ser Lys Leu Ala Gly
            100                 105                 110

Gly Ala Asp Phe Tyr Cys Phe Lys His Asn Ile Glu Pro Lys Trp Glu
        115                 120                 125

Asp Pro Ile Cys Ala Asn Gly Gly Lys Trp Thr Met Asn Phe Pro Lys
130                 135                 140

Glu Lys Ser Asp Lys Pro Trp Leu Tyr Thr Leu Ala Leu Ile Gly
145                 150                 155                 160

Glu Gln Phe Asp His Gly Asp Glu Ile Cys Gly Ala Val Val Asn Val
                165                 170                 175

Arg Gly Lys Gln Glu Arg Ile Ser Ile Trp Thr Lys Asn Ala Ser Asn
            180                 185                 190

Glu Ala Ala Gln Val Ser Ile Gly Lys Gln Trp Lys Glu Phe Ile Asp
        195                 200                 205

Tyr Asn Asn Ser Ile Gly Phe Ile Ile His Glu Asp Ala Lys Lys Leu
210                 215                 220

Asp Arg Gly Ala Lys Ser Ala Tyr Thr Ala
225                 230

<210> SEQ ID NO 46
<211> LENGTH: 1568
<212> TYPE: DNA
<213> ORGANISM: Brassica rapa

<400> SEQUENCE: 46
atggcggtag aagacacttc caagcctgtt gtcgttgcgg aagaagcgaa ccctaacccc      60
acagaccatc cgattgatcg ataccatgaa gaaggcgacg atgttgagga aggagagatc     120
gccggcggcg aaacagacgg agacgaatcg agcaaatccg ccgttccgca gtcgcatccg     180
ttggagcatt cgtggacctt ctggttcgat aacccttctg ttaaattaaa gcaggcgact     240
tggggaagct ccttgcgatc cgtgttcact ttctccaccg tcgaggagtt ctggaggtta     300 gggctttttta caaaatcaat aatttattct tgcaatgatt atttcgacat ggttttagt     360 ttggttttgt ctagattatg ttttctcgag gaaagttatg ttctttcttc gtgggttaag     420
tcaagtcact tgttcttgtc tgtttctgaa gtatgacttg tttggtgttt gaattatgga     480
ggtcaggcct acaaaacaa tcttttgttc ttcttctgat tatttcgaca tgggttttag     540
tttggttttg tctagattat gttttctcga ggaaagttat gttctttctt gttgggttaa     600
gtgaagtcac ttgctcttgt ctgtttctga atattactt gtttggtgtt tgaaattgta     660
gctactgctt atatgttaag gtcatatttg ttcacttcta atcttcacaa gagctaaaac     720
attgaactag ggaatcattg gtcttatttg gttaatgttg gatgctattg tgttgttgcg     780
tgtgtgtata tatactttct tgtgttcttc ttttgatt gtgagtctct ctcaagtctc     840
aatgggattt aaggacttgt ctttggctct attgacttca tcttactttg gttgcagtct     900
gttcaataac atgaagggtc cgagcaagtt agctggcgga gctgacttct actgtttcaa     960
gcacaatatc gaacctaagt gggaggatcc tatctgtgct aatggaggca atggactat    1020 gaacttcccg aaggagaagt ctgataagcc ctggctttac actgtatggt ttgattctt    1080 cttacttgaa cacatgattc ttgtttcacc atccattcga gtctgattgg ttttttgttt    1140

```
tttccatgta gttgcttgcg ttgattggag aacagtttga ccacggagat gagatatgcg    1200
gagctgttgt caacgttaga ggaaagcaag agaggatttc catttggacc aaaaatgctt    1260
ccaacgaagc tgctcaggta aaagatcatt tattgacaaa taaatgttaa attgtctctc    1320
ttccggctaa aagacctgaa attcttgtt cctttgatg ttgcaggtga gcattgggaa     1380
acaatggaag gagtttattg attacaacaa cagcattggt ttcatcatcc atgtaagaag    1440
agagcttttc tcttgaatgc ttattcataa gttttttttt aatatctcac tgtctgtttt    1500
gttttttttt tcttcaggag gatgccaaga agctggacag gggcgcgaag agcgcttaca    1560
ccgcttga                                                             1568

<210> SEQ ID NO 47
<211> LENGTH: 705
<212> TYPE: RNA
<213> ORGANISM: Brassica rapa

<400> SEQUENCE: 47
auggcgguag aagacacuuc caagccuguu gucguugcgg aagaagcgaa cccuaacccc      60
acagaccauc cgauugaucg auaccaugaa gaaggcgacg auguugagga aggagagauc    120
gccggcggcg aaacagacgg agacgaaucg agcaaauccc cguuccgca gucgcauccg     180 uuggagcauu cguggaccuu cugguucgau aacccuucug uuaaauuaaa gcaggcgacu    240
uggggaagcu ccuugcgauc cguguucacu uucuccaccg ucgaggaguu cuggagucug    300
uucaauaaca ugaaggguucc gagcaaguua gcuggcggag cugacuucua cguguucaag    360
cacaauaucg aaccuaagug ggaggauccu aucgugcua auggaggcaa augggacuaug    420 aacuucccga aggagaaguc ugauaagccc uggcuuuaca cuuugcuugc guugauugga    480
gaacaguuug accacggaga ugagauaugc ggagcuguug ucaacguuag aggaaagcaa    540
gagaggauuu ccauuuggac caaaaaugcu uccaacgaag cugcucaggu gagcauuggg    600
aaacaaugga aggaguuuau ugauuacaac aacagcauug guuucaucau ccaugaggau    660
gccaagaagc uggacagggg cgcgaagagc gcuuacaccg cuuga                    705

<210> SEQ ID NO 48
<211> LENGTH: 234
<212> TYPE: PRT
<213> ORGANISM: Brassica rapa

<400> SEQUENCE: 48

Met Ala Val Glu Asp Thr Ser Lys Pro Val Val Ala Glu Glu Ala
1               5                   10                  15

Asn Pro Asn Pro Thr Asp His Pro Ile Asp Arg Tyr His Glu Glu Gly
            20                  25                  30

Asp Asp Val Glu Glu Gly Glu Ile Ala Gly Gly Glu Thr Asp Gly Asp
        35                  40                  45

Glu Ser Ser Lys Ser Ala Val Pro Gln Ser Pro Leu Glu His Ser
    50                  55                  60

Trp Thr Phe Trp Phe Asp Asn Pro Ser Val Lys Leu Lys Gln Ala Thr
65                  70                  75                  80

Trp Gly Ser Ser Leu Arg Ser Val Phe Thr Phe Ser Thr Val Glu Glu
                85                  90                  95

Phe Trp Ser Leu Phe Asn Asn Met Lys Gly Pro Ser Lys Leu Ala Gly
                100                 105                 110

Gly Ala Asp Phe Tyr Cys Phe Lys His Asn Ile Glu Pro Lys Trp Glu
```

```
                115                 120                 125
Asp Pro Ile Cys Ala Asn Gly Gly Lys Trp Thr Met Asn Phe Pro Lys
            130                 135                 140

Glu Lys Ser Asp Lys Pro Trp Leu Tyr Thr Leu Leu Ala Leu Ile Gly
145                 150                 155                 160

Glu Gln Phe Asp His Gly Asp Glu Ile Cys Gly Ala Val Val Asn Val
                165                 170                 175

Arg Gly Lys Gln Glu Arg Ile Ser Ile Trp Thr Lys Asn Ala Ser Asn
            180                 185                 190

Glu Ala Ala Gln Val Ser Ile Gly Lys Gln Trp Lys Glu Phe Ile Asp
            195                 200                 205

Tyr Asn Asn Ser Ile Gly Phe Ile Ile His Glu Asp Ala Lys Lys Leu
            210                 215                 220

Asp Arg Gly Ala Lys Ser Ala Tyr Thr Ala
225                 230

<210> SEQ ID NO 49
<211> LENGTH: 1283
<212> TYPE: DNA
<213> ORGANISM: Brassica rapa

<400> SEQUENCE: 49
atggcgacgg aggatgtgaa cgaagccctt gcggcggcgg aagtaccgat agagtcgaca      60
acggagaagc agcctcataa gctggaaaga aaatggtgtt ctggttcga taaccaatct     120 aagccaaagc aaggcgccgc ctggggagct tcccttcgta aagcctctac cttcgacact     180
gtcgaagatt tctgggggtg tgtcgtgtct tcttctcctc ctcattttta gatttcttcg     240
attaacttct tctggcatgc gttttttgcag tttgcacgag actatattca ttcccagcaa     300
attgacaccc aatgctgata tccacttgtt caaagctggc gttgagccca agtgggaaga     360
tcctgagtgt gctcacggcg aaagtggac ttttgttgtc accaacaaca ggaagcaagc     420
tttagacaag gcttggcttg aaactgtaat accgtcttcc cttttactgt ttttgtcttt     480
agacaattgt ggcttatgtc ctaatgtctg tttcttctct ctctctctcg taattgggcg     540
gcagttgatg gctttgattg agagcaatt cgatgaggca gatgagattt gtggtgttgt     600
tgctagtgtg cgcctaaagc aagacaagct ctccttgtgg acacggacta aatcaaatga     660
agctgtcctg gttagattac gaatcatgtt ttcttctagt tgtctttttt tttttttttt     720
ttcattttct tgcttttttgg tggtgtgcga tgagatgccc aagtactatt cactagcttc     780
ctttgttgaa cgtgttgatt gctttctaca gtaaatagc ataagctgtt taatatatca     840
ataacgctac tctaaattat caacgaaaga tgtagagagg tttttttataa tgagttaaat     900 tagtttttat actgaaggtt tataggttcg tttaactatt catatttctg tgatacctgc     960
ttttatagtt tacgctctat aaacatagca tttgacagct ctttagaaca tggcagtatc    1020
tagatgctaa aagactagtt tctgaatctg tctgcttaaa ttactgcttt gttgtttgtt    1080
atggtaaatt cagatgggta ttggaaagaa gtggaaggcg ctacttgacg tcaccgacaa    1140
gataactttc actaaccatg taattaacgt tctcctatag aagctaatat tacttttgtt    1200
catgtttatc ctttcacgtg cttactaaaa tctggtctac ttacttgcag gatgattcta    1260
gaagaagtcg gttcactgtc tga                                            1283

<210> SEQ ID NO 50
<211> LENGTH: 597
<212> TYPE: RNA
```

<213> ORGANISM: Brassica rapa

<400> SEQUENCE: 50

| | | | | |
|---|---|---|---|---|
| auggcgacgg aggaugugaa cgaagcccuu gcggcggcgg aaguaccgau agagucgaca | 60 |
| acggagaagc agccucauaa gcuggaaaga aaaugguguu ucugguucga uaaccaaucu | 120 |
| aagccaaagc aaggcgccgc cugggggagcu ucccuucgua aagccucuac cuucgacacu | 180 |
| gucgaagauu ucuggggguuu gcacgagacu auauucauuc ccagcaaauu gacacccaau | 240 |
| gcugauaucc acuuguucaa agcuggcguu gagcccaagu ggaagaucc ugagugugcu | 300 |
| cacggcggaa aguggacuuu uguugucacc aacaacagga agcaagcuuu agacaaggcu | 360 |
| uggcuugaaa cuugauggc uuugauugga gagcaauucg augaggcaga ugagauuugu | 420 |
| ggguuguug cuagugugcg ccuaaagcaa gacaagcucu ccuuguggac acggacuaaa | 480 |
| ucaaaugaag cuguccugau ggguauugga agaagugga aggcgcuacu ugacgucacc | 540 |
| gacaagauaa cuucacuaa ccaugaugau ucuagaagaa gucgguucac ugucuga | 597 |

<210> SEQ ID NO 51
<211> LENGTH: 198
<212> TYPE: PRT
<213> ORGANISM: Brassica rapa

<400> SEQUENCE: 51

```
Met Ala Thr Glu Asp Val Asn Glu Ala Leu Ala Ala Glu Val Pro
1               5                   10                  15

Ile Glu Ser Thr Thr Glu Lys Gln Pro His Lys Leu Glu Arg Lys Trp
            20                  25                  30

Cys Phe Trp Phe Asp Asn Gln Ser Lys Pro Lys Gln Gly Ala Ala Trp
        35                  40                  45

Gly Ala Ser Leu Arg Lys Ala Ser Thr Phe Asp Thr Val Glu Asp Phe
    50                  55                  60

Trp Gly Leu His Glu Thr Ile Phe Ile Pro Ser Lys Leu Thr Pro Asn
65                  70                  75                  80

Ala Asp Ile His Leu Phe Lys Ala Gly Val Glu Pro Lys Trp Glu Asp
                85                  90                  95

Pro Glu Cys Ala His Gly Gly Lys Trp Thr Phe Val Val Thr Asn Asn
            100                 105                 110

Arg Lys Gln Ala Leu Asp Lys Ala Trp Leu Glu Thr Leu Met Ala Leu
        115                 120                 125

Ile Gly Glu Gln Phe Asp Glu Ala Asp Glu Ile Cys Gly Val Val Ala
    130                 135                 140

Ser Val Arg Leu Lys Gln Asp Lys Leu Ser Leu Trp Thr Arg Thr Lys
145                 150                 155                 160

Ser Asn Glu Ala Val Leu Met Gly Ile Gly Lys Lys Trp Lys Ala Leu
                165                 170                 175

Leu Asp Val Thr Asp Lys Ile Thr Phe Thr Asn His Asp Asp Ser Arg
            180                 185                 190

Arg Ser Arg Phe Thr Val
        195
```

<210> SEQ ID NO 52
<211> LENGTH: 1283
<212> TYPE: DNA
<213> ORGANISM: Brassica rapa

<400> SEQUENCE: 52

```
atggcgacgg aggatgtgaa cgaagccctt gcggcggcgg aagtaccgat agagtcgaca      60
acggagaagc agcctcataa gctggaaaga aaatggtgtt tctggttcga taaccaatct     120
aagccaaagc aaggcgccgc ctggggagct tcccttcgta aagcctctac cttcgacact     180
gtcgaagatt tctggggtg tgtcgtgtct tcttctcctc ctcatttta gatttcttcg       240
attaacttct tctggcatgc gttttgcag tttgcacgag actatattca ttcccagcaa      300
attgacaccc aatgctgata tccacttgtt caaagctggc gttgagccca agtgggaaga    360
tcctgagtgt gctcacggcg gaaagtggac ttttgttgtc accaacaaca ggaagcaagc    420
tttagacaag gcttggcttg aaactgtaat accgtcttcc cttttactgt ttttgtcttt    480
agacaattgt ggcttatgtc ctaatgtctg tttcttctct ctctctctcg taattgggcg    540
gcagttgatg gctttgattg gagagcaatt cgatgaggca gatgagattt gtggtgttgt    600
tgctagtgtg cgcctaaagc aagacaagct ctccttgtgg acacggacta aatcaaatga    660
agctgtcctg gttagattac gaatcatgtt ttcttctagt tgtctttttt tttttttttt    720
ttcattttct tgcttttgg tggtgtgcga tgagatgccc aagtactatt cactagcttc     780
ctttgttgaa cgtgttgatt gctttctaca gtaaaatagc ataagctgtt taatatatca    840
ataacgctac tctaaattat caacgaaaga tgtagagagg ttttttataa tgagttaaat    900
tagtttttat actgaaggtt tataggttcg tttaactatt catatttctg tgatacctgc    960
ttttatagtt tacgctctat aaacatagca tttgacagct cttagaaca tggcagtatc    1020
tagatgctaa aagactagtt tctgaatctg tctgcttaaa ttactgcttt gttgtttgtt   1080
atggtaaatt cagatgggta ttggaaagaa gtggaaggcg ctacttgacg tcaccgacaa   1140
gataacttc actaaccatg taattaacgt tctcctatag aagctaatat tacttttgtt   1200
catgtttatc ctttcacgtg cttactaaaa tctggtctac ttacttgcag gatgattcta   1260
gaagaagtcg gttcactgtc tga                                           1283
```

<210> SEQ ID NO 53
<211> LENGTH: 597
<212> TYPE: RNA
<213> ORGANISM: Brassica rapa

<400> SEQUENCE: 53

```
auggcgacgg aggaugugaa cgaagcccuu gcggcggcgg aaguaccgau agagucgaca      60
acggagaagc agccucauaa gcuggaaaga aaauggugu ucugguucga uaaccaaucu     120
aagccaaagc aaggcgccgc cugggagcu ucccuucgua aagccucuac cuucgacacu    180
gucgaagauu ucugggguuu gcacgagacu auaucauuc ccagcaaauu gacacccaau    240
gcugauaucc acuuguucaa agcuggcguu gagcccaagu ggaagaucc ugagugugcu    300
cacggcggaa aguggacuuu uguugucacc aacaacagga agcaagcuuu agacaaggcu   360
uggcuugaaa cuuugaugcc uuugauugga gagcaauucg augaggcaga ugagauuugu   420
gguguugcu uaguagugcg ccuaaagcaa gacaagcucu ccuuguggac acggacuaaa    480
ucaaaugaag cuguccugau gguauuggaa gaaguggaa aggcgcuacu ugacgucacc    540
gacaagauaa cuuucacuaa ccaugaugau ucuagaagaa gucgguucac ugucuga      597
```

<210> SEQ ID NO 54
<211> LENGTH: 198
<212> TYPE: PRT
<213> ORGANISM: Brassica rapa

<400> SEQUENCE: 54

Met Ala Thr Glu Asp Val Asn Glu Ala Leu Ala Ala Glu Val Pro
1               5                   10                  15

Ile Glu Ser Thr Thr Glu Lys Gln Pro His Lys Leu Glu Arg Lys Trp
            20                  25                  30

Cys Phe Trp Phe Asp Asn Gln Ser Lys Pro Lys Gln Gly Ala Ala Trp
        35                  40                  45

Gly Ala Ser Leu Arg Lys Ala Ser Thr Phe Asp Thr Val Glu Asp Phe
50                  55                  60

Trp Gly Leu His Glu Thr Ile Phe Ile Pro Ser Lys Leu Thr Pro Asn
65                  70                  75                  80

Ala Asp Ile His Leu Phe Lys Ala Gly Val Glu Pro Lys Trp Glu Asp
                85                  90                  95

Pro Glu Cys Ala His Gly Gly Lys Trp Thr Phe Val Val Thr Asn Asn
            100                 105                 110

Arg Lys Gln Ala Leu Asp Lys Ala Trp Leu Glu Thr Leu Met Ala Leu
        115                 120                 125

Ile Gly Glu Gln Phe Asp Glu Ala Asp Glu Ile Cys Gly Val Val Ala
130                 135                 140

Ser Val Arg Leu Lys Gln Asp Lys Leu Ser Leu Trp Thr Arg Thr Lys
145                 150                 155                 160

Ser Asn Glu Ala Val Leu Met Gly Ile Gly Lys Lys Trp Lys Ala Leu
                165                 170                 175

Leu Asp Val Thr Asp Lys Ile Thr Phe Thr Asn His Asp Asp Ser Arg
            180                 185                 190

Arg Ser Arg Phe Thr Val
        195

<210> SEQ ID NO 55
<211> LENGTH: 1148
<212> TYPE: DNA
<213> ORGANISM: Brassica rapa

<400> SEQUENCE: 55
atggcgacag aggatgtgaa cgaagccctt gcggcggcgg aggtaacggc gatagaatcg      60
acggagaagc agcagcctcc tcacaagctc gaaagaaagt ggagtctctg gttcgataac     120
caatcgaaac ccaagcaagg cgccgcctgg ggagtttccc tccgtaaagc atgtaccttc     180
gataccgtcg aagacttctg ggggtttgtc ttttcttct tcgatctaag attttctgtg      240
aagttatact aataagggtg tgtgtattgt tgcagtttgc acgagactat cttcgttccc     300
agcagattga cacccaacgc tgacattcac atgttcaaag ctggtgttga gcccaagtgg     360
gaagatcctg agtgtgctaa cggcggaaag tggacttatg ttgttaccaa caacaggaag     420
caagctttag acaaggcttg gcttgaaact gtactcttct tcttcttcta accctttta      480 ctcttctgtt ttctgactta ataatttat ctcttgtgtt tggcagttga tggctttagt      540
tggagagcag tttgatgagg cagatgagat ctgtggtgtg gttgctagtg tccgccaaaa     600
gcaagacaag ctctccttgt ggactaggac taaatctaat gaagctgttc tggtatcatg     660
cttctcttct cccttatata tgtttgtttg acagttttt aaaccacctt ttgatacttt      720
gctgacagta taatcataag ctatatttgc caaaggatat atatatatca gtttagaaca     780
tgttagtatg tcaaagatgg tttatgaatc tatctatcgg atgaaattgc tgcttgttgt     840
ttgtttattg ttattatgtt ttatattggt ttatgatcct atctgatgag atttctactc     900
tgctgtatat ttagattgat ttatgaattt atctgatgaa actactacac tttgttgtaa     960

```
acctagatgg gtattgggaa gaagtggaag gagatacttg atgtcactga caagatatct   1020
ttcactaacc atgtaattac tacttcccca cgtaaaaagc taataaatca tccttttgtt   1080
agttcctttt taaactgtgg tctaaatata tgcaggatga tgcaagaaga agtcgattta   1140
gtgtctaa                                                            1148
```

<210> SEQ ID NO 56
<211> LENGTH: 603
<212> TYPE: RNA
<213> ORGANISM: Brassica rapa

<400> SEQUENCE: 56

```
auggcgacag aggaugugaa cgaagcccuu gcggcggcgg agguaacggc gauagaaucg    60
acggagaagc agcagccucc ucacaagcuc gaaagaaagu ggagucucug guucgauaac   120
caaucgaaac ccaagcaagg cgccgccugg ggaguuuccc uccguaaagc auguaccuuc   180
gauaccgucg aagacuucug ggguuugcac gagacuaucu ucguucccag cagauugaca   240
cccaacgcug acauucacau guucaaagcu ggguguugagc ccaaguggga agauccugag   300
ugugcuaacg gcggaaagug gacuuauguu guuaccaaca acaggaagca agcuuuagac   360
aaggcuuggc uugaaacuuu gauggcuuua guuggagagc aguugauga ggcagaugag    420 aucuguggug ugguugcuag uguccgccaa aagcaagaca agcucuccuu guggacuagg   480
acuaaaucua augaagcugu ucugaugggu auugggaaga guggaagga gauacuugau    540 gucacugaca agauaucuuu cacuaaccau gaugaugcaa gaagaagucg auuuagugc    600 uaa                                                                603
```

<210> SEQ ID NO 57
<211> LENGTH: 200
<212> TYPE: PRT
<213> ORGANISM: Brassica rapa

<400> SEQUENCE: 57

```
Met Ala Thr Glu Asp Val Asn Glu Ala Leu Ala Ala Ala Glu Val Thr
1               5                   10                  15

Ala Ile Glu Ser Thr Glu Lys Gln Gln Pro His Lys Leu Glu Arg
            20                  25                  30

Lys Trp Ser Leu Trp Phe Asp Asn Gln Ser Lys Pro Lys Gln Gly Ala
35                  40                  45

Ala Trp Gly Val Ser Leu Arg Lys Ala Cys Thr Phe Asp Thr Val Glu
    50                  55                  60

Asp Phe Trp Gly Leu His Glu Thr Ile Phe Val Pro Ser Arg Leu Thr
65                  70                  75                  80

Pro Asn Ala Asp Ile His Met Phe Lys Ala Gly Val Glu Pro Lys Trp
                85                  90                  95

Glu Asp Pro Glu Cys Ala Asn Gly Gly Lys Trp Thr Tyr Val Val Thr
            100                 105                 110

Asn Asn Arg Lys Gln Ala Leu Asp Lys Ala Trp Leu Glu Thr Leu Met
        115                 120                 125

Ala Leu Val Gly Glu Gln Phe Asp Glu Ala Asp Glu Ile Cys Gly Val
    130                 135                 140

Val Ala Ser Val Arg Gln Lys Gln Asp Lys Leu Ser Leu Trp Thr Arg
145                 150                 155                 160

Thr Lys Ser Asn Glu Ala Val Leu Met Gly Ile Gly Lys Lys Trp Lys
                165                 170                 175
```

```
Glu Ile Leu Asp Val Thr Asp Lys Ile Ser Phe Thr Asn His Asp Asp
            180                 185                 190

Ala Arg Arg Ser Arg Phe Ser Val
            195                 200

<210> SEQ ID NO 58
<211> LENGTH: 1128
<212> TYPE: DNA
<213> ORGANISM: Brassica rapa

<400> SEQUENCE: 58
atggcgacag aggatgtgaa cgaagccctt gcggcggcgg aggtaacggc gatagaatcg      60
acggagaagc agcagcctcc tcacaagctc gaaagaaagt ggagtttctg gttcgataac     120
caatcgaaac ccaagcaagg cgccgcctgg ggagcttccc tccgtaaagc atgtaccttc     180
gataccgtcg aagacttctg ggggtttgtc ttttcttct tcgatctaag attttctgtg      240
aagttatact aataggggtg tgtgtattgt tgcagtttgc acgagactat cttcgttccc     300
agcagattga tacccaacgc tgacattcac atgttcaaag ctggtgttga gcccaagtgg     360
gaagatcctg agtgtgctaa cggcggaaag tggacttatg ttgttaccaa caacaggaag     420
caagctttag acaaggcttg gcttgaaact gtactcttct tcttcttcta accttttta     480 ctcttctgtt ttctgactta ataatttat ctcttgtgtt tggcagttga tggctttagt      540
tggagagcag tttgatgagg cagatgagat ctgtggtgtg gttgctagtg tccgcccaaa     600
gcaagacaag ctctccttgt ggactaggac taaatctaat gaagctgttc tggtatcatg     660
cttctcttct cccttatata tgtttgtttg acagtttttt aaaccacctt ttgatacttt     720
gctgacagta taatcataag ctatatttgc caaaggatat gttagtatgt caaagatggt     780
ttatgaatct atatatctga tgaaattgtt gtttgttgtt tgtttattgt tattatgttt     840
tatattggtt tatgatccta tctgatgaga tttctactct gctatatatt tagattggtt     900
tatgaattta tctgacgaaa ctaatacact ttgtttgtaa acctagatgg gtattgggaa     960
gaagtggaag gagatacttg atgtcaccga caagatatct ttcactaacc atgtaattac    1020
tacttcccca cgtaaaaagc taatcaatca tccttttgtt agtgcctttt taaactgtgg    1080
tctatgtata tgcaggatga tgcaagaaga agtcgattta gtgtctga                 1128

<210> SEQ ID NO 59
<211> LENGTH: 603
<212> TYPE: RNA
<213> ORGANISM: Brassica rapa

<400> SEQUENCE: 59
auggcgacag aggaugugaa cgaagcccuu gcggcggcgg agguaacggc gauagaaucg      60
acggagaagc agcagccucc ucacaagcuc gaaagaaagu ggaguuucug guucgauaac     120
caaucgaaac ccaagcaagg cgccgccugg ggagcuuccc uccguaaagc auguaccuuc     180
gauaccgucg aagacuucug ggguuugcac gagacuaucu ucguucccag cagauugaua     240
cccaacgcug acauucacau guucaaagcu gguguugagc ccagugggga agauccugag     300
ugugcuaacg gcggaaagug gacuuauguu guuaccaaca caggaagca agcuuuagac     360 aaggcuuggc uugaaacuuu gaugcuuuua guggagagca guuugauga ggcagaugag      420 aucuguggug ugguugcuag uguccgccca aagcaagaca agcucuccuu guggacuagg     480
acuaaaucua augaagcugu ucugaugggu auugggaaga guggaagga gauacuugau      540
```

```
gucaccgaca agauaucuuu cacuaaccau gaugaugcaa gaagaagucg auuuaguguc        600
uga                                                                     603

<210> SEQ ID NO 60
<211> LENGTH: 200
<212> TYPE: PRT
<213> ORGANISM: Brassica rapa

<400> SEQUENCE: 60

Met Ala Thr Glu Asp Val Asn Glu Ala Leu Ala Ala Ala Glu Val Thr
1               5                   10                  15

Ala Ile Glu Ser Thr Glu Lys Gln Gln Pro Pro His Lys Leu Glu Arg
            20                  25                  30

Lys Trp Ser Phe Trp Phe Asp Asn Gln Ser Lys Pro Lys Gln Gly Ala
        35                  40                  45

Ala Trp Gly Ala Ser Leu Arg Lys Ala Cys Thr Phe Asp Thr Val Glu
    50                  55                  60

Asp Phe Trp Gly Leu His Glu Thr Ile Phe Val Pro Ser Arg Leu Ile
65                  70                  75                  80

Pro Asn Ala Asp Ile His Met Phe Lys Ala Gly Val Glu Pro Lys Trp
                85                  90                  95

Glu Asp Pro Glu Cys Ala Asn Gly Gly Lys Trp Thr Tyr Val Val Thr
            100                 105                 110

Asn Asn Arg Lys Gln Ala Leu Asp Lys Ala Trp Leu Glu Thr Leu Met
        115                 120                 125

Ala Leu Val Gly Glu Gln Phe Asp Glu Ala Asp Glu Ile Cys Gly Val
    130                 135                 140

Val Ala Ser Val Arg Pro Lys Gln Asp Lys Leu Ser Leu Trp Thr Arg
145                 150                 155                 160

Thr Lys Ser Asn Glu Ala Val Leu Met Gly Ile Gly Lys Lys Trp Lys
                165                 170                 175

Glu Ile Leu Asp Val Thr Asp Lys Ile Ser Phe Thr Asn His Asp Asp
            180                 185                 190

Ala Arg Arg Ser Arg Phe Ser Val
        195                 200

<210> SEQ ID NO 61
<211> LENGTH: 24
<212> TYPE: DNA
<213> ORGANISM: Brassica rapa

<400> SEQUENCE: 61
tctccttcca cttcttccca atac                                              24

<210> SEQ ID NO 62
<211> LENGTH: 24
<212> TYPE: DNA
<213> ORGANISM: Brassica rapa

<400> SEQUENCE: 62
tagacaaggc ttggcttgaa actg                                              24
```

The invention claimed is:

1. A method for producing a Turnip Mosaic virus-resistant *Brassica* plant, the method comprising:

(a) isolating a nucleic acid sample from a test *Brassica* plant;

(b) detecting in the nucleic acid sample, using PCR amplification, the presence of:

(i) a BraA.eIF(iso)4E.a allele encoding a plant eukaryotic initiation factor 4E isoform A (eIF(iso)4E.a) protein that is non-functional for a Turnip Mosaic virus, wherein the eIF(iso)4E.a protein is non-functional because a nucleic acid encoding the eIF(iso)4E.a protein is mis-spliced as a result of an insertion of a guanine at position +1 of the 5' splice site of intron 1 at the BraA.eIF(iso)4E.a locus; and (ii) a BraA.eIF(iso)4E.c allele encoding the eIF(iso)4E.c protein comprising an amino acid sequence of SEQ ID NO: 60;

wherein said PCR amplification uses oligonucleotide primers:

1. a forward primer comprising TCTCCTTCCACT-TCTTCCCAATAC (SEQ ID NO: 61), and
2. a reverse primer of TAGACAAGGCTTGGCTT-GAAACTG (SEQ ID NO: 62);

and wherein a PCR amplification product of 749 basepairs indicates the presence of said BraA.eIF(iso)4E.a allele, and a PCR amplification product of 546 basepairs indicates the presence of said BraA.eIF(iso)4E.c allele;

(c) selecting the test plant as resistant to Turnip Mosaic virus based on the presence of (i) and (ii) above;

(d) crossing the Turnip Mosaic virus-resistant test plant with a susceptible recipient *Brassica* plant to produce a progeny *Brassica* plant; and (e) self-pollinating or selfing the progeny *Brassica* plant produced in (d) or backcrossing the progeny *Brassica* plant produced in (d) with the test *Brassica* plant to produce a further progeny *Brassica* plant that is (i) homozygous for the allele at the BraA.eIF(iso)4E.a locus, and (ii) is homozygous or heterozygous for the allele at the BraA.eIF(iso)4E.c locus;

to thereby produce a *Brassica* plant that is resistant to Turnip Mosaic virus.

2. The method according to claim 1, wherein the recipient plant comprises at least one trait selected from the group consisting of an agronomic advantage, a commercial advantage, and/or suitability for a particular climate or soil.

3. The method according to claim 1, wherein the test plant is a transgenic plant.

4. The method according to claim 1, wherein the recipient plant is a *Brassica napus* plant; a *Brassica rapa* plant; or a *Brassica oleracea* plant.

* * * * *